(12) United States Patent
Yodfat et al.

(10) Patent No.: US 9,408,967 B2
(45) Date of Patent: *Aug. 9, 2016

(54) DEVICE FOR DRUG DELIVERY

(71) Applicant: Roche Diabetes Care, Inc., Indianapolis, IN (US)

(72) Inventors: Ofer Yodfat, Maccabim-Reut (IL); Gabriel J. Iddan, Haifa (IL); Illai Gescheit, Tel-aviv (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 362 days.

This patent is subject to a terminal disclaimer.

(21) Appl. No.: 13/919,616

(22) Filed: Jun. 17, 2013

(65) Prior Publication Data
US 2013/0281928 A1 Oct. 24, 2013

Related U.S. Application Data

(63) Continuation of application No. 12/733,009, filed as application No. PCT/IL2008/001058 on Jul. 31, 2008, now Pat. No. 8,465,460.

(60) Provisional application No. 60/963,071, filed on Aug. 1, 2007, provisional application No. 61/003,169, filed on Nov. 14, 2007.

(51) Int. Cl.
*A61M 5/142* (2006.01)
*A61M 5/14* (2006.01)
*A61M 5/145* (2006.01)

(52) U.S. Cl.
CPC .......... *A61M 5/14244* (2013.01); *A61M 5/1413* (2013.01); *A61M 5/1424* (2013.01);

(Continued)

(58) Field of Classification Search
CPC .......... A61M 5/1413; A61M 5/14244; A61M 5/14248; A61M 5/14228; A61M 5/14232; A61M 5/14236; A61M 5/1456; A61M 5/1424
See application file for complete search history.

(56) References Cited

U.S. PATENT DOCUMENTS 3,279,653 A 10/1966 Pfleger
4,676,122 A 6/1987 Szabo et al.
(Continued)

FOREIGN PATENT DOCUMENTS

WO WO-9723252 A1 7/1997
WO WO-2006121921 A2 11/2006
(Continued)

OTHER PUBLICATIONS

DCCT Trial Research Group, "The Effect of Intensive Treatment of Diabetes on the Development and Progression of Long-Term Complications in Insulin-Dependent Diabetes Mellitus", *N. E. J. Med.*, 329:977-986 (1993).
Powers, A. C., "Diabetes Mellitus", in *Harrison's Principles of Internal Medicine*, 16th Edition, Kasper et al., Eds., McGraw-Hill, New York, Chapter 323, pp. 2151-2180 (2005).

(Continued)

*Primary Examiner* — Laura Bouchelle
(74) *Attorney, Agent, or Firm* — Dinsmore & Shohl LLP

(57) ABSTRACT

Disclosed is an ambulatory therapeutic fluid delivery device. The device includes at least one housing connectable to a cannula, the at least one housing retaining a reservoir to hold the therapeutic fluid. The device also includes a mechanically powered pumping mechanism to cause delivery of at least some of the fluid from the reservoir, and a power-transfer mechanism to transfer manually-delivered power provided by a user to mechanically actuate the pumping mechanism.

24 Claims, 43 Drawing Sheets

(52) U.S. Cl.
CPC ......... *A61M5/1454* (2013.01); *A61M 5/14248* (2013.01); *A61M 5/1456* (2013.01); *A61M 5/14232* (2013.01); *A61M 2005/1405* (2013.01); *A61M 2205/071* (2013.01); *A61M 2209/045* (2013.01)

(56) References Cited

U.S. PATENT DOCUMENTS

| | | | |
|---|---|---|---|
| 5,830,187 | A | 11/1998 | Kriesel et al. |
| 6,500,150 | B1 * | 12/2002 | Gross et al. .................. 604/131 |
| 8,465,460 | B2 * | 6/2013 | Yodfat et al. .................. 604/186 |
| 2002/0040208 | A1 | 4/2002 | Flaherty et al. |
| 2005/0182385 | A1 | 8/2005 | Epley |
| 2007/0106218 | A1 | 5/2007 | Yodfat et al. |
| 2010/0137695 | A1 | 6/2010 | Yodfat et al. |

FOREIGN PATENT DOCUMENTS

| | | |
|---|---|---|
| WO | WO-2008078318 A2 | 7/2008 |
| WO | WO-2008122983 A1 | 10/2008 |
| WO | WO-2009001346 A1 | 12/2008 |

OTHER PUBLICATIONS

International Search Report for PCT Application No. PCT/IL2008/001058, mailed Mar. 20, 2009.
Nathan et al., "Intensive Diabetes Treatment and Cardiovascular Disease in Patients with Type 1 Diabetes", *N.E. J. Med.*, 353(25):2643-2653 (2005).
Ratner, R. E., "Adjunctive Therapy with the Amylin Analogue Pramlintide Leads to a Combined Improvement in Glycemic and Weight Control in Insulin-Treated Subjects with Type 2 Diabetes", *Diabetes Tech. Therapy*, 4(1):51-61 (2002).
UKPDS Group Trial, "Tight blood pressure control and risk of macrovascular and microvascular complications in type 2 diabetes: UKPDS 38", *BMJ*, 314:703-713 (1998).
UKPDS Trial, "Intensive blood-glucose control with sulphonylureas or insulin compared with conventional treatment and risk of complications in patients with type 2 diabetes (UKPDS 33)", *Lancet*, 352:837-853 (1998).
White et al., "Clarifying the Role of Insulin in Type 2 Diabetes Management", Clinical Diabetes 21:14-21 (2003).
Written Opinion of the International Search Authority for PCT Application No. PCT/IL2008/001058, mailed Mar. 20, 2009.

* cited by examiner

DEVICE FOR DRUG DELIVERY

CROSS-REFERENCE TO RELATED APPLICATIONS

The present application is a continuation of U.S. Pat. No. 8,465,460 issued on 18 Jun. 2013 (application Ser. No. 12/1733,009, filed on 20 Apr. 2010), which is a 35 U.S.C. §371 national stage entry of PCT/IL2008/001058, which has an international filing date of 31 Jul. 2008 and claims priority to U.S. Provisional Patent Application No. 60/963,071, filed on 1 Aug. 2007 and U.S. Provisional Patent Application No. 61/003,169, filed on 14 Nov. 2007. The present application incorporates herein by reference the contents of each of the above-referenced applications in their entireties.

FIELD OF THE INVENTION

The present disclosure generally relates to a device for medical infusion of fluids (e.g., drugs). In particular, the disclosure relates to a portable infusion device for delivery of an injectable therapeutic fluid. Even more particularly, the disclosure relates to a portable, manually-powered, skin-securable, injectable drug dispensing device.

BACKGROUND OF THE INVENTION

External Infusion Pump

An external infusion pump may be medically necessary for the administration of various medications, intravenously or subcutaneously. Such external infusion devices are used when parenteral administration of the drug at home is reasonable and/or necessary, when it is required that an infusion pump safely administers the drug, and/or when the drug is administered by a prolonged infusion (e.g., during at least 8 hours) because of proven clinical efficacy.

External infusion pumps ("EIP") can be used, particularly in a non-hospital setting, to administer antibiotics, chemotherapy, analgesics and opioids, total parenteral nutrition formulas, insulin, vasopressors, blood products, growth hormone, gonadotropin releasing hormone (GnRH), interferon γ, and other drugs or biologics for which delivery at a controlled rate of the fluid is desirable or necessary. Functional EIP infusion rates range from high volume delivery rates (400 mL/h) for hydration therapy to very low flow rates (0.04 mL/h) that can be used for delivery chemotherapeutic agents.

Diabetes and Glycemic Control

The term Diabetes mellitus ("DM") refers to a group of common metabolic disorders that share the phenotype of hyperglycemia. Several distinct types of DM exist and are caused by complex interaction of genetics, environmental factors, and life-style. The metabolic dysregulation associated with all types of DM, especially when glucose levels are uncontrolled, causes secondary pathophysiologic changes in multiple organ systems that impose a tremendous burden on the individual with diabetes and on the health care system. In the United States, DM is the leading cause of end-stage renal disease (ESRD), nontraumatic lower extremity amputations, and adult blindness. With an increasing incidence worldwide, DM will be a leading cause of morbidity and mortality for the foreseeable future.

The two broad categories of DM are designated type 1 and type 2. Generally speaking, type 1 DM results from autoimmune beta cell destruction, whereas type 2 DM is a heterogeneous group of disorders characterized by variable degrees of insulin resistance, impaired insulin secretion, and increased glucose production.

Type 1 DM

Type 1 DM develops as a result of the synergistic effects of genetic, environmental, and immunologic factors that ultimately destroy the pancreatic beta cells. Individuals with a genetic susceptibility have normal beta cell mass at birth but begin to lose beta cells secondary to autoimmune destruction that occurs over months to years. As beta cell mass begins to decline, insulin secretion becomes progressively impaired. Features of diabetes generally do not become evident until a majority of beta cells are destroyed (~80%).

Because individuals with type 1 DM lack endogenous insulin production, administration of basal, exogenous insulin is essential for regulating glycogen breakdown, gluconeogenesis, lipolysis, and ketogenesis. Likewise, insulin replacement for meals should be appropriate for the carbohydrate intake and promote normal glucose utilization and storage. A goal of intensive diabetes management is to achieve euglycemia or near-normal glycemia. This approach requires insulin regimen that matches glucose intake and insulin dose. Insulin regimens usually include multiple-component insulin regimens, multiple daily injections (MDI), or insulin infusion devices (Harrison's principles of internal medicine, 16th edition, chapter 323).

The benefits of intensive diabetes management and improved glycemic control has been shown in the Diabetes Control and Complications Trial (DCCT) that demonstrated that development and progression of the chronic complications of diabetes are greatly related to the degree of altered glycemia as quantified by determinations of glycohemoglobin (HbA1c). [DCCT Trial, N. Engl. J. Med, 1993; 329: 977-986, UKPDS Trial, Lancet 1998; 352: 837-853. BMJ 1998; 317, (7160): 703-13 and the EDIC Trial, N. Engl. S. Med. 2005; 353, (25): 2643-53].

In all MDI regimens, intermediate—or long-acting insulins (e.g., NPH, lente, ultralente, or glargine insulin) supply basal insulin, whereas short acting insulin (e., regular, insulin aspart, or lispro insulin) provides prandial insulin. Lispro and insulin aspart should be injected just before or just after a meal; regular insulin dosages are given 30 to 45 min prior to a meal. No insulin MDI regimen reproduces the precise insulin secretory pattern of the pancreatic islet. However, the most physiologic regimens entail more frequent insulin injections, greater reliance on short-acting insulin, and more frequent capillary plasma glucose measurements (Harrison's Principles of Internal Medicine, 16th edition, chapter 323).

In recent years, ambulatory portable insulin infusion pumps have emerged as a superior alternative to multiple daily injections of insulin. These pumps, which deliver insulin at a continuous or periodic basal rate, as well as in bolus volumes, were developed to liberate patients from repeated self-administered injections, and allow greater flexibility in dose administration. The insulin infused via the insulin pump is usually a short acting insulin (e.g., insulin aspart, lispro insulin).

Currently, about 80% of Type 1 DM patients are managed with MDI, whereas only about 20% are managed with insulin pumps.

Type 2 DM

Type 2 DM is characterized by impaired insulin secretion, peripheral insulin resistance, and excessive hepatic glucose production. Obesity, particularly visceral or central is very common in type 2 DM.

Insulin resistance can be defined as a decreased ability of insulin to act effectively on peripheral target tissues (especially muscle and liver). In the early stages of the disorder, glucose tolerance remains normal, despite insulin resistance, because the pancreatic beta cells compensate by increasing insulin output. As insulin resistance and compensatory hyperinsulinemia progress, the pancreatic islets are unable to sustain the hyperinsulinemic state. Impaired Glucose Tolerance (IGT), characterized by elevations in postprandial glucose, then develops. A further decline in insulin secretion and an increase in hepatic glucose production may lead to overt diabetes with fasting hyperglycemia. Ultimately, beta cell failure may ensue.

Increased hepatic glucose production in Type 2 DM may be due to the failure of hyperinsulinemia to suppress gluconeogenesis in the liver as a result of the insulin resistance. Type 2 DM management can begin with medical nutritional therapy ("MNT") and increased physical activity. If not sufficient to achieve glycemic control, pharmacologic therapy is indicated. Pharmacologic approaches to the management of type 2 DM include the administration of both oral glucose-lowering agents and insulin. Usually oral drugs are initiated first.

Several types of oral glucose-lowering agents that target different pathophysiologic processes in Type 2 DM exist. These include agents that increase insulin secretion (e.g., sulfonylurea), reduce glucose production (e.g., metformin), decrease glucose absorption (e.g., acarbose) and/or increase insulin sensitivity (e.g., pioglitazone).

Insulin Therapy can be considered as the initial therapy in situations involving, for example, lean individuals or individual experiencing severe weight loss, situations involving individuals with underlying renal or hepatic disease that precludes oral glucose-lowering agents, or in situations involving individuals who are hospitalized or acutely ill. Insulin therapy is ultimately required by a substantial number of individuals with Type 2 DM because of the progressive nature of the disorder and the relative insulin deficiency that develops in patients with long-standing diabetes. (Harrison's Principles of Internal Medicine, 16th edition, chapter 323).

The United Kingdom Prospective Diabetes Study (UKPDS), one of the largest and longest trial ever conducted in patients with type 2 diabetes, found that for each 1% reduction in hemoglobin A1C, there was a significant decrease in diabetic complications. (BMJ 1995; 310(6972): 83-8). A decline in MC was best achieved by early exogenous insulin therapy.

Despite the increased risk of mild hypoglycemia, aggressive therapy that combines patient education and self-management with a form of exogenous insulin that closely mimics normal insulin secretion can help to reduce the morbidity and mortality associated with type 2 diabetes. (Clinical Diabetes 2003; 21:14-21).

Pramlintide Acetate (Symlin)

Amylin is a second β-cell hormone that is co-localized and co-secreted with insulin in response to meals. Consequently, β-cell dysfunction in insulin-requiring subjects with type 1 or type 2 diabetes is characterized by a markedly impaired postprandial secretory response of both insulin and amylin. Amylin acts as a neuroendocrine hormone that complements the effects of insulin in postprandial glucose regulation through several centrally mediated effects. These include a suppression of postprandial glucagon secretion and a vagus-mediated regulation of gastric emptying, thereby helping to control the influx of endogenous and exogenous glucose, respectively. Amylin has also been shown to reduce food intake and body weight, consistent with an additional satiety effect. Consistent with these findings, mealtime amylin replacement, as an adjunctive therapy to insulin, may improve metabolic control in diabetic subjects.

Pramlintide is a soluble, non-aggregating synthetic peptide analog of human amylin that has a potency at least equal to that of native amylin. Pramlintide in insulin-requiring subjects with diabetes has been shown, as an adjunct to insulin therapy, to correct postprandial hyperglucagonemia, slow the delivery of nutrients from the stomach to the small intestine, and, concomitantly, improve postprandial glucose excursions, (Diab, Tech. Therp. 2002; 4(1):51-61). Pramlintide is injected subcutaneously with a standard insulin syringe, rendering the dosage flexible.

Exentide

Incretins are gut-derived factors that increase glucose stimulated insulin secretion. Exentide (byetta) is an incretin mimetic that increases insulin secretion, increase beta cell growth/replication, slows gastric emptying, and may decrease food intake. Exentide is indicated as an adjunctive therapy to improve glycemic control in type 2 diabetic patients who are taking one or more of the following oral anti-diabetic drugs: Metformin, sulfonylurea, thiazolidinedione. Exentide is administered before a meal as a subcutaneous injection.

Insulin Pumps

Currently available insulin pumps, developed mainly for type 1 DM patients, deliver rapid acting insulin 24 hours-a-day through a catheter placed under the skin (i.e., subcutaneously). The total daily insulin dose can be divided into basal and bolus doses.

Basal insulin is delivered continuously over 24 hours, and keeps the blood glucose concentration levels (in brief blood glucose levels) in normal desirable range between meals and overnight. Basal insulin delivery rate can be changed during the day to counteract changing diurnal insulin requirements, for example during physical activity, sleeping, etc. Moreover, a specific daily basal administration curve can be stored (designated as a "basal profile") and retrieved upon patient discretion.

Insulin bolus doses are delivered before or after meals to counteract carbohydrates loads or during episodes of high blood glucose concentration levels. Current pumps contain electronic components and are provided with the necessary software to precisely calculate bolus doses according to meal size and carbohydrate content.

Due to the fact that Type 2 DM patients usually have some residual endogenous insulin, the basal/bolus administration mode of currently existing pumps is unnecessary, for the following reasons:

1. Most patients have enough insulin to sustain the basal requirements of the body but not to counteract the carbohydrates consumed in meals.
2. Basal requirements are usually met by a single long acting insulin injection per day (i.e., Glargine, Detemir).
3. Precise bolus dosing is of no clinical relevance because the amount of residual endogenous insulin and insulin resistance are unknown,
4. Conventional insulin pumps are costly, particularly because they include relatively expensive electronic components which are mainly used to control basal administration.

For these reasons, DM type 2 patients tend not to use insulin pumps.

Under some circumstances, conventional insulin pumps, although developed primarily for Type 1 DM patients, may not be appropriate for all Type 1 DM patients, for the following reasons:

1. The underlying technology involved makes currently available pumps relatively expensive and therefore not adequate for low budget patients.
2. The underlying technological sophistication of currently available pumps require learning of the many installed features, an endeavor that makes many individuals uncomfortable with the use of these devices (i.e., fear of technology).

3. A major drawback of currently available pumps is their large size and weight, caused in part by numerous electronic components and the relatively large driving mechanism of these devices. These uncomfortable bulky fluid delivery devices are rejected by many diabetic insulin users.

SUMMARY OF THE INVENTION

Disclosed herein is a dispensing device which obviates the problems of conventional infusion devices and provides an improved device which is easy to use, affordable and operationally intuitive for diabetic patients.

In some embodiments, a portable device for bolus(es) delivery of injectable therapeutic fluid into the body of the patient at the patient's discretion is provided.

In some embodiments, a device for delivery of one or more anti-diabetic injectable drug bolus(es) to the body to achieve better glycemic control is described.

In some embodiments, a device that is miniature, discreet, user-friendly, economical for users and cost-effective for the payer that can deliver injectable drugs into the body of the patient is provided. The device can be configured to include a durable reusable part that contains the relatively expensive component(s) (e.g., a driving mechanism), and a disposable part to house the relatively cheaper components (e.g., a reservoir).

In some embodiments, a device that includes a miniature patch unit that can be secured to the skin and can deliver injectable drugs (e.g., in bolus doses) into the body is described. In some embodiments, bolus dose(s) adjustments and/or administrations can be done manually. In some embodiments, such adjustments and/or administrations can be done automatically and/or periodically, or be based on any desired schedule (e.g., scheduling profiles stored in a storage device that can be accessed by a controller and/or the user). In some embodiments, a device that can be easily connected and disconnected from a subcutaneous cannula is provided.

In some embodiments, the dispensing device includes two parts: a disposable part and a reusable part. The disposable part includes a reservoir intended to be filled with some therapeutic fluid (e.g., insulin) and an outlet port through which the fluid is transferred to the patient's body. The reusable part includes a driving mechanism and/or a pumping mechanism. The dispensing device may be operable upon connection of the two parts.

In some embodiments, neither the disposable part nor the reusable part includes electronic to enable low production cost and, as a result, a financially affordable device for DM: patients. Such devices may include a manually-power pumping mechanism and a power transfer mechanism to transfer manually-generated power provided by a user.

In some embodiments, the pumping mechanism may be a peristaltic-type mechanism, a piston-based mechanism, etc.

In some embodiments, the device is manually operable (e.g., manually-powered) and the power transfer mechanism (also referred to as a driving mechanism) includes mechanical components (e.g., springs, gears, etc.) and is implemented without components requiring electrically-generated power and/or without any electronic components (e.g., CPU, electronically-controlled sensors).

In some embodiments, operation of the device is relatively easy and simple, and includes, for example, pressing (actuating) of buttons or of a blower. Operating the disclosed device does not require any specialized skills, technical support and/or training, thus enabling operation of such device by patients who are less adept technologically, or who are otherwise apprehensive about dealing with complicated software or electronic device and/or applications.

Further embodiments described herein include a controller to monitor the amount of the dispensed therapeutic fluid and the fluid remaining in the reservoir. In some embodiments, an indicator, such as, for example, a detachable digital counter, enables the display of operational parameters (e.g., number of units delivered). In some embodiments, the indicator is cost-effective and requires a simple electric circuit.

In some embodiments, the reservoir holding the therapeutic fluid and housed within the device may be configured in various sizes to hold different volumes of therapeutic fluid.

In some embodiments, the reservoir holding the therapeutic fluid and housed within the device may be configured to hold different types of therapeutic fluid to enable delivery of various therapeutic fluids at the patient's discretion.

In one aspect, an ambulatory therapeutic fluid delivery device is disclosed. The device includes at least one housing connectable to a cannula, the at least one housing retaining a reservoir to hold the therapeutic fluid. The device also includes a mechanically powered pumping mechanism to cause delivery of at least some of the fluid from the reservoir, and a power-transfer mechanism to transfer manually-delivered power provided by a user to mechanically actuate the pumping mechanism.

Embodiments of the device may include one or more of the following features.

The device may further include a subcutaneously insertable cannula in fluid communication with the reservoir.

The device may be skin adherable.

The reservoir may be tillable by the user.

The mechanically-powered pumping mechanism may be configured to operate without using electrically-generated power.

The therapeutic fluid may includes one or more of, for example, insulin, Pramlintide acetate and/or Exentide (also referred as Exenatide, which is commercially known as BYETTA™).

The at least one housing may include a disposable part housing including at least a part of the reservoir and an outlet port to enable passage of the fluid to a body of the patient, and a reusable part housing attachable to the disposable part, the reusable part housing including at least the pumping mechanism and the power-transfer mechanism. The reservoir may be configured to be filled with the fluid prior to attachment of the disposable part to the reusable part.

The power-transfer mechanism may include a user-actuated rotateable wheel, and one or more gears coupled to the rotateable wheel and further coupled to the mechanically-powered pumping mechanism., the one or more gears configured to actuate the pumping mechanism to cause the delivery of the at least some of the fluid in response to rotation of the user-actuated wheel. The one or more gears may include at least one cog wheel in mechanical communication with at least one worm gear, and a screw-nut coupled to the worm gear and further coupled to a piston such that rotation of the screw nut causes displacement of the piston.

The mechanically-powered pumping mechanism may include a piston coupled to the reservoir, the piston further coupled to the power-transfer mechanism. Actuation of the piston by the power-transfer mechanism may cause displacement of the piston such that the piston causes at least some of the fluid in the reservoir to be displaced.

The device may further include a handle coupled to the piston to enable manual displacement of the piston. The device may further include a limiter to prevent displacement of the piston beyond a pre-set spatial position defined by the limiter. The limiter may include a stationary block to engage a projection extending from an end of the piston such that upon contact between the stationary block and the projection extending from the end of the piston, further displacement of the piston is prevented.

The pumping mechanism may include a peristaltic-type pumping mechanism. The peristaltic-type pumping mechanism may include a rotor coupled to a delivery tube to deliver therapeutic fluid, the rotor further coupled to the power-transfer mechanism such that manual power transferred by the power-transfer mechanism causes rotation of the rotor to cause displacement of therapeutic fluid contained within the delivery tube.

The power-transfer mechanism may include a spring-based mechanism actuated by the user, the spring-based mechanism configured to actuate the pumping mechanism upon actuation of the spring-based mechanism by the user. The spring-based mechanism may include a spiral spring coupled to at least one gear, the spiral spring biased in a first rotational direction, and a string coupled to the spiral spring to cause rotation of the spiral spring in another rotational direction to cause an increase in the tension of the spiral spring. Upon release of the string, the spiral spring may rotate in the first rotational direction to cause actuation of the power-transfer mechanism coupled to the spiral spring. The string may be configured to be moved to a position such that upon release of the string the spiral spring rotates a pre-defined radial distance that causes actuation of the pumping mechanism by an amount corresponding to delivery of a pre-determined amount of therapeutic fluid.

The pumping mechanism may include an inflatable air container to actuate the reservoir. The power-transfer mechanism may include at least one air injection device to deliver air to the inflatable air container. The at least one air injection device may include an air tube in communication with the inflatable air container, and an air compression chamber in communication with the air tube, the air compression chamber including a displaceable plunger. Upon actuation of the plunger by the user, air may be displaced from the air compression chamber into the inflatable air container through the air tube.

The device may further include an indicator to indicate operation of the mechanically powered pumping mechanism. The indicator may include one or more of, for example, an audible indicator to produce a sound and/or a visual indicator to produce a visual signal.

The device may further include a counter to display a value representative of an amount of therapeutic fluid delivered and/or to be delivered by operation of the device. The counter may be configured to indicate delivery of discrete bolus doses of the fluid from the reservoir. The counter may be configured to display units representative of the amount of delivered therapeutic fluid, each of the displayed unit representative of a pre-defined amount of the delivered therapeutic fluid. Operation of the counter may be based on operation of the power-transfer mechanism. Operation of the counter may be based on the operation of the power-transfer mechanism such that the power transfer mechanism actuates the counter. The counter may include a mechanically detachable counter housing configured to be attached and detached from the at least one housing.

The device may further include a measurement unit to determine extent of fluid delivered. The measurement unit may include an optical unit to detect one or more markings disposed on the power-transfer mechanism. The detection of the one or more markings may be indicative that a pre-determined amount of fluid was delivered. The power transfer mechanism may include a gear having one or more holes extending from one surface of the gear to the other surface. The optical unit may include a light source to illuminate a light beam towards the one surface of the gear, and a light sensor to detect light passing through the one or more holes.

The device may further include a cradle unit configured to receive the at least one housing retaining the reservoir, the cradle unit being securable to skin of a patient. The cradle unit may include an adhesive surface configured to be adhered to the skin of a patient, at least one latch configured to secure the at least one housing to the cradle unit, and a well to enable passage of the cannula therethrough. The device may further include a cannula cartridge unit, and the cannula may be subcutaneously insertable from the cannula cartridge unit through the cradle unit.

The device may further include an adapter connectable to the reservoir and further connectable to a refilling vial containing therapeutic fluid to be added to the reservoir.

The at least one housing may be configured to receive different size reservoirs.

In another aspect, an ambulatory therapeutic fluid delivery device is disclosed. The device includes at least one housing connectable to a cannula, the at least one housing retaining a reservoir to hold the therapeutic fluid. The device also includes a piston coupled to the reservoir, and a power-transfer mechanism to transfer manually-delivered power provided by a user to mechanically actuate the piston. Actuation of the piston by the power-transfer mechanism causes displacement of the piston such that the piston causes at least some of the fluid in the reservoir to be displaced.

Embodiments of the device may include any of the features of the first device described above.

In a further aspect, an ambulatory therapeutic fluid delivery device is discloses. The device includes at least one housing connectable to a cannula, the at least one housing retaining a reservoir to hold the therapeutic fluid. The device also includes a piston coupled to the reservoir, a user-actuated rotateable wheel., and one or more gears powered by manually-delivered power generated by a user, the one or more gears coupled to the rotateable wheel and further coupled to the piston. In response to rotation of the user-actuated wheel by the user the one or more gears mechanically actuate the piston to displace the piston and cause delivery of at least some of the fluid.

Embodiments of the device may include any of the features of the devices described above.

In yet another aspect, an ambulatory therapeutic fluid delivery device is disclosed. The device includes a reservoir to hold the therapeutic fluid, a peristaltic-type pumping mechanism, and a power-transfer mechanism to transfer manually-delivered power provided by a user to mechanically actuate the peristaltic-type pumping mechanism. Actuation of the peristaltic-type pumping mechanism by the power-transfer mechanism causes movement of the peristaltic-type pumping mechanism such that the peristaltic-type pumping mechanism causes at least some of the therapeutic to be displaced.

Embodiments of the device may include any of the features of the devices described above.

In another aspect, an ambulatory therapeutic fluid delivery device is disclosed. The device includes a reservoir to hold the therapeutic fluid, a rotor coupled to a delivery tube to deliver some of the therapeutic fluid, a user-actuated rotateable wheel, and one or more gears powered by manually-delivered power generated by a user, the one or more gears coupled to the rotateable wheel and further coupled to the rotor. In response to rotation of the user-actuated wheel by the user the one or more gears mechanically actuate the rotor to cause displacement of fluid contained in the delivery tube.

Embodiments of the device may include any of the features of the devices described above.

In a further aspect, an ambulatory therapeutic fluid delivery device is disclosed. The device includes a reservoir to hold the therapeutic fluid, an inflatable air container to actuate the reservoir, and at least one manually-actuated air injection device to deliver air to the inflatable air container. Inflation of the air container causes at least some of the fluid in the reservoir to be displaced.

Embodiments of the device may include any of the features of the devices described above.

In yet another aspect, a method to administer therapeutic fluid held in a reservoir is disclosed. The method includes transferring manually-generated power provided by a user to a mechanically-powered pumping mechanism disposed in at least one housing connectable to a cannula, the at least one housing further retaining the reservoir. The method further includes mechanically actuating the pumping mechanism to cause delivery of at least some of the therapeutic fluid.

Embodiments of the method may include any of the features of the devices described above, as well as one or more of the following features.

Actuating the pumping mechanism may include actuating the pumping mechanism without using electrically-generated power.

Transferring the manually-generated power may include rotating a user-actuated rotateable wheel, and causing actuation of one or more gears coupled to the rotateable wheel in response to rotation of the rotateable wheel to cause actuation of the mechanically-powered pumping mechanism. The one or more gears may include at least one cog wheel in mechanical communication with at least one worm gear, and a screw-nut coupled to the worm gear and further coupled to a piston such that rotation of the screw nut causes displacement of the piston.

Actuating the pumping mechanism may include actuating a piston coupled to the reservoir, the piston further coupled to the power-transfer mechanism, and displacing the at least some of the fluid in response to actuation of the piston by the power-transfer mechanism.

The method may further include displaying a value representative of an amount of therapeutic fluid delivered. Displaying the value may include displaying a value indicative of delivery of discrete bolus doses of the fluid from the reservoir. Displaying the value may includes displaying the value representative of an amount of therapeutic fluid delivered based on extent of the manually generated power provided by the user.

The method may further include determining extent of fluid delivered. Determining the extent of the fluid delivered may include detecting one or more markings disposed on a power-transfer mechanism to transfer the manually generated power. The detection of the one or more markings may be indicative that a pre-determined amount of fluid was delivered. Detecting the one or more markings may include illuminating a light beam towards a first surface of the power-transfer mechanism having one or more holes extending from the first surface to another surface of the power-transfer mechanism, and detecting light passing through the one ore holes.

More features and embodiments of the present inventions will be illustrated in the detailed description.

DETAILED DESCRIPTION OF DRAWINGS

Disclosed are ambulatory therapeutic fluid delivery devices and methods. A disclosed device includes at least one housing connectable to a cannula, the at least one housing retaining a reservoir to hold the therapeutic fluid, a mechanically powered pumping mechanism to cause delivery of at least some of the fluid from the reservoir, and a power-transfer mechanism (i.e., a driving mechanism) to transfer manually-delivered power provided by a user to mechanically actuate the pumping mechanism. The mechanically-powered pumping mechanism is configured to operate without using electrically-generated power. In some embodiments, the power-transfer mechanism includes a user-actuated rotateable wheel, and one or more gears coupled to the rotatable wheel and further coupled to the mechanically-powered pumping mechanism. The one or more gears are configured to actuate the pumping mechanism to cause the delivery of the at least some of the fluid in response to rotation of the user-actuated wheel. In some embodiments, the mechanically-powered pumping mechanism includes a piston coupled to the reservoir and further coupled to the power-transfer mechanism. Actuation of the piston by the power-transfer mechanism causes displacement of the piston such that the piston causes at least some of the fluid in the reservoir to be displaced. In some embodiments, the pumping mechanism includes a peristaltic-type pumping mechanism and/or an inflatable air container to actuate the reservoir. Other types of power-transfer mechanisms and/or mechanically actuated pumping mechanisms may be used.

In some embodiments, fluid infusion device described herein includes the following units:

A dispensing patch unit having a reservoir and a driving mechanism (i.e., power-transfer mechanism). The dispensing patch unit (hereinafter referred to as the "patch unit" or the "dispensing device" or the "fluid delivery device") may include one or more parts. The dispensing patch unit can be secured. (e.g., adhered) directly to the skin of the patient.

A cradle unit that is securable (e.g., adherable) to the skin of the patient and configured to enable connection and disconnection of the dispensing patch unit, A cannula cartridge unit that includes a cannula and is configured to, among other things, shield the sharp end of a penetrating member which is deployed in the cannula cartridge unit before and after insertion.

In some embodiments, the device may include a port unit. The port unit may be configured to enable connection of the dispensing device during operation of the device (e.g., delivery of a drug to the body of the patient). After completion of operation of the device, the dispensing patch unit may be disconnected from the port unit and kept away from the body of the patient.

Figure 1A:
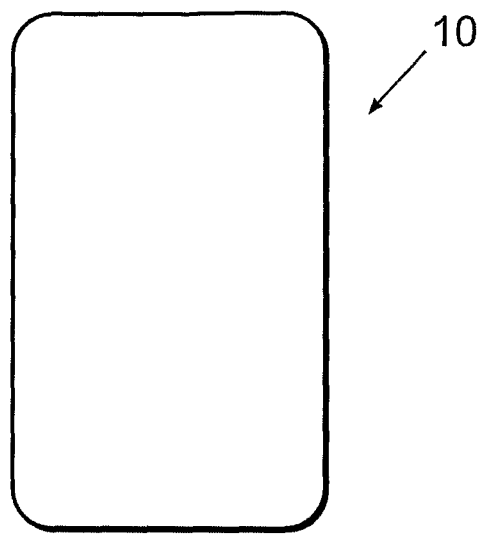
FIG. 1a is a schematic diagram of an exemplary single-part fluid delivery device.
Figure 1B:
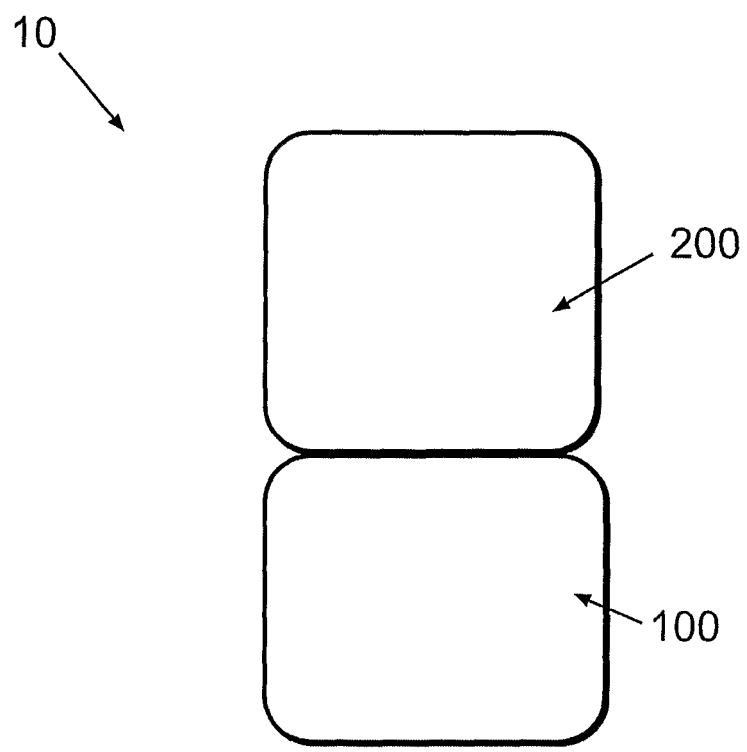
FIG. 1b is a schematic diagram of an exemplary two-part fluid delivery device.

Referring to FIGS. 1a-6c, schematic diagrams and views illustrating an exemplary fluid infusion device 10 and various exemplary configurations to attach the device 10 to the body of the patient are shown. FIG. 1a is a schematic diagram of an exemplary single-part fluid delivery device 10, FIG. 1b is a schematic diagram of an exemplary two-part fluid delivery device 10. The two-part device 10 may be configured to include a reusable part 100 and a disposable part 200. The reusable part 100 may include relatively expensive components of the device 10 such as, for example, a driving mechanism (i.e., a power transfer mechanism) to cause fluid delivery from the reservoir to the patient's body. The disposable part 200 may include the relatively cheaper and replaceable components of the device 10 such as, for example, the reservoir, cannula, etc.

Figure 2A:
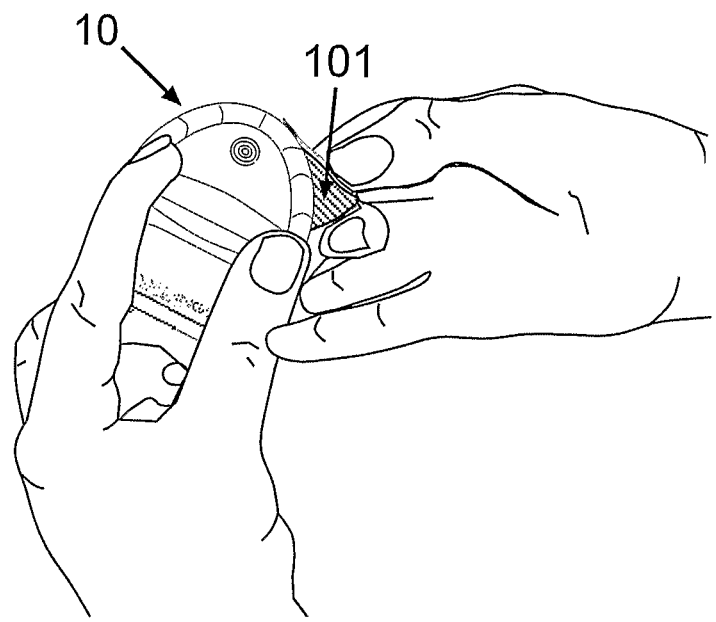
FIGS. 2a-c are views illustrating an exemplary fluid-delivery device being secured directly to the skin of the patient.
Figure 2B:
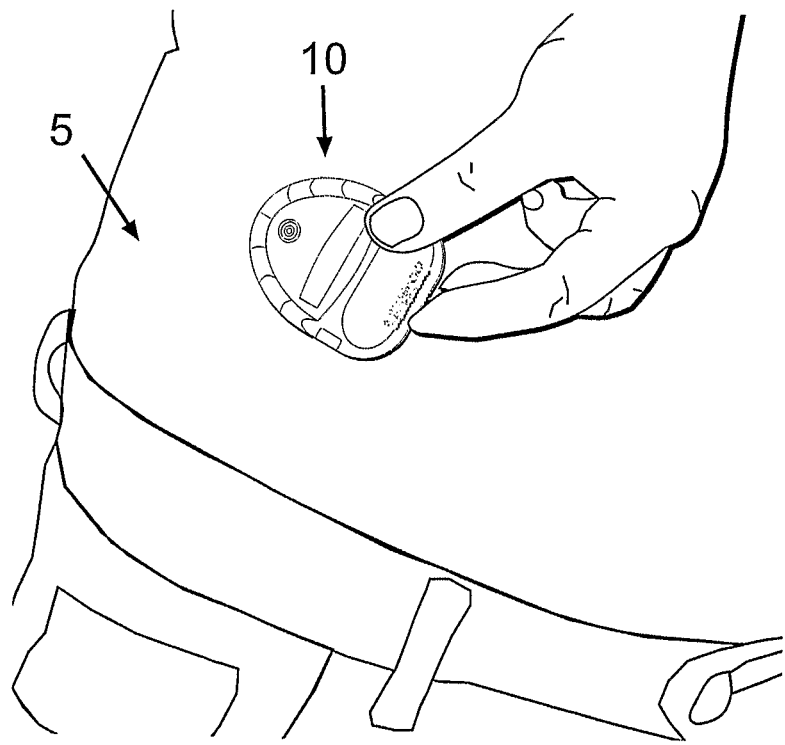
Figure 2C:
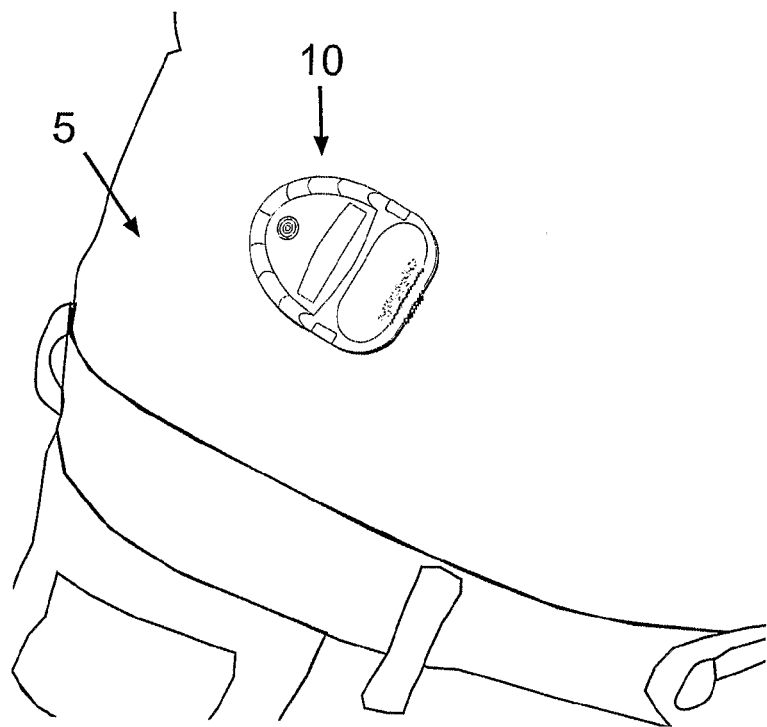

Referring to FIGS. 2a-c, views depicting exemplary ways of securing the device 10 to the skin 5 of a patient are shown. FIG. 2a illustrates removal of an adhesive protection layer 101 from the dispensing device 10. FIG. 2b illustrates securing the dispensing device 10 to the skin 5 of the patient. FIG. 2c illustrates the device 10 being secured (e.g., adhered) to the skin 5 of the patient. The device 10 may be adhered directly to the skin 5 of the patient.

Figure 3A:
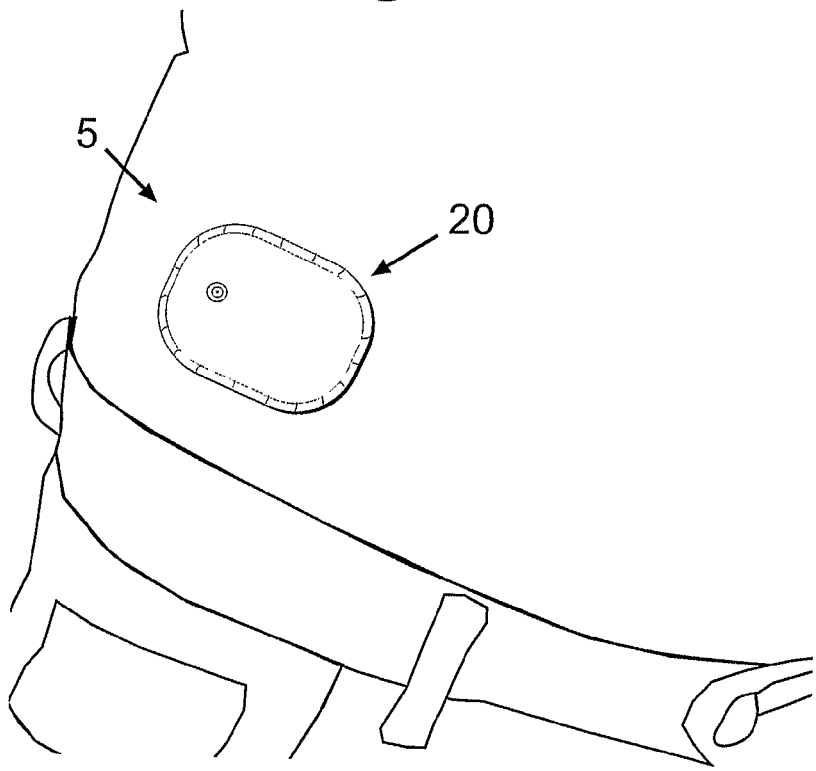
FIGS. 3a-c are views illustrating connection of an exemplary fluid delivery device to a cradle unit.
Figure 3B:
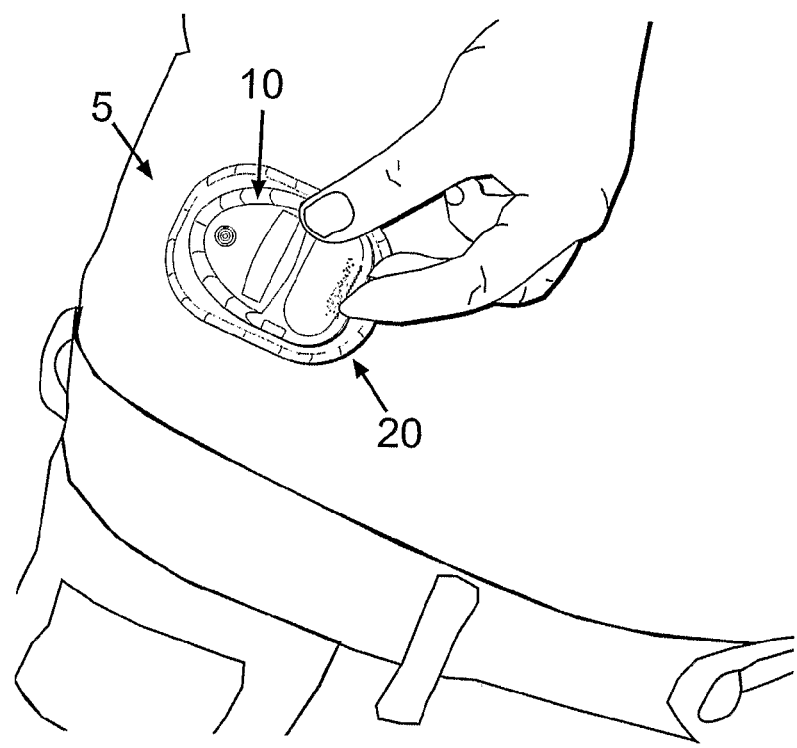
Figure 3C:
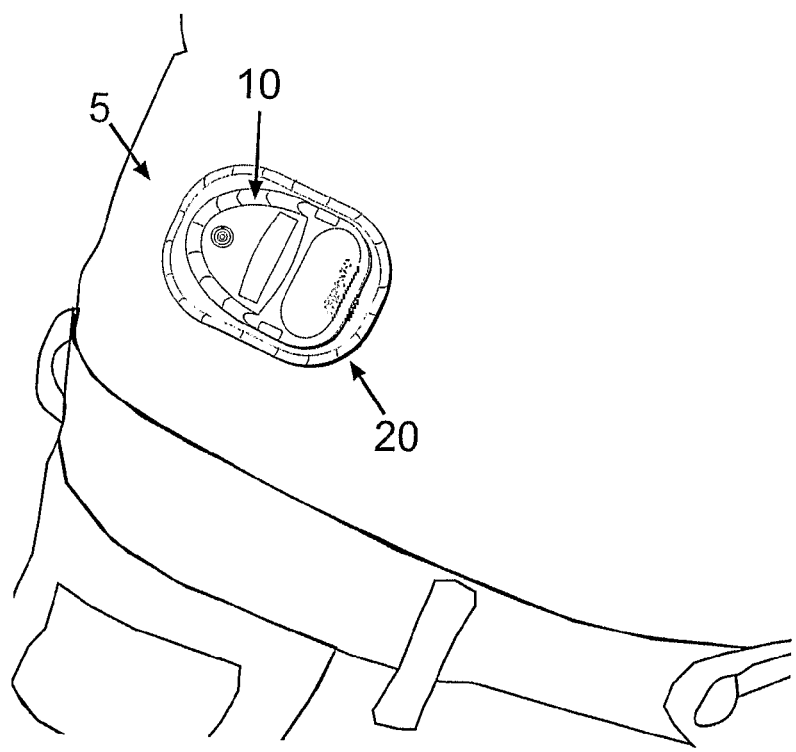

Referring to FIGS. 3a-e, views illustrating an exemplary cradle unit 20 that is secured to the skin 5 of the patient are shown. The dispensing device 10 may be connected to and disconnected from the cradle unit 20 at the patient's discretion. FIG. 3b shows exemplary connection of the dispensing device 10 to the cradle unit 20. FIG. 3c illustrates an exemplary dispensing device 10 being connected to the cradle unit 20 and ready to operate.

Figure 4A:
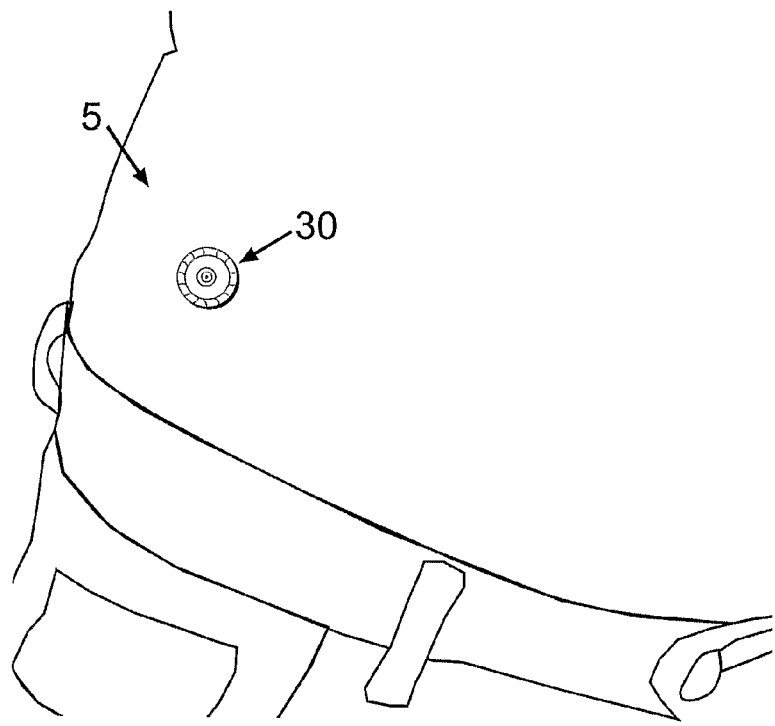
FIGS. 4a-c are views illustrating connection and disconnection of an exemplary fluid delivery device from a port unit.
Figure 4B:
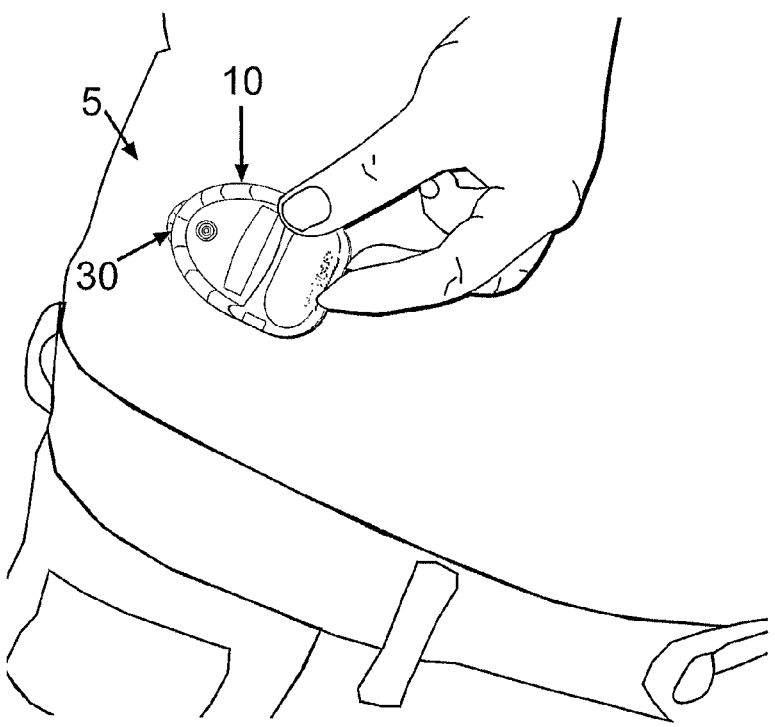
Figure 4C:
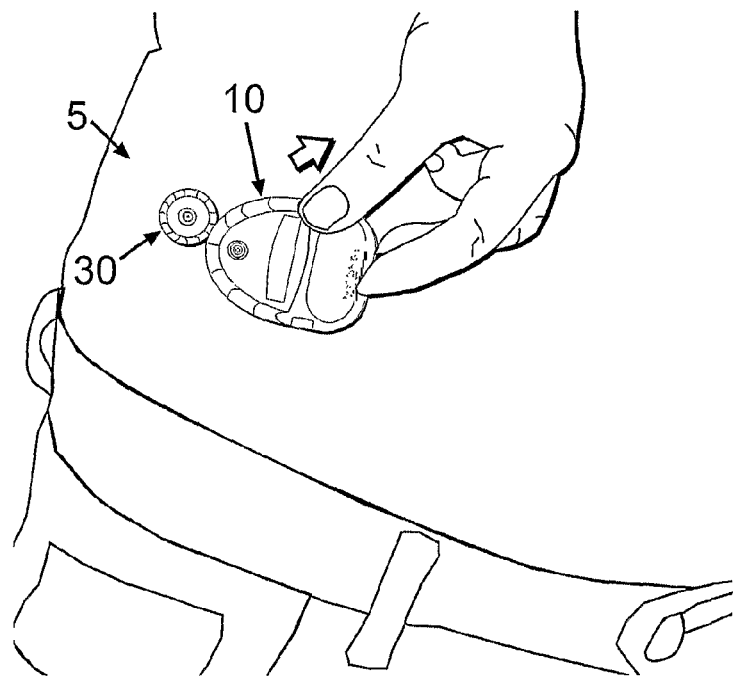

Referring to FIGS. 4a-c, views illustrating an exemplary port unit 30 secured to the skin 5 of a patient are shown. The dispensing device 10 may be connected to the port unit 30 during operation of the device 10 (e.g., during drug delivery). After completion of the drug administration, the dispensing device 10 may be disconnected from the port unit 30 and kept away from the patient. A description of port units similar to the port unit 30 are provided, for example, in co-owned U.S. Provisional Application No. 60/963,039, filed Aug. 1, 2007, and entitled "Device and Method for the Infusion of Therapeutic Fluid and Sensing of Bodily Analytes," U.S. Provisional Application No. 61/008,694, filed Dec. 21, 2007, and entitled "Device and Method for the Infusion of Therapeutic Fluid and Sensing of Bodily Analytes," as well is in co-owned non-provisional U.S. patent application entitled "Device and Method for the Infusion of Therapeutic Fluid and Sensing of Bodily Analytes," filed on the same day as the present application, the contents of all of which are hereby incorporated by reference in their entireties. The port unit 30 is configured to enable the patient/user to adhere a much smaller and less bulky item to the skin 5 instead of securing the larger cradle unit 20 to the skin 5. The port unit is coupleable to a cradle unit and/or a fluid delivery device. In some embodiments, the patient cannot leave the dispensing device 10 attached to the body when using the port unit 30. FIG. 4a illustrates the port unit 30 being adhered to the body of the patient FIG. 4b illustrates an exemplary connection of the dispensing device 10 to the port unit 30. FIG. 4c illustrates the dispensing device 10 being disconnected from the port unit 30.

Figure 5A:
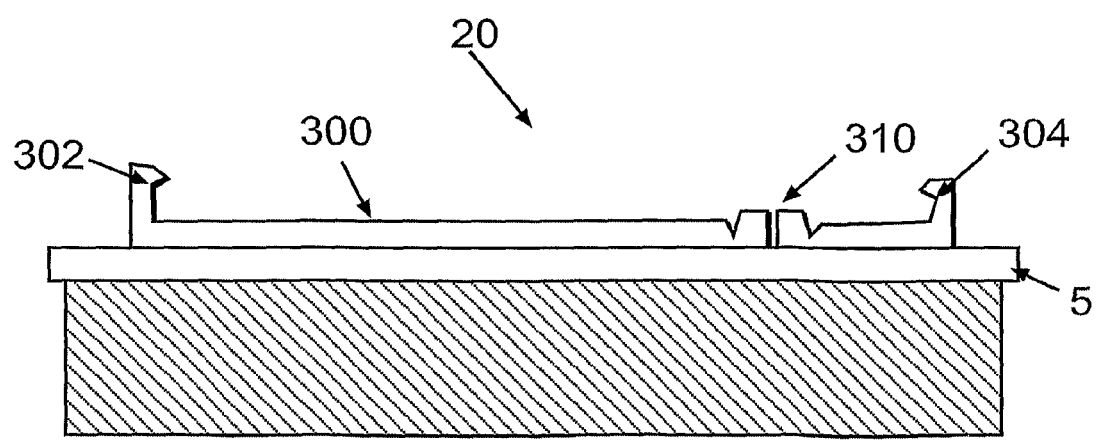
FIGS. 5a-c are schematic diagrams and views of an exemplary cradle unit.
Figure 5B:
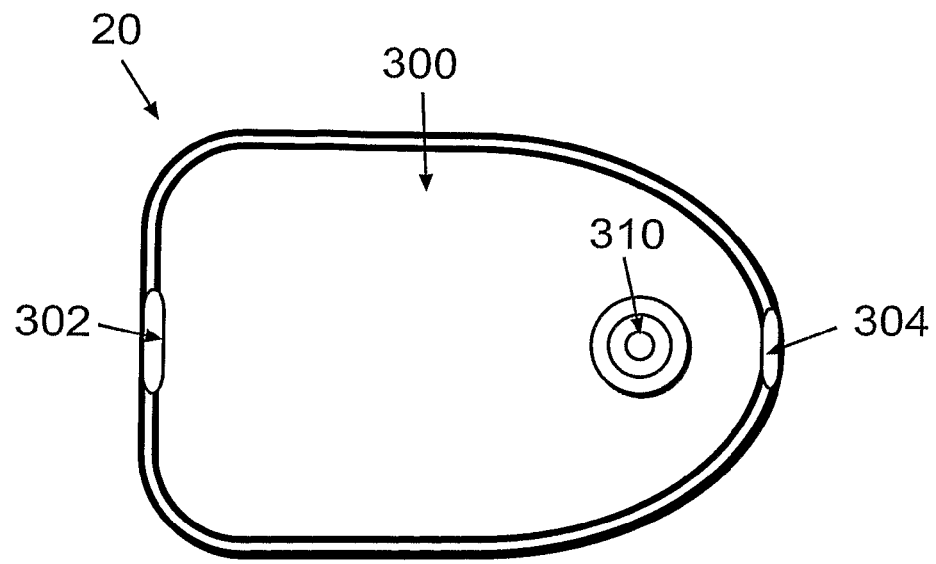
Figure 5C:
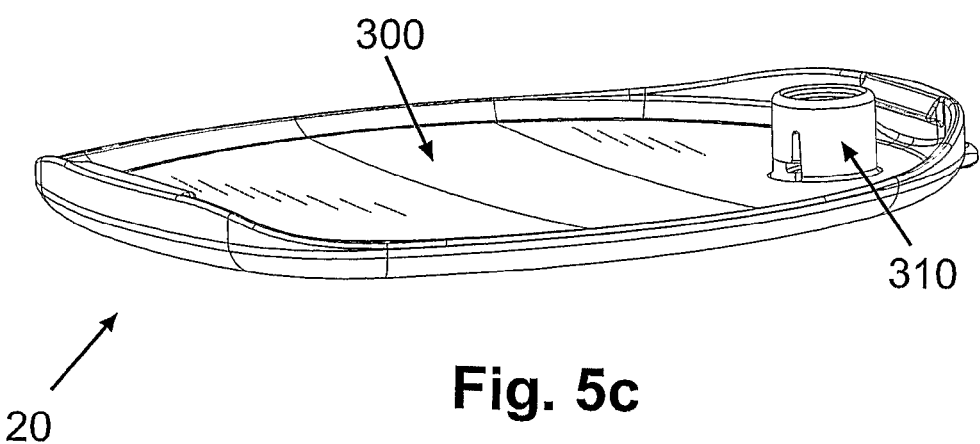

Referring to FIGS. 5a-c, schematic diagrams and views of an exemplary cradle unit 20 are shown. FIG. 5a is a cross-sectional view of the cradle unit 20 secured (e.g., adhered) to the skin 5 of the patient. The cradle unit 20 includes a flat surface 300 with an adhesive layer attached to its bottom (not shown in FIG. 5a) and latches 302 and (304) to secure a dispensing device to the cradle unit 20. The cradle unit also includes a well 310 to enable passage of a cannula (not shown in FIG. 5a) during its insertion into the skin (e.g., into the subcutaneous tissue). FIG. 5b is a top view of the cradle unit 20. FIG. 5c is an isometric view of the cradle unit 20.

Figure 6A:
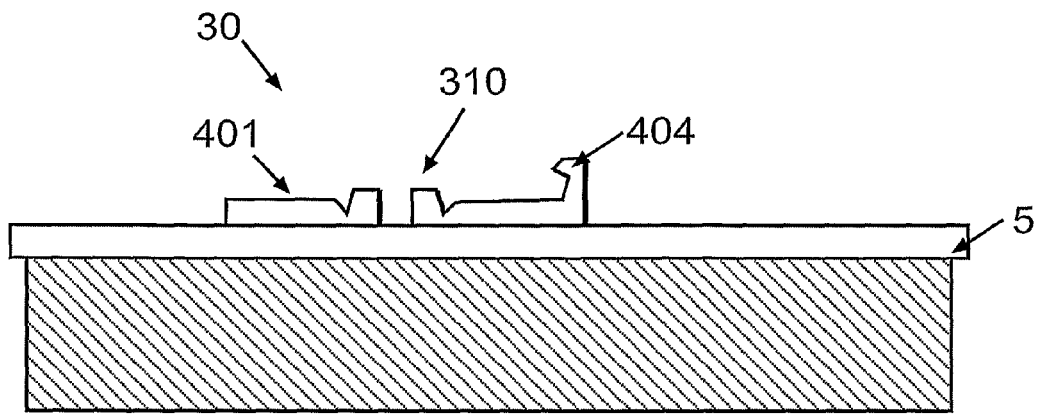
FIGS. 6a-c are schematic diagrams and views of an exemplary port unit.
Figure 6B:
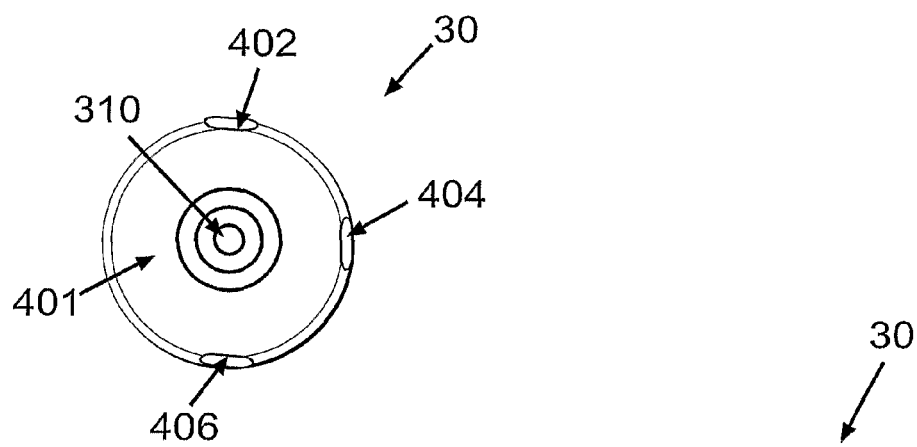
Figure 6C:
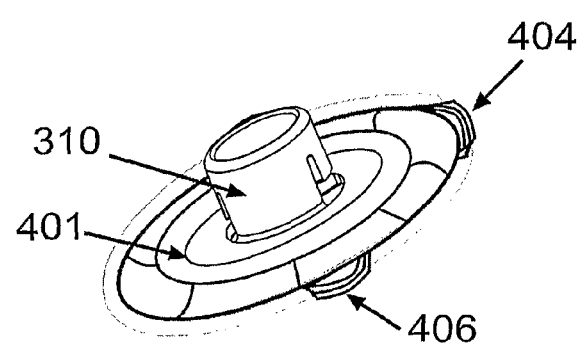

Referring to FIGS. 6a-c, diagrams of an exemplary port unit 30 are shown. FIG. 6a is a cross-sectional view of the port unit 30 being secured (e.g., adhered) to the skin 5 of the patient. FIG. 6b is a top view of the port unit 30. FIG. 6c is an isometric view of the port unit 30. The port unit 30 includes a flat surface 401 having an adhesive layer attached to its bottom (not shown in FIGS. 6a-c) and latches 402, 404 and 406 to secure the dispensing device 10 to the port unit 30. A cannula (not shown in FIGS. 6a-c) may be inserted via the well 310 using an inserter such as an inserter described, for example, in co-owned International Patent Application No. PCT/11,08/000,860, filed Jun. 25, 2008, claiming priority to U.S. Provisional Patent Application No. 60/937,214, entitled "Insertion device for inserting a cannula into a body," filed on Jun. 25, 2007, the content of which is hereby incorporated by reference in its entirety.

Referring to FIGS. 7a-9, schematics and views of an exemplary two-part dispensing patch device 10 that includes a disposable part and a reusable part are shown.

Figure 7A:
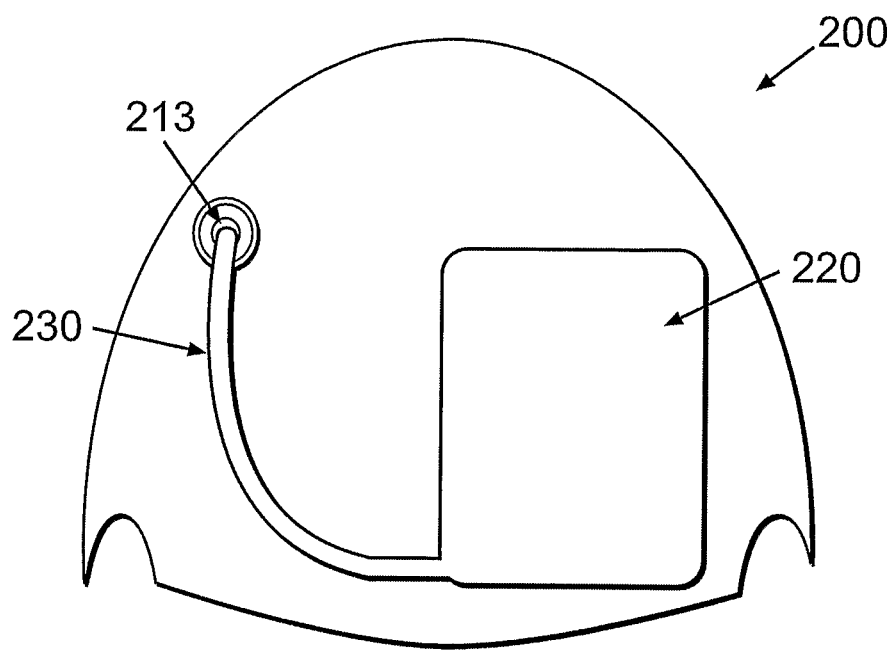
FIGS. 7a-b are schematic and isometric views of an exemplary disposable part of a fluid delivery device.
Figure 7B:
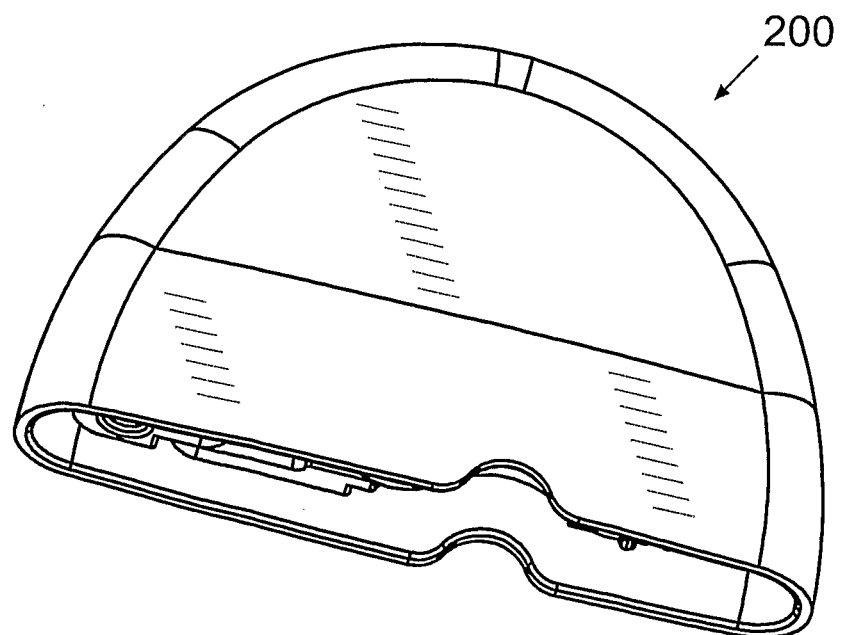

FIG. 7a illustrates an exemplary disposable part 200. The disposable part 200 includes a reservoir 220, a tube 230 and an outlet port 213 through which therapeutic fluid (e.g., insulin) can be injected to the body of the patient. FIG. 7b is an isometric view of the disposable part 200. The disposable part 200 can be configured to be replaced either at predetermined time intervals (e.g., 3 day intervals), whenever the reservoir 220 becomes empty, or automatically.

Figure 8A:
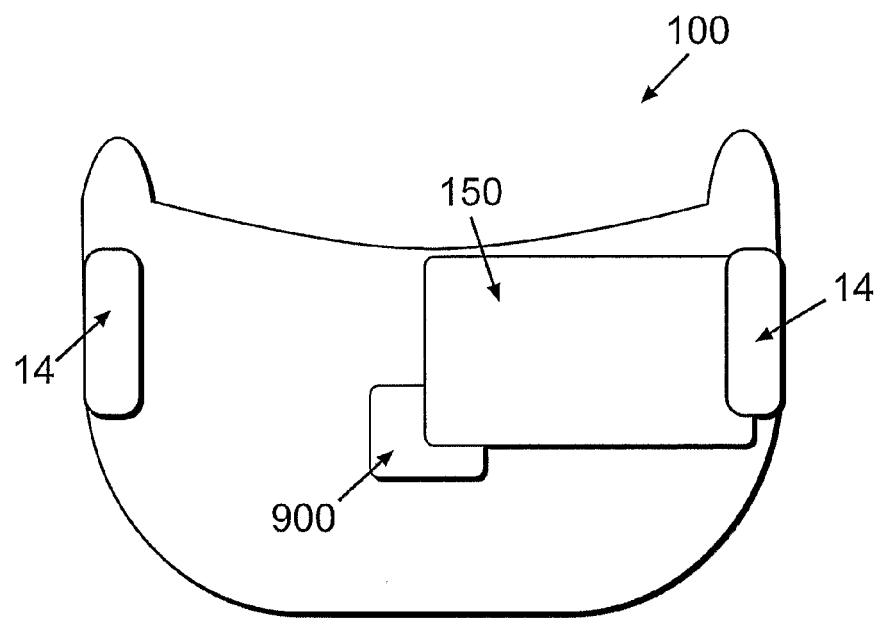
FIGS. 8a-b are schematic and isometric views of an exemplary reusable part of a fluid delivery device.
Figure 8B:
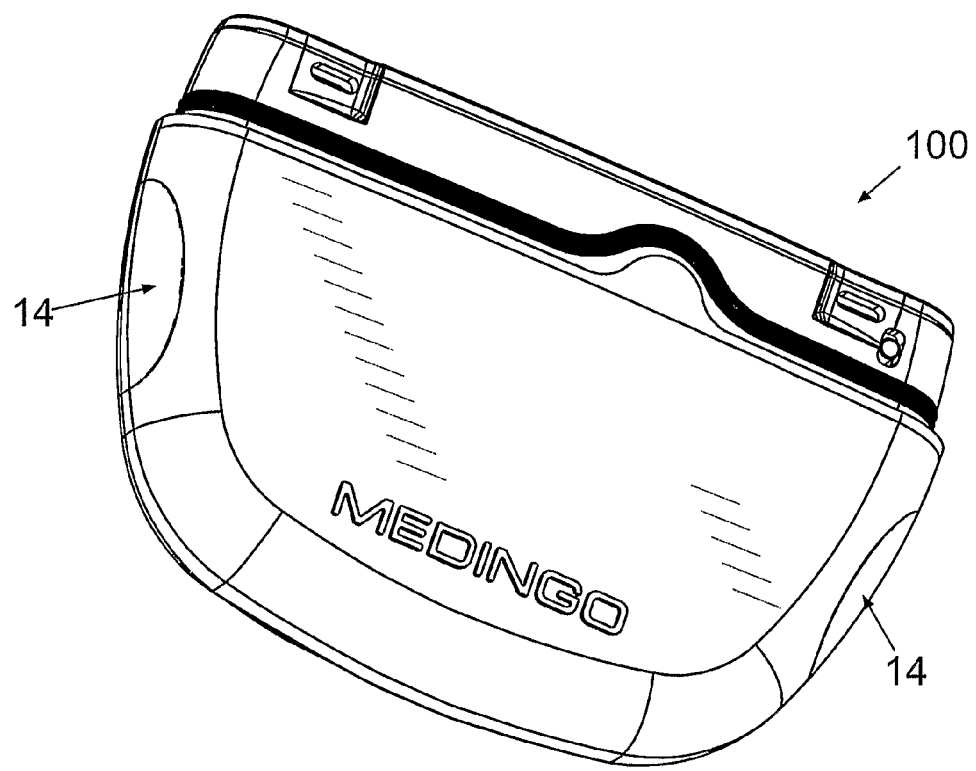

Referring to FIG. 8a, a schematic diagram of an exemplary reusable part 100 of a fluid-dispensing device is shown. The reusable part 100 includes a mechanical driving and pumping mechanism (collectively designated 150 in FIG. 8a), a counter 900 and one or more actuation units 14 to, for example, transfer manual-power provided by the user to power the driving and/or pumping mechanisms. The driving and pumping mechanism 150 may be configured as low-cost mechanisms manufactured from relatively inexpensive components. FIG. 8b is an isometric view of the reusable part 100.

Figure 9:
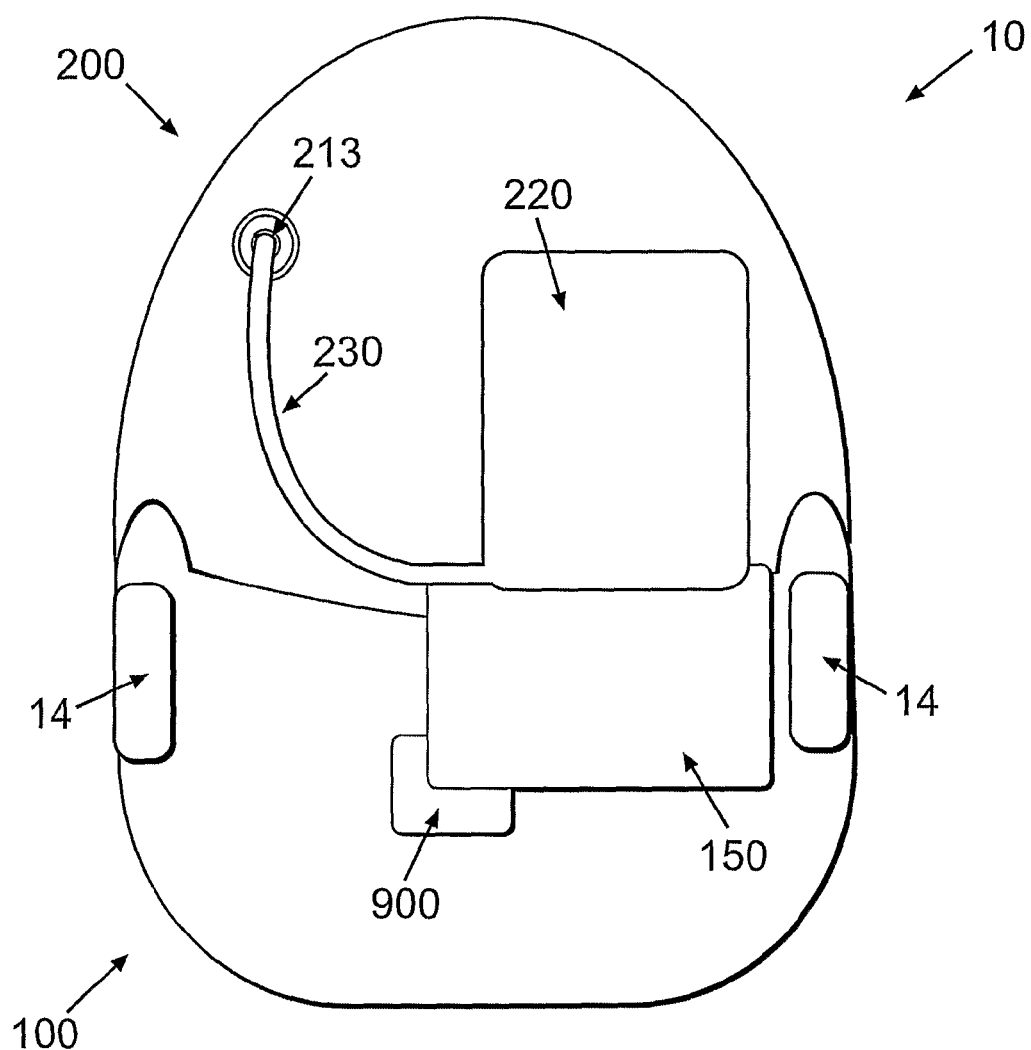
FIG. 9 is a schematic diagram of an exemplary fluid delivery device that includes a reusable part and a disposable part.

Referring to FIG. 9, a schematic diagram of an exemplary assembled two part dispensing device 10 is shown. Specifically, the device 10 includes a reusable part 100 coupled to a disposable part 200. In some embodiments, the pumping mechanism 150 may be configured to be mechanically coupled to the reservoir 220 (e.g., in implementations that includes a piston-type pumping mechanism) or to the delivery tube 230 (e.g., in implementation that include a peristaltic-based pumping mechanism). The disposable part 200 includes a reservoir 220 that may be filled prior to attachment of the disposable part 200 to the reusable part 100.

Referring to FIGS. 10a-13f, diagrams depicting an exemplary piston-type pumping mechanism and exemplary ways of filling the reservoir 220 with therapeutic fluid are shown.

Figure 10A:
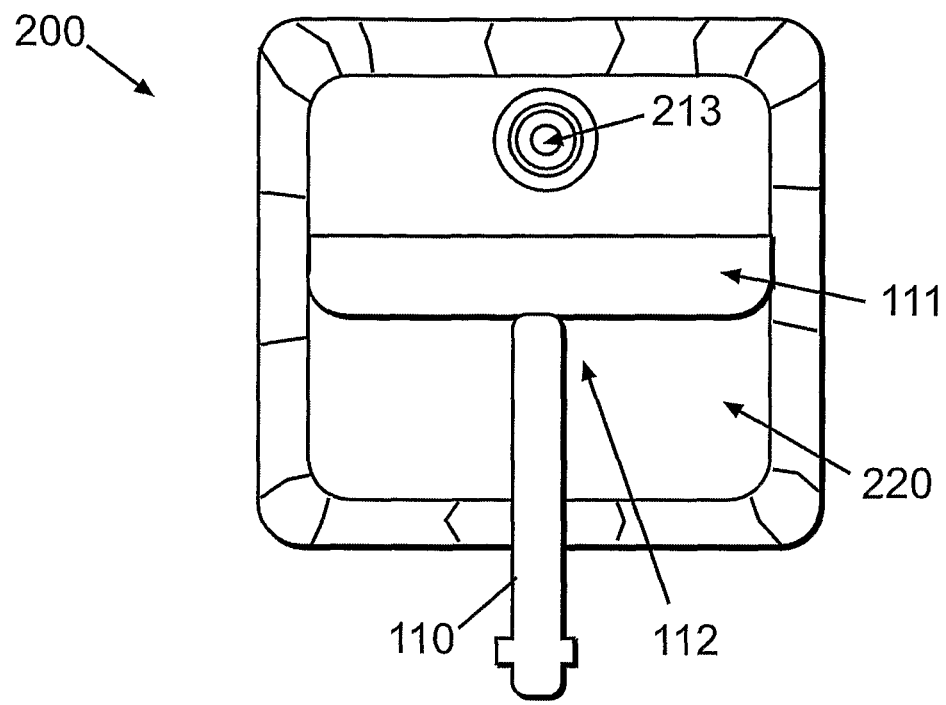
FIGS. 10a-b are schematic diagrams of exemplary disposable parts.
Figure 10B:
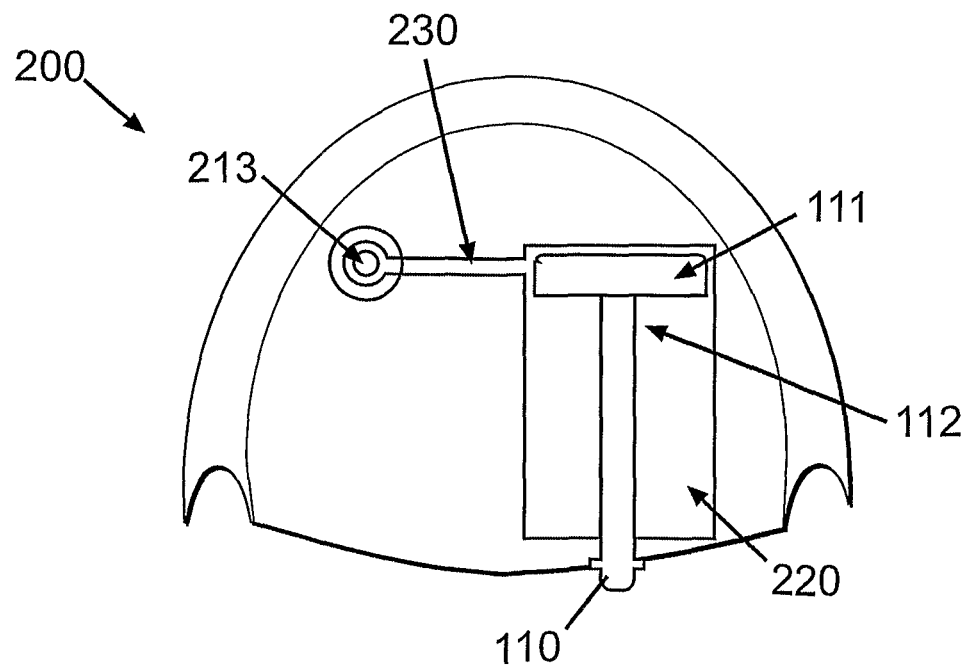

Referring to FIG. 10a, a schematic diagram of an exemplary disposable part 200, functioning by itself as a reservoir 220, is shown. In this configuration, the volume of the reservoir 220 is limited by the volume of the disposable part 200. The device includes a piston-type pumping mechanism. The pumping mechanism is provided with a piston 112 which includes a plunger rod 110 and a plunger head 111. The piston is configured to push fluid towards an outlet port 213 that is typically situated at the bottom of the disposable part 200. FIG. 10b depicts another implementation of an exemplary disposable part 200 that includes dedicated reservoir 220 and a piston 112. In the shown embodiment of FIG. 10b, the piston 112 includes a plunger rod. 110 and a plunger head 111. The piston 112 can be situated inside the reservoir 220. A tube 230 is provided to deliver therapeutic fluid from the reservoir 220 to the outlet port 213.

Figure 11A:
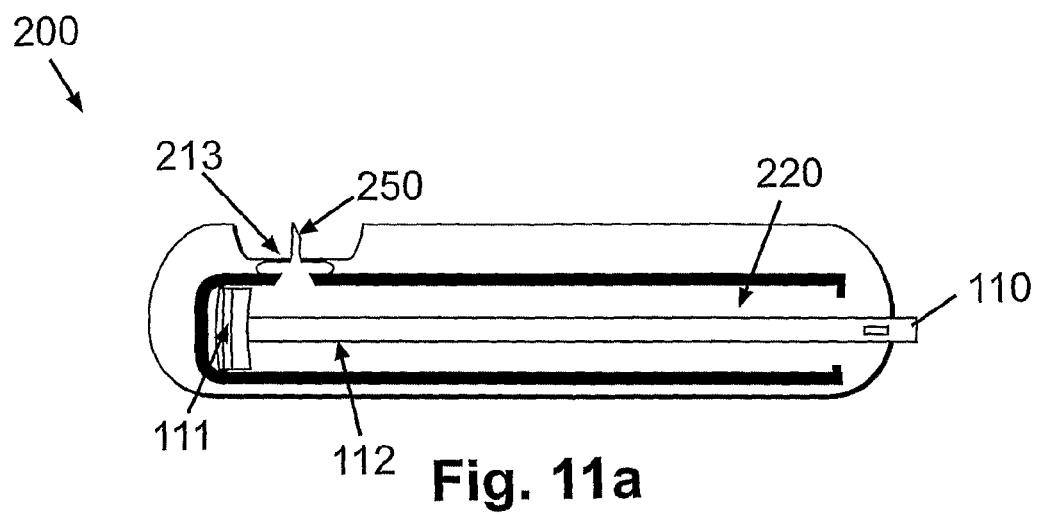
FIGS. 11a-g are schematic diagrams and views depicting an exemplary reservoir-filling process using a plunger.
Figure 11B:
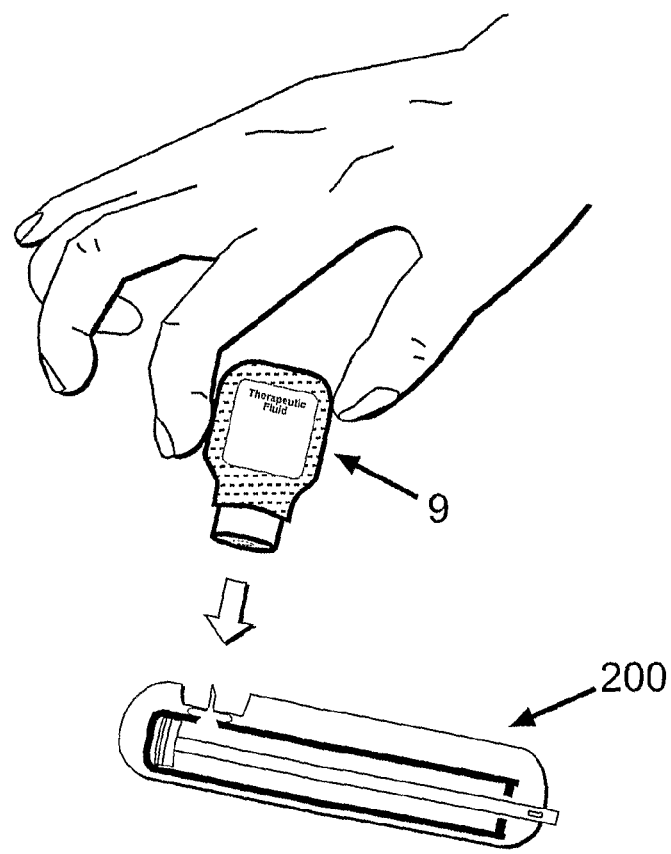
Figure 11C:
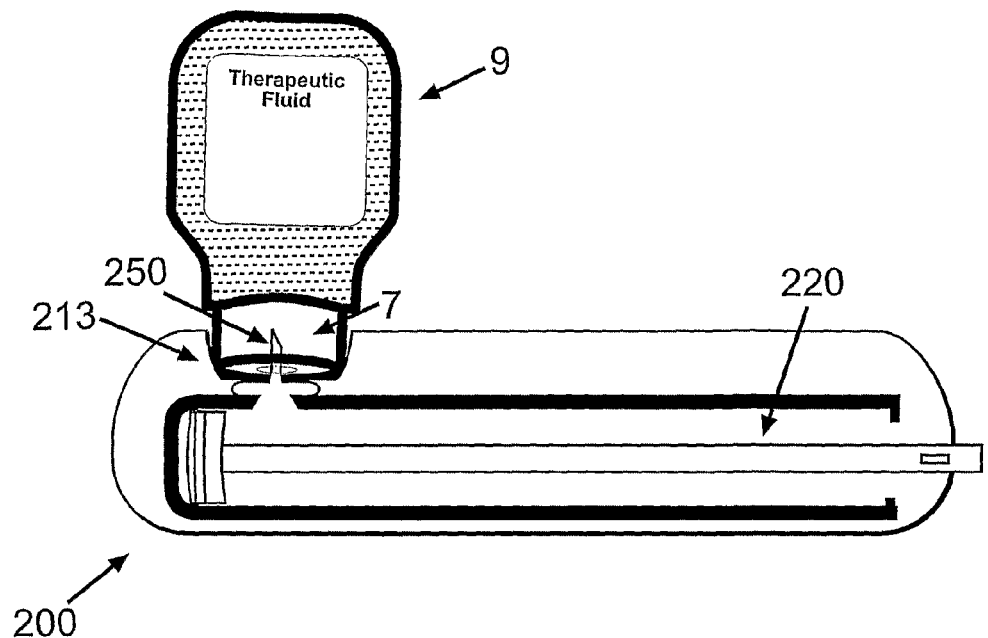
Figure 11D:
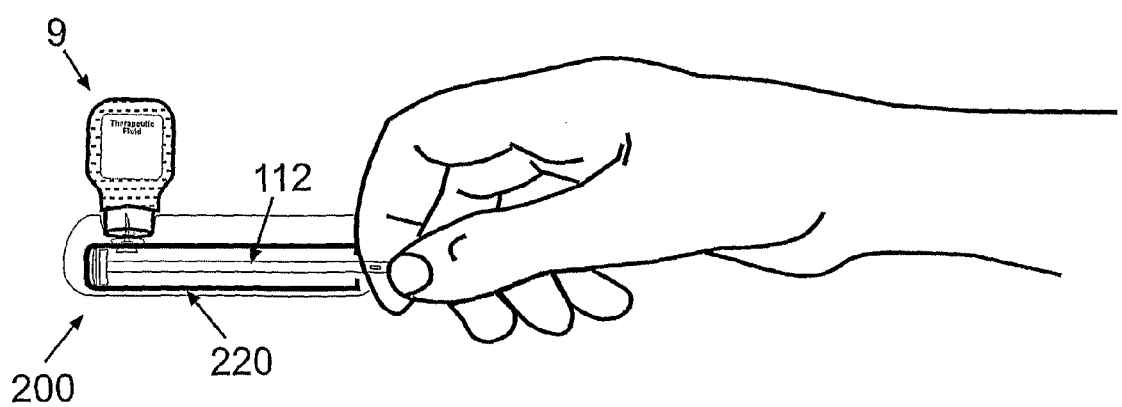
Figure 11E:
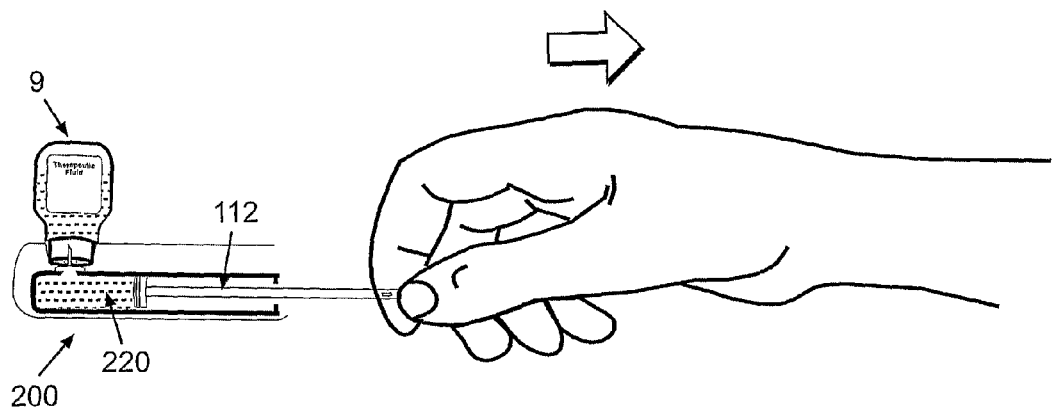
Figure 11F:
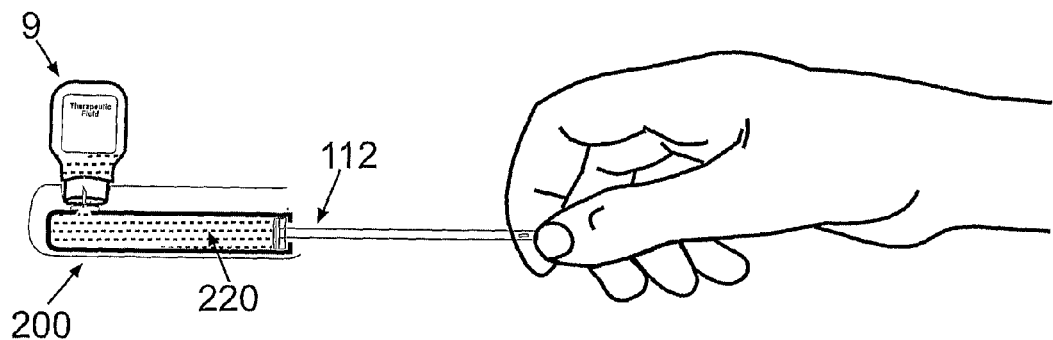
Figure 11G:
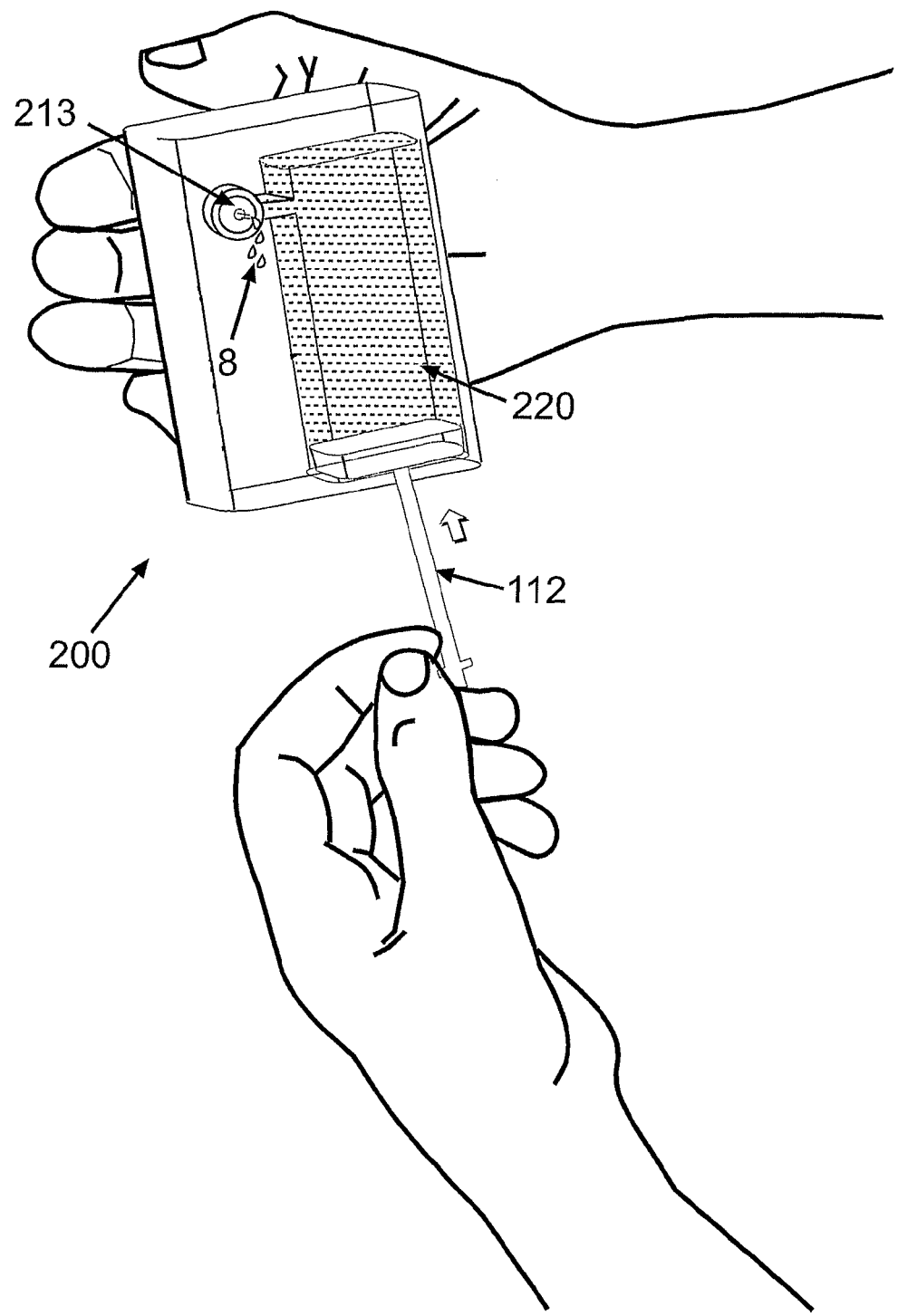

Referring to FIG. 11a, a cross-sectional schematic diagram of an exemplary disposable part 200, similar to the disposable part 200 depicted in FIG. 10b, is shown. The disposable part is depicted prior to filling of the reservoir 220 with fluid. Filling of the reservoir 220 is performed using a plunger rod 110 and a plunger head 111. Referring to FIG. 11b, a diagram of an exemplary drug vial 9 prior to its connection to the disposable part 200 is shown. FIG. 11c illustrates the vial 9 connected to the outlet Port 213. As shown, the disposable part 200 may include a connecting lumen 250 to pierce the vial septum 7 to enable fluid to be drawn from the vial 9 to the reservoir 220 using, for example, a retractable plunger. FIGS. 11d-11f illustrate an exemplary filling procedure of the reservoir 220. The amount of fluid to be drawn may be determined, based on the patient's daily dose requirement to thus reduce therapeutic fluid waste. FIG. 11g illustrates exemplary priming (e.g., air purging) of the reservoir 220. Air bubbles can be purged by holding the disposable part 200 in a substantially upright position (i.e., when the outlet port 213 is generally elevated) and gently pressing the plunger 112 until fluid 8 is seen to be dripping from the outlet port 213.

Figure 12A:
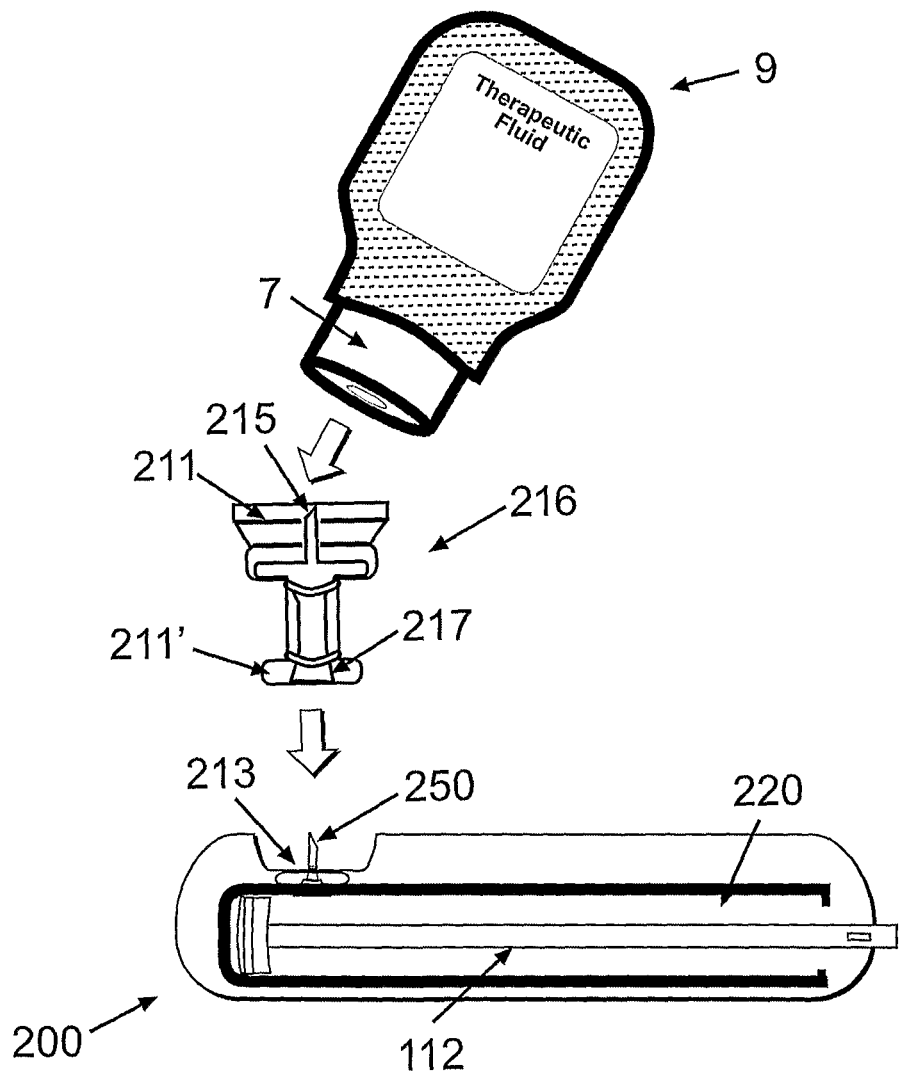
FIGS. 12a-b are schematic diagrams illustrating exemplary connection of the therapeutic fluid container to an adapter.
Figure 12B:
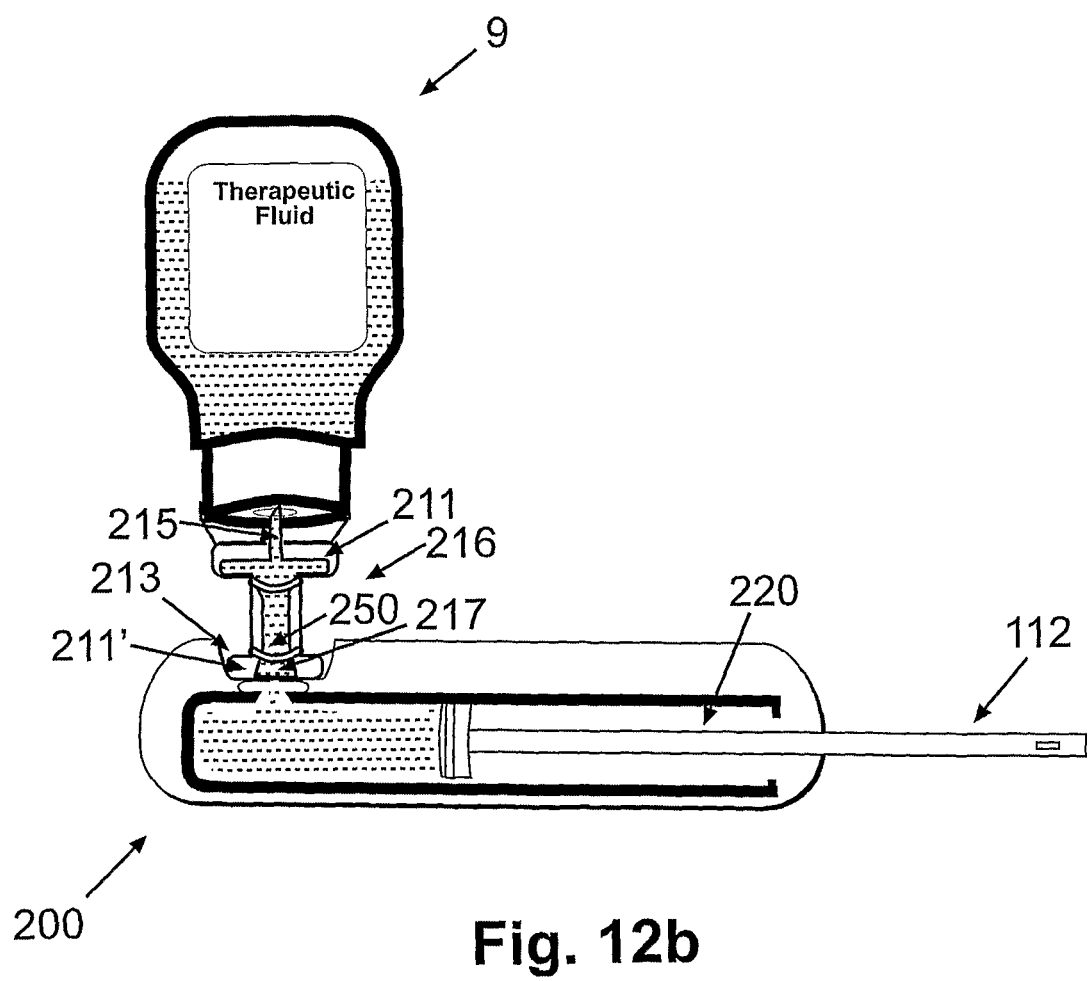

Referring to FIG. 12a-b, schematic diagrams of another exemplary reservoir filling procedure using an auxiliary adapter 216 are shown. FIG. 12a depicts the adapter 216 having two ports: an upper port 211 and a lower port 211'. The upper port 211 is configured to be connected to the vial 9 and may be provided with a needle 215 to pierce the vial's septum 7. The lower port 211' is configured to be connected to the reservoir 220 and can be sealed with a rubber septum 217 that is pierceable by a lumen 250 disposed in the outlet port 213. A displaceable piston 112 may be received (at least partially) within the volume of the reservoir 220 of the disposable part 200. FIG. 12b illustrates an exemplary connection of the adapter 216 to the disposable part 200 and the vial 9. To draw fluid from the vial 9, the piston 112 is retracted outwardly from the inner volume of the reservoir 220 to cause fluid from the vial to be received.

Figure 13A:
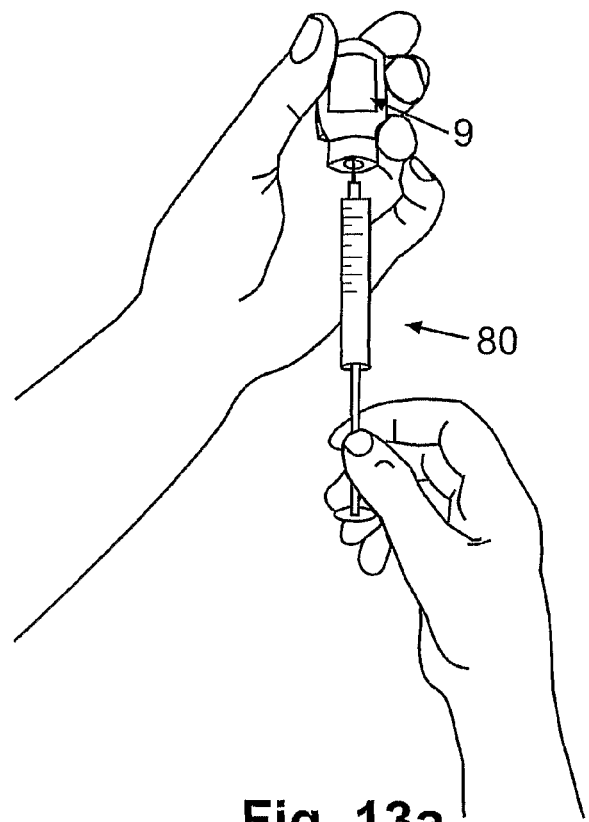
FIGS. 13a-f are views and diagrams illustrating an exemplary reservoir-filling process using a syringe.
Figure 13B:
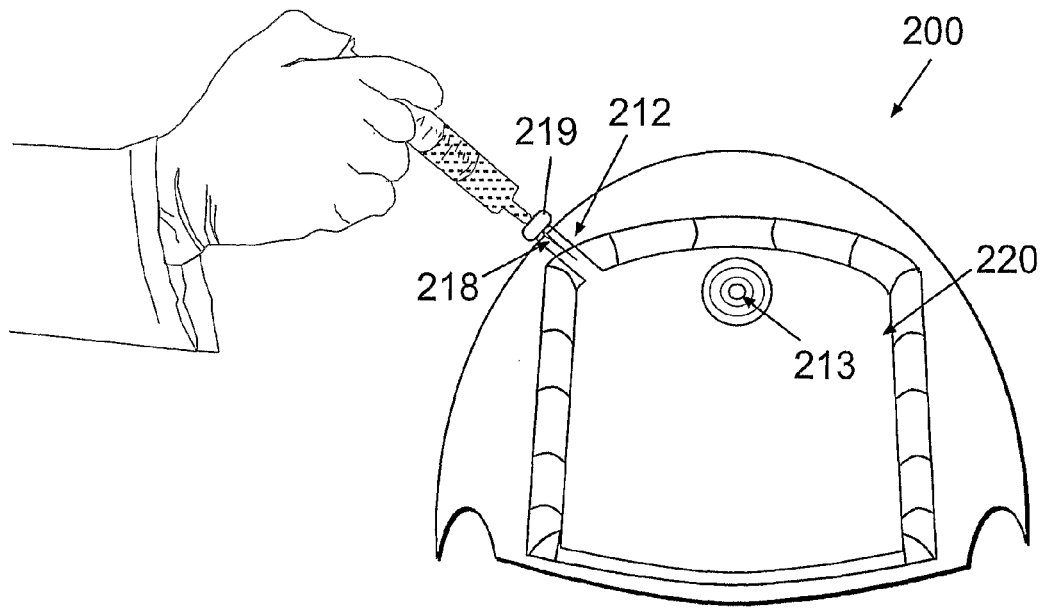
Figure 13C:
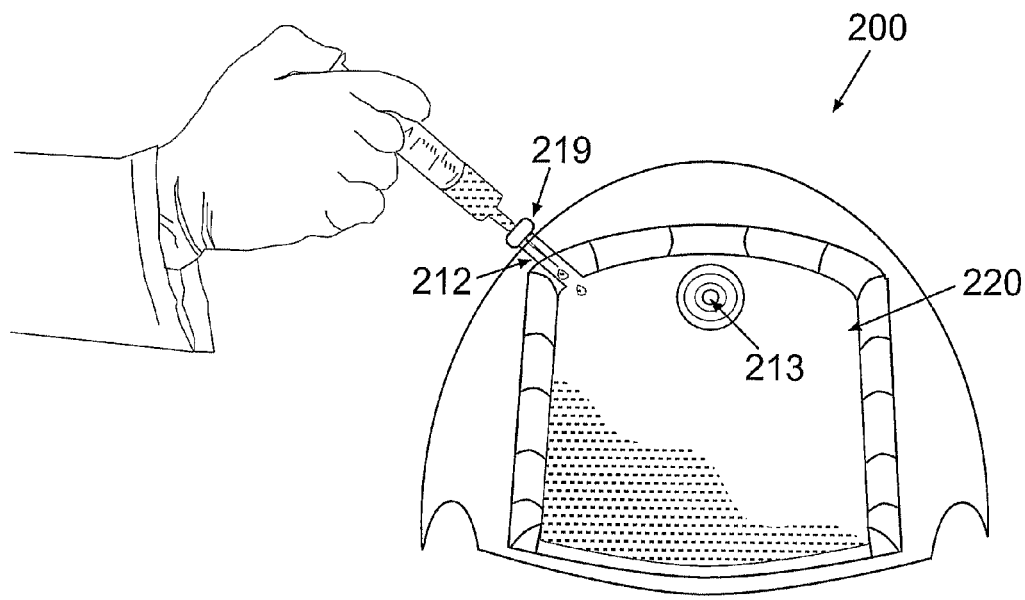
Figure 13D:
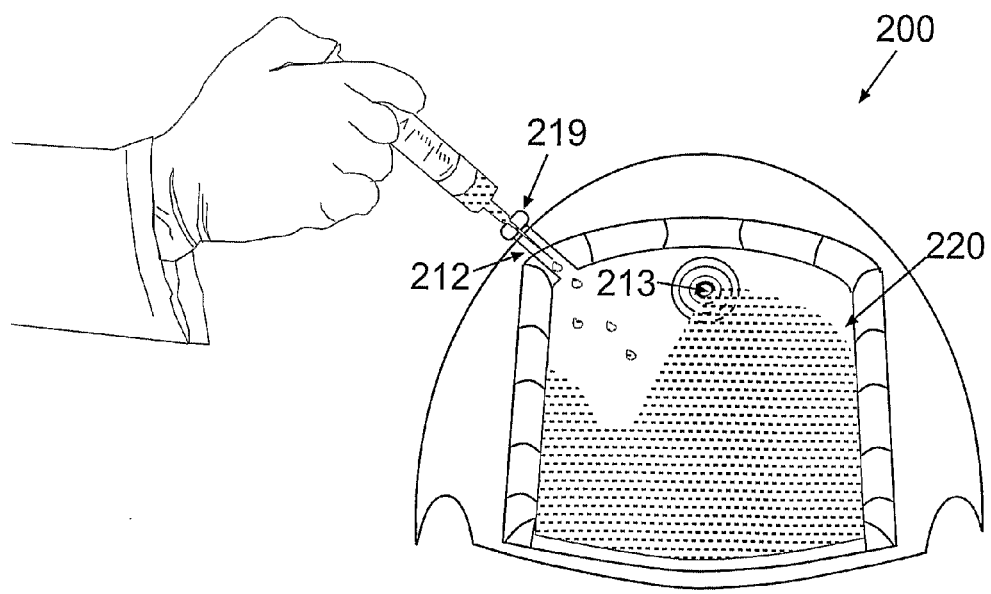
Figure 13E:
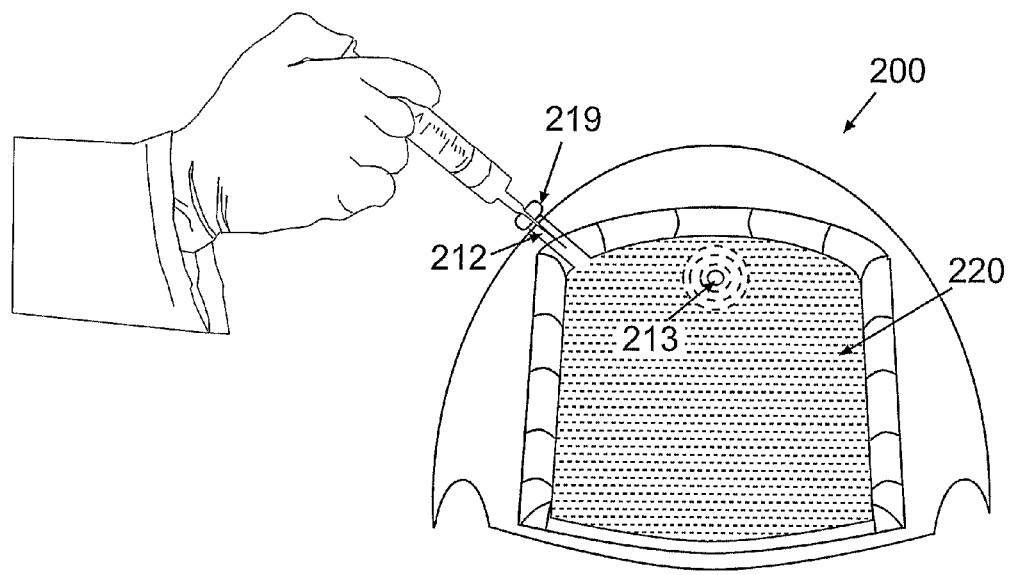
Figure 13F:
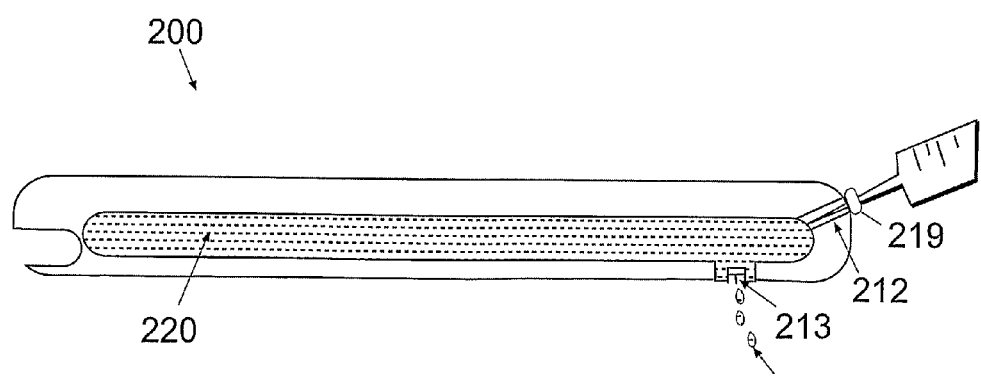

In some embodiments, the reservoir 220 of the dispensing device may be filled using a syringe. Referring to FIGS. 13a-f, diagrams depicting an exemplary reservoir-filling procedure using a syringe 80 are shown. FIG. 13a illustrates fluid being drawn from the vial 9. FIG. 13b illustrates the reservoir 220 having an outlet port 213 at its bottom surface. In some embodiments, the reservoir 220 can be connected to the outlet port 213 via a tube (not shown in FIG. 13a). The syringe needle 218 is configured to pierce the rubber septum 219 of the inlet port 212 to enable filling. Referring to FIGS. 13c-13e, diagrams depicting another exemplary reservoir-filling procedure using a syringe are shown. FIG. 13f illustrates an exemplary priming procedure of the reservoir 220. As shown in FIG. 13f, the reservoir is filled until fluid drops 8 begin to drip from the outlet port 213.

Figure 14A:
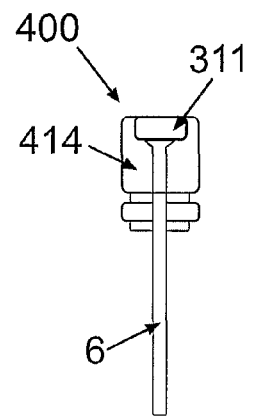
FIGS. 14a-c are schematic diagrams of an exemplary cannula cartridge unit before and after insertion.
Figure 14B:
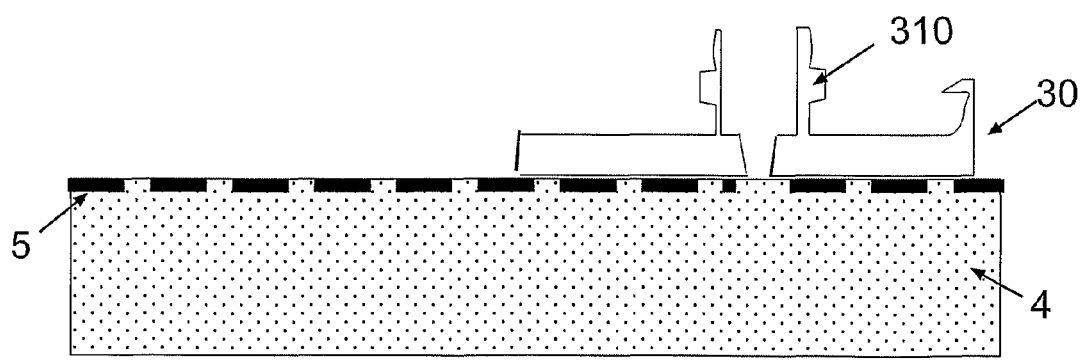
Figure 14C:
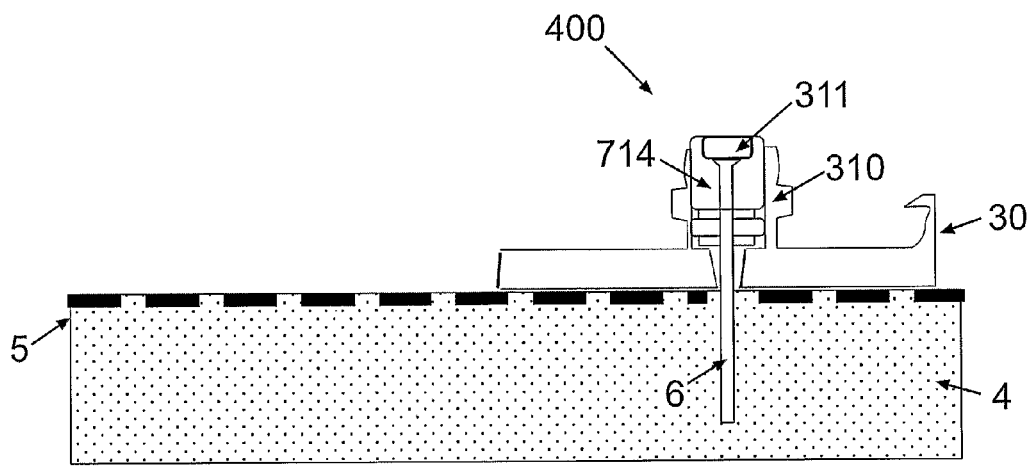

Referring to FIG. 14a, a schematic diagram of an exemplary cannula cartridge unit 400 is shown. The cannula cartridge unit 400 includes a cannula hub 414, a septum 311 and a cannula 6. FIG. 14b illustrates an exemplary port unit 30 configured to receive the cannula cartridge unit 400. The port unit includes a well 310 through which the cannula cartridge unit 400 is inserted. The cannula cartridge unit 400 can be inserted using, for example, an inserter manual, semi-automatic and/or automatic). A description of such an exemplary inserter is disclosed, for example, in co-owned International Patent Application No, PCT/IL08/000860, filed Jun. 25, 2008, claiming priority to U.S. Provisional Patent Application No. 60/937,214, entitled "Insertion device for inserting a cannula into a body," filed on Jun. 25, 2007, the content of which is hereby incorporated by reference in its entirety. FIG.

14c illustrates cannula cartridge unit 400' that has been inserted into the well 310 of the port unit 30 and the cannula 6 subcutaneously inserted into the patient's skin.

Figure 15A:
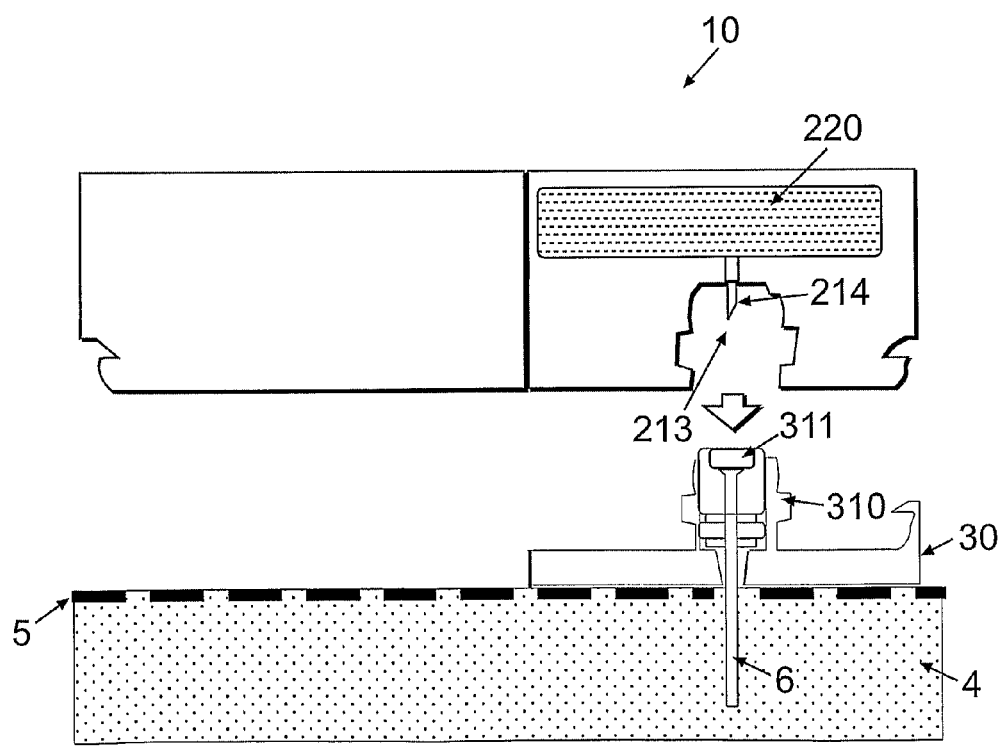
FIGS. 15a-b are schematic diagrams depicting connection of an exemplary fluid delivery device to an exemplary cradle.
Figure 15B:
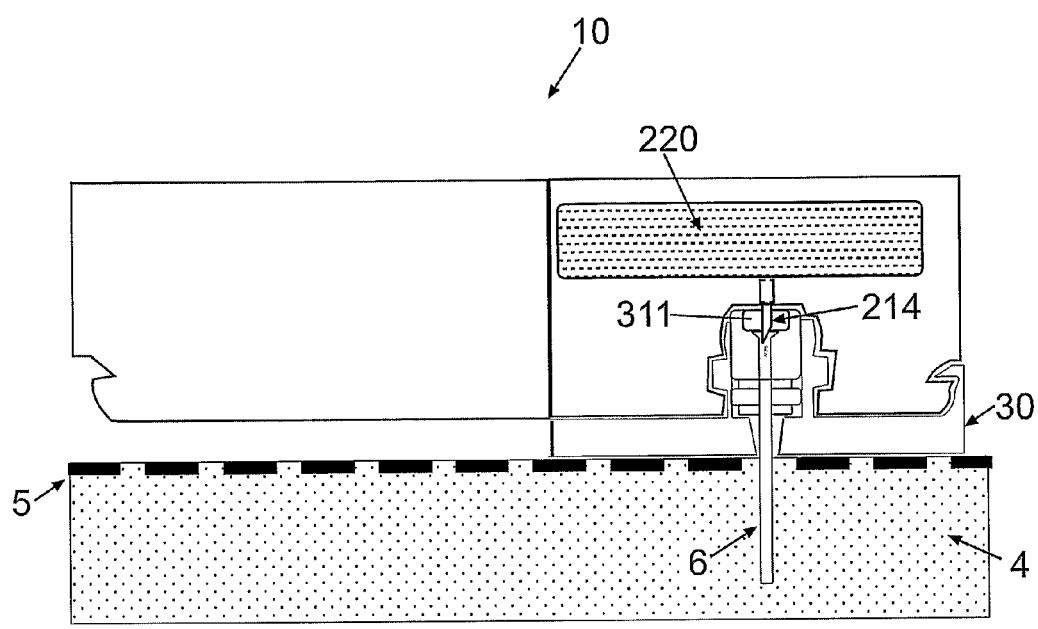

Referring to FIG. 15a, a schematic diagram of an exemplary fluid delivery device 10 positioned to being connected to the port unit 30 is shown, FIG. 15b illustrates the exemplary device 10 connected to the port unit 30. As shown, a connecting lumen 214, provided in the fluid delivery device, is configured to pierce the septum 311 of the port unit to thus enable fluid to flow from the reservoir 220 to the cannula 6 and to the subcutaneous layer 4.

Referring to FIGS. 16-25c, diagrams and views illustrating various exemplary manually-powered driving and pumping mechanisms are shown.

Figure 16:
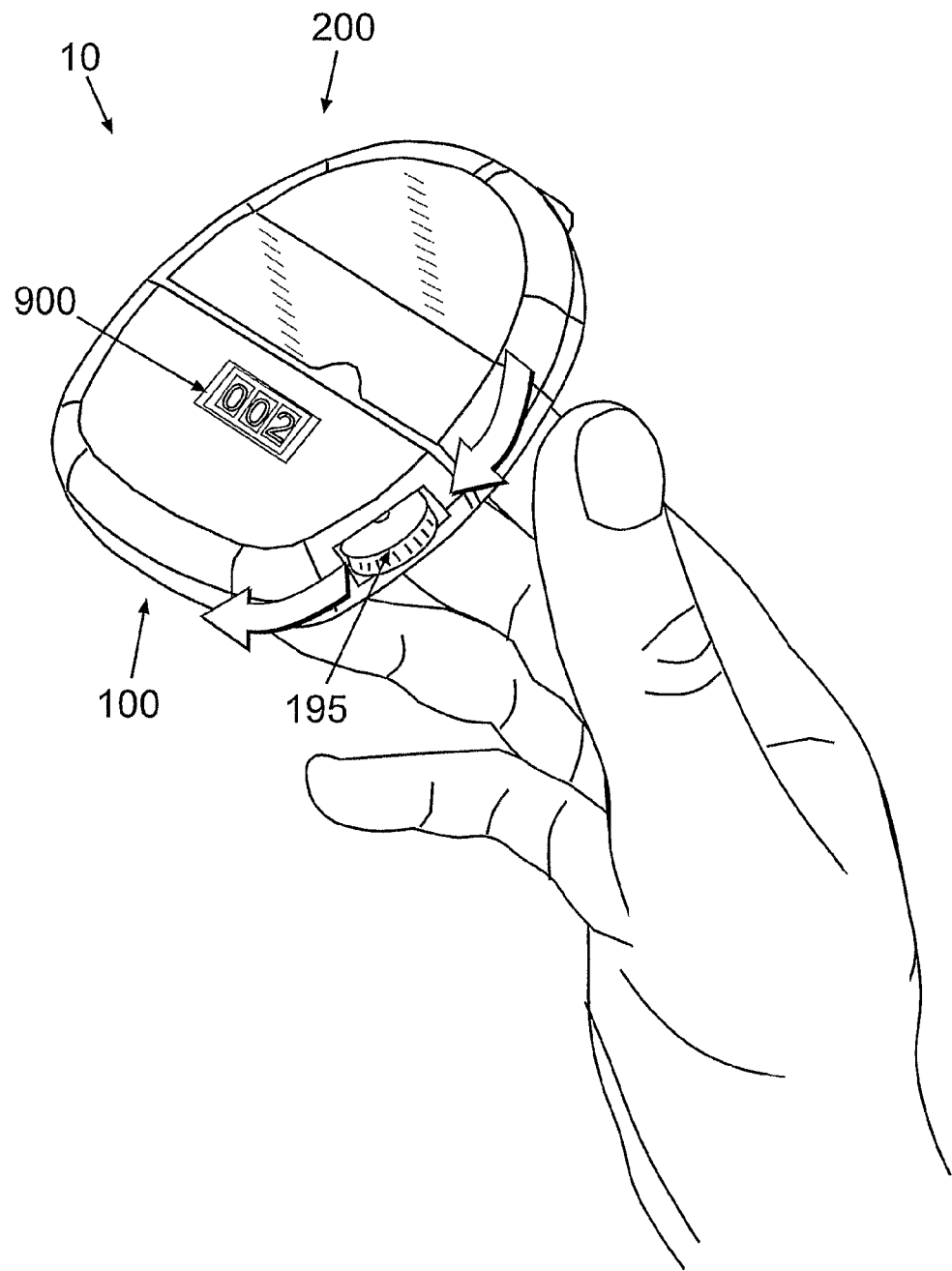
FIG. 16 is a perspective view of an exemplary manually-powered fluid delivery device with a user-actuated rotation wheel.

FIG. 16 is a perspective view of an exemplary dispensing device 10. The dispensing device 10 can be provided with any of the above-described components/units and/or with a dedicated controller to perform manual/semi-automatic/automatic or otherwise regulate fluid delivery to the body of the patient. In some embodiments, such a controller enables manual actuation of a driving and/or pumping mechanism of the device 10 and may include, for example, an activation wheel 195. As will become apparent below, rotation of the activation wheel (also referred to as an actuation wheel) 195 causes fluid infusion/delivery. A counter 900 may be disposed on the dispensing patch unit to enable control of to be delivered dose(s). Manual rotation of the activation wheel 195 may cause actuation of the pumping mechanism (e.g., piston-type or peristaltic-type pumping mechanism) to thus cause fluid infusion to be performed. For an accurate control of fluid delivery, an indicator producing a signal (e.g., a click sound, a visual indication such as flashing light, or any other indication) may be provided to accompany activation/actuation of the wheel 195, in some embodiments, the activation wheel rotation is rotatable in a unidirectional manner to prevent retraction of delivered therapeutic fluid back into the reservoir. Alternatively and/or additionally, the pumping mechanism may be retracted in particular situations, such as, for example, during reservoir filling, reservoir replacement, to verify the driving mechanism proper functionality, etc.

Figure 17A:
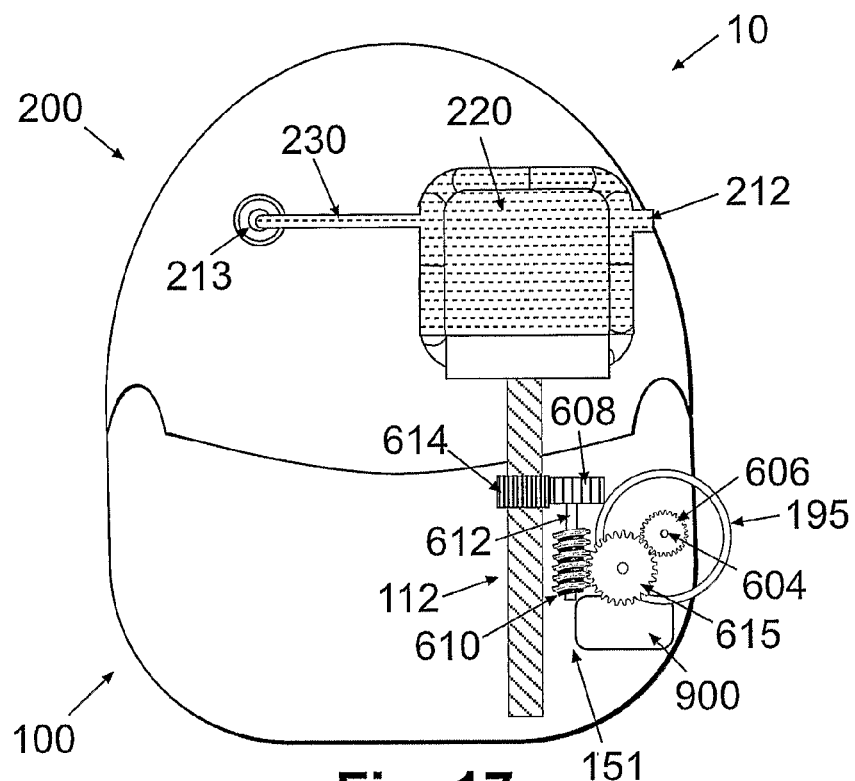
FIGS. 17a-b are schematic diagrams of an exemplary manually-powered delivery device with a piston-based pumping mechanism.

Referring to FIG. 17a, a schematic diagram of an exemplary fluid delivery device 10 that includes an activation/actuation wheel 195 operatively coupled to a piston-type pumping mechanism 151 is shown. The activation wheel 195 may be connected to a power-transfer mechanism (also referred to as a driving mechanism) to transfer manually-delivered power provided by a user to mechanically actuate a pumping mechanism. The delivery device may thus be implemented without using electrically-generated power. The driving mechanism may include, in some embodiments, one or more gears. For example, the one or more gears may include a small-size cog-wheel 606 having teeth that can engage with teeth of a larger cog-wheel 615. Rotation of the wheel 195 causes the larger cog-wheel 615 to turn and to consequently rotate a worm 610. One end of the worm 610 is rigidly connected to one side of a rod 612. The other side of the rod 612 is connected to a cog-wheel 608. Rotation of the cog-wheel 608 urges a screw-nut 614 operatively coupled therewith to turn. By turning the screw-nut 614, the threaded rod of piston 112 of the pumping mechanism, which is operatively coupled to the screw-nut, is linearly displaceable in a forward direction. When linearly displaced, the piston 112 is configured to push fluid within the reservoir 220 and force it to pass through the tube 230 and exit from the outlet port 213.

Figure 17B:
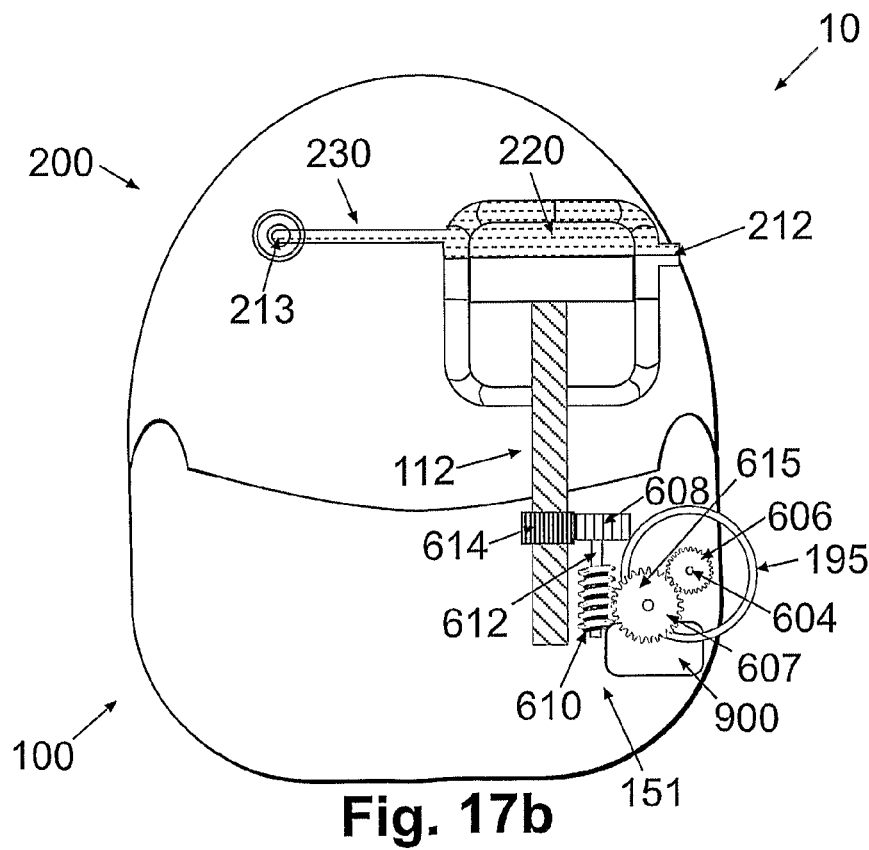

FIG. 17b further illustrates the piston-type pumping mechanism during movement of the piston 151, which forces fluid to exit through the outlet port 213. After completing the infusion operation and depleting the reservoir, the user (e.g., patient) can manually retract the piston 112 (e.g., using a handle coupled to the piston 112) backward until the piston is in its initial position, whereupon the reservoir and/or the entire disposable part 200 may be replaced with a new one.

Figure 18:
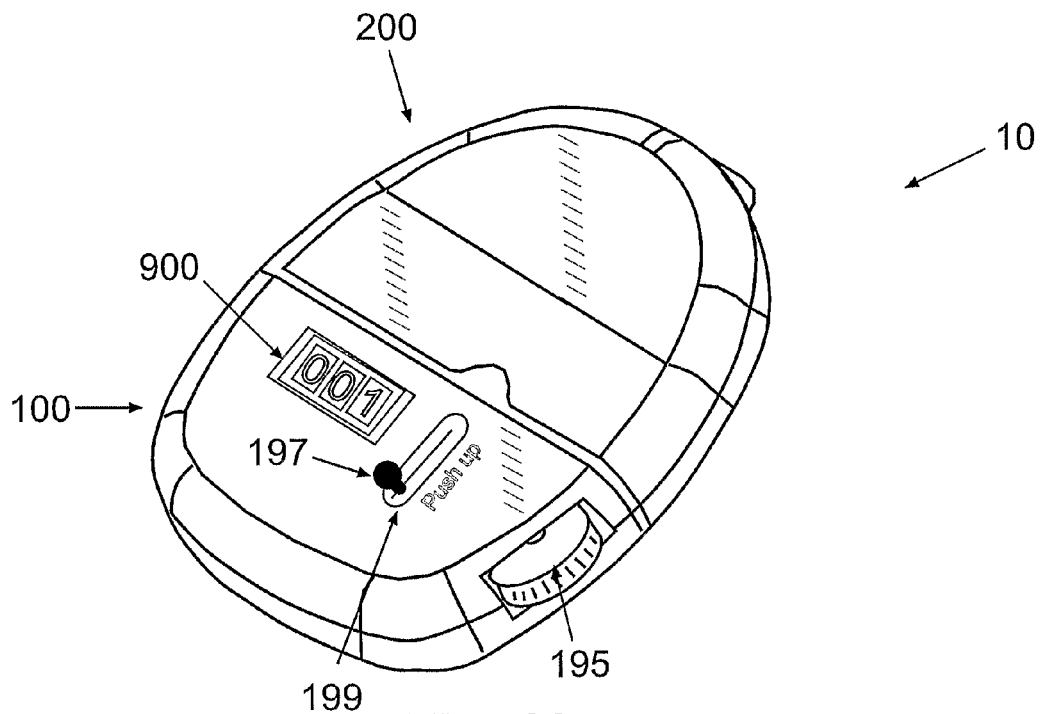
FIG. 18 is a perspective view of an exemplary delivery device with manual-power actuation mechanism and a limiter.

Referring to FIG. 18, an isometric view of another exemplary configuration of the device 10 implemented using a piston-type mechanism is shown. The dispensing device may be provided with rotating activation/actuation wheel 195, a limiter handle 197 and a limiter track 199. A counter 900 may be provided to facilitate manual control of the fluid delivery.

Figure 19A:
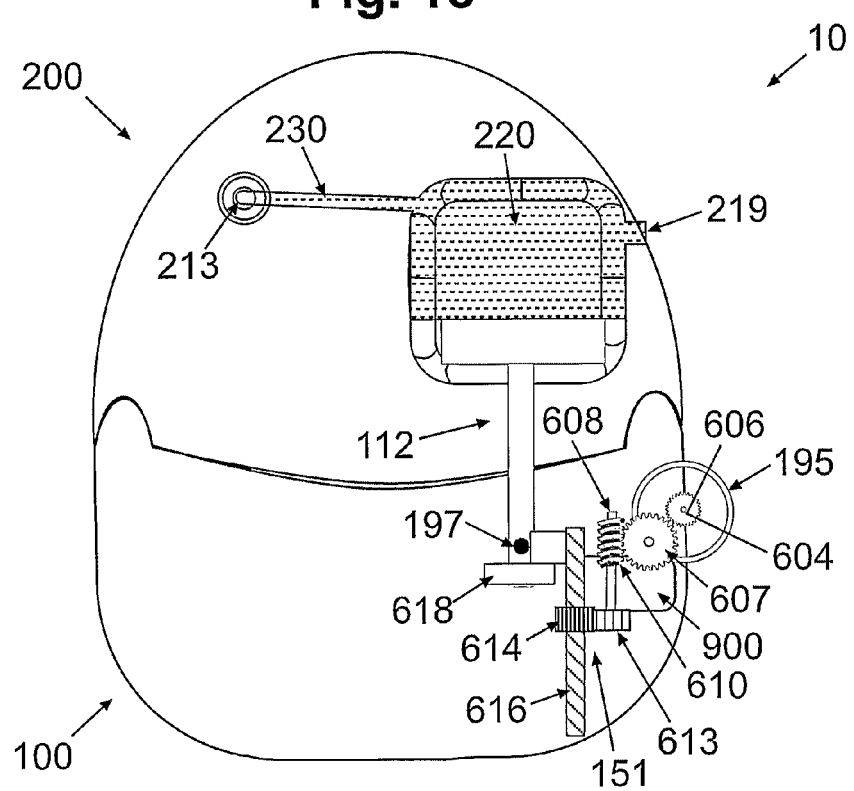
FIGS. 19a-c are schematic diagrams of an exemplary fluid delivery device with a piston-based pumping mechanism and a limiter.
Figure 19B:
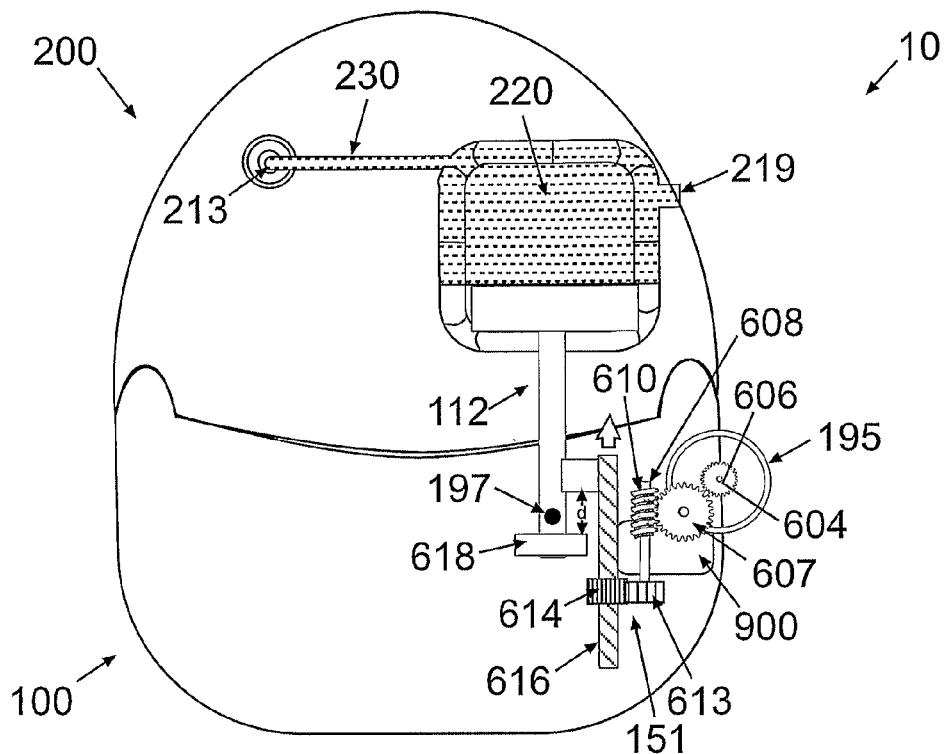
Figure 19C:
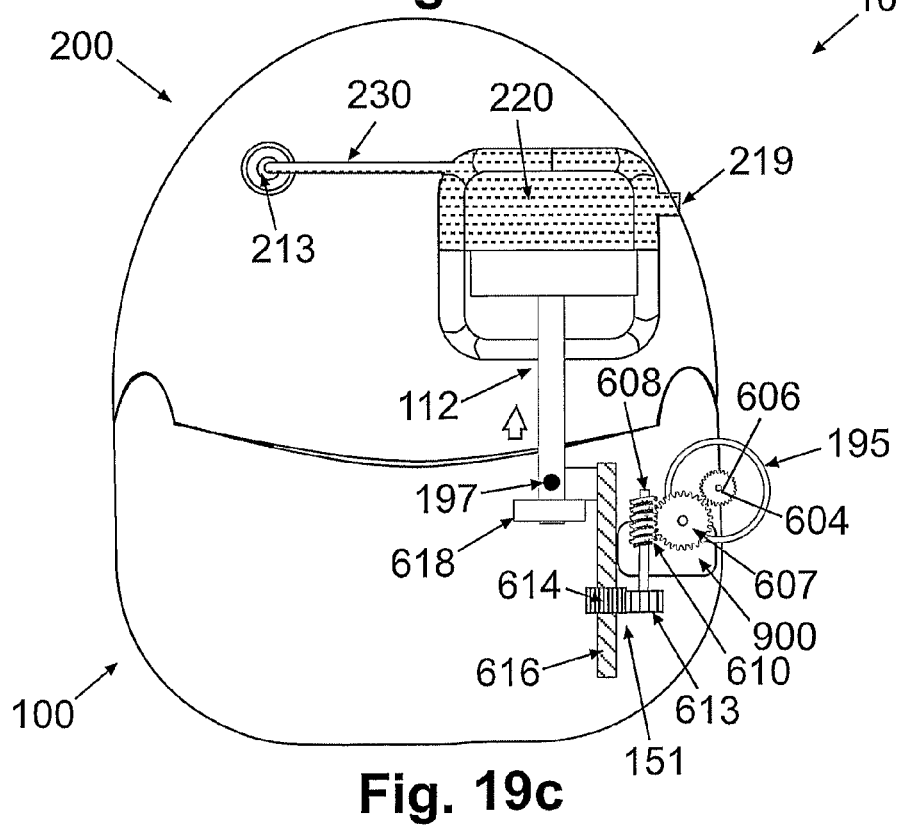

Referring to FIG. 19a, a schematic diagram of another exemplary fluid delivery device with a manually-powered driving and pumping mechanism, similar to those depicted in FIGS. 17a-b, and that further includes a limiter 616 is shown. The limiter 616 is configured to prevent displacement of the piston beyond a pre-set spatial position defined by the limiter. The pumping mechanism is provided with a screw-nut 613 and a limiter's nut 614. The rotating screw nut 613 rotates the limiter's nut 614 which consequently displaces the limiter 616 in a forward direction or by actuating the piston with the driving mechanism. The limiter 616 position sets the allowed distance for piston displacement. The displacement of the piston 112 may be performed, for example, by pushing the handle 197 in a forward direction. Piston displacement can be halted when the piston's bottom end 618 comes in contact with the limiter 616. In some embodiments, additional safety measures may be employed to enable the patient to press the handle 197 in a downward direction prior to displacement of the handle 197. Such safety measures would prevent unintentional bolus delivery. FIG. 19b illustrates an exemplary device 10 after dose adjustment, performed by rotating the activation/actuation wheel 195 which causes the limiter 616 to advance an to initial position. FIG. 19c illustrates the piston 112 at the end of the drug delivery operation when the bottom end 618 of the piston reaches the point of contact with the limiter 616. In some embodiments, the limiter may be actuated separately from the driving mechanism. Alternatively and/or additionally, the limiter may be used as a safety mechanism to lock the driving mechanism and to thus prevent accidental fluid delivery.

Figure 20:
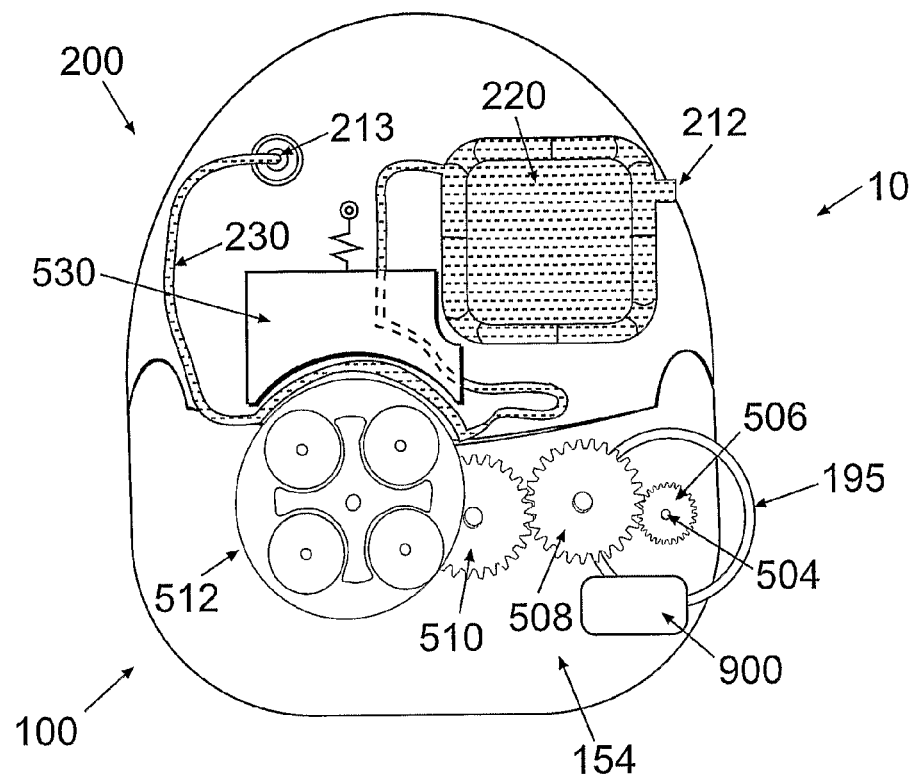
FIG. 20 is a schematic diagram of an exemplary manually-powered fluid delivery device with a peristaltic-based pumping mechanism.

Referring to FIG. 20, a schematic diagram of another exemplary fluid-delivery device 10, implemented using peristaltic-based mechanism 154, is shown. The device 10 includes a rotateable activation/actuation Wheel 195 coupled, e.g., via an axle 504, to a small-size gear (cog-wheel) 506. Rotation of the activation wheel 195 causes the two other larger gears 508 and 510 to rotate to cause rotation of a peristaltic rotor 512.

The peristaltic rotor 512 is configured, during its rotation, to press a tube 230 against a stator 530 to enable fluid pumping towards the outlet port 213 and into the patient's body. A counter 900 is included with the device 10 to count the number of wheel revolutions to thus indicate the amount of drug dose (e.g., insulin units) delivered.

It is to be noted that in the embodiments described above in connection with FIGS. 16-20, the fluid dispensing patch unit can be provided with functionality for autonomous control of the fluid delivery (e.g., without implementing automatic control to automatically regulate the extent of pump actuation and/or fluid delivery). This capability can be rendered by virtue of providing the dispensing patch unit with a dedicated control mechanism operatively coupled to the dispensing mechanism. Autonomous control of fluid delivery can enable manufacturing of a dispensing patch unit 10 without expensive electronics or optical component. The second advantage of such a patch unit lies in the fact that it removes apprehensions a user may have about using a device implemented using automatic fluid infusion capability (e.g., device which electronically controls the amount of insulin delivered to his/her body). Thus, with devices such as the exemplary devices described herein, the patient manually controls the fluid delivery and is able to actuate (including starting, stopping and/or resuming) drug delivery at his/her own discretion.

Figure 21A:
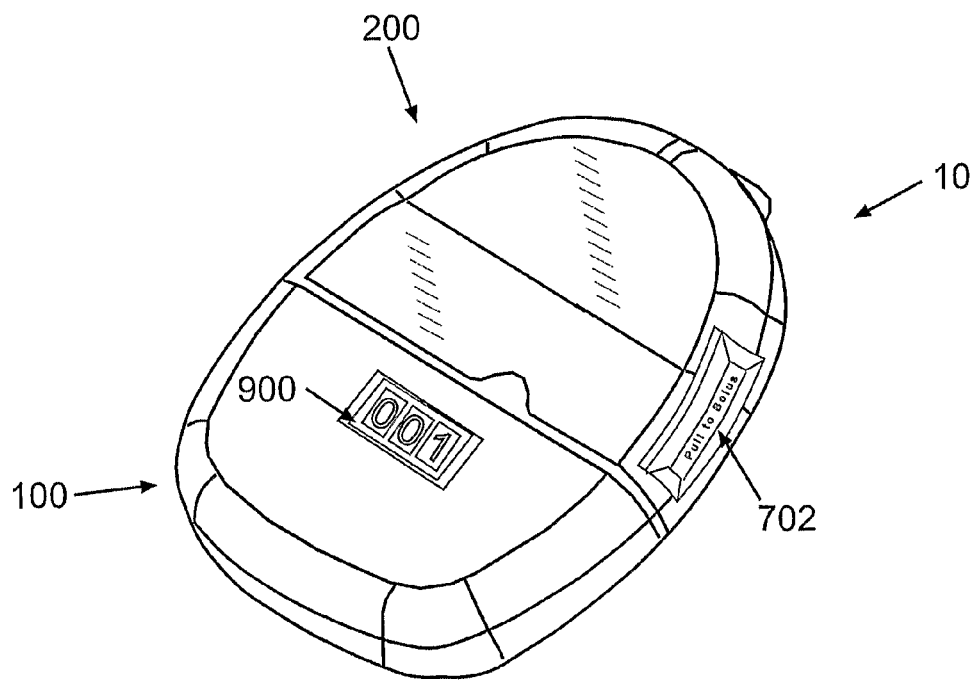
FIGS. 21a-c are perspective views of an exemplary manually-powered actuation process using a spring mechanism.
Figure 21B:
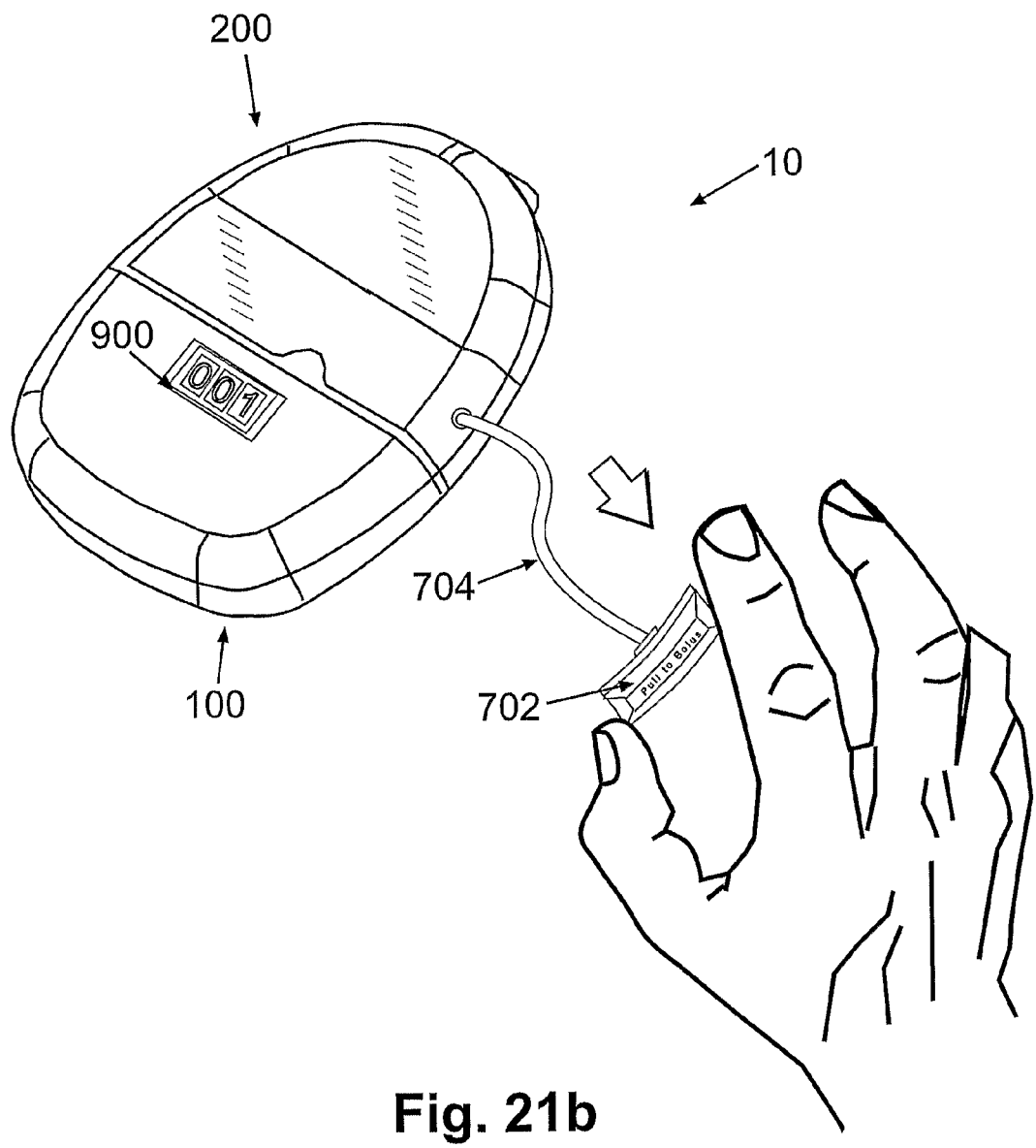
Figure 21C:
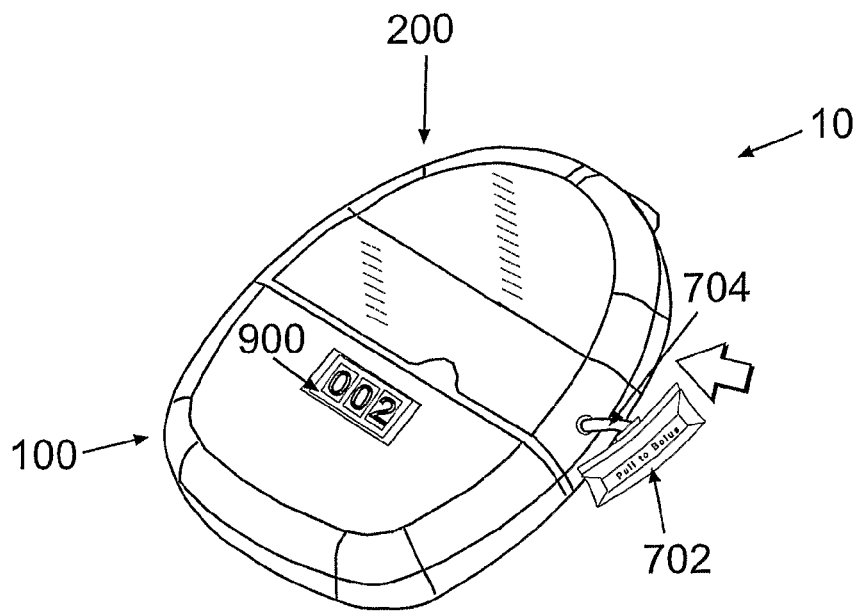

Referring to FIGS. 21a-c, diagrams of an exemplary fluid delivery device 10 having a spring-based mechanism to actuate the power-transfer and/or pumping mechanism of the device is shown. The spring mechanism is provided with a spring, loadable upon pulling a spring handle 702 connected to a pulling string 704 to enable delivery of a pre-determined dosage (e.g., bolus dosage). This mechanism thus frees the patient/user from having to continually manually actuate the device until delivery of the required dosage is completed. Thus, after the spring of the spring mechanism is loaded (i.e., the string is pulled), the release of the spring (e.g., to cause delivery of bolus dosage) requires no additional operational intervention from the patient. FIG. 21a illustrates dispensing device 10 prior to commencement of delivery operations. FIG. 21b illustrates the device 10 in operation, i.e., during the pulling action. As shown, the string coupled to the spring is pulled, using a pulling-spring handle 702 to an initial position. Particularly, the string coupled to the spring is pulled in a rotational direction opposite the rotational direction at which the spiral spring is biased. FIG. 21c illustrates retraction of the pulling string 704 upon release of the pulling handle 702. Release of the string causes the spiral spring to rotate in the direction in which the spiral spring is biased to thus cause rotation of the at least one gear coupled to the spring-based mechanism.

Figure 22:
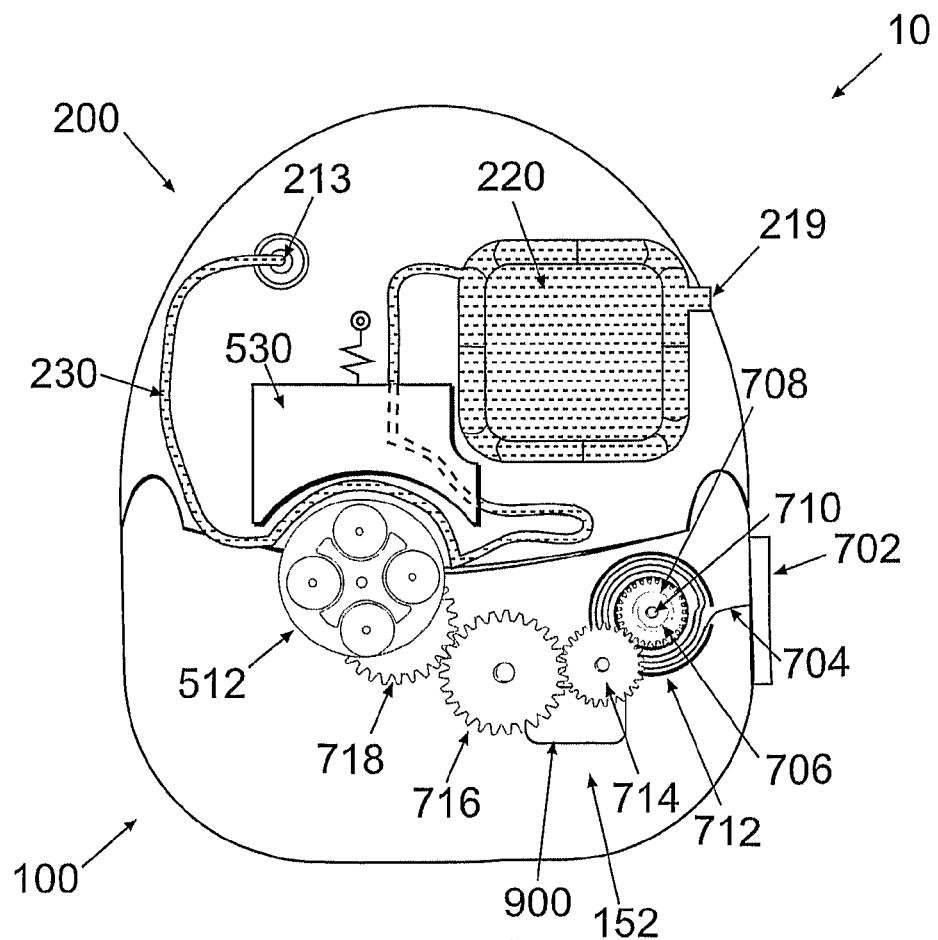
FIG. 22 is a schematic diagram of an exemplary manually-powered fluid delivery device with a spring mechanism.

Referring to FIG. 22, a schematic diagram of a driving mechanism (power-transfer mechanism) 152 actuated by a spiral spring 706 (in a manner similar to that shown in relation to FIGS. 21a-c) is shown. A handle 702 is connected to the spiral spring 706 by a string 704. By pulling the handle 702, the patient loads the spiral spring 706. Upon release of the handle 702, the spiral spring 706 is discharged and drives one or more gears, for example, the cogwheels 714, 716 and 718. The one or more gears of the driving mechanism cause, in turn, a rotor 512 of the peristaltic-based mechanism to be rotated, Rotation of the rotor 512 causes dispensation of fluid via the tube 230 to the outlet port 213 and to the body of the patient. Each string pulling and releasing action corresponds to the discharge of a predetermined dose (e.g., 1 IU of insulin) into the body of the patient. In some embodiments, this driving mechanism 152 can be employed to actuate a piston-type pumping mechanism (not shown in FIG. 22). The driving mechanism 152 may be configured to impart to the dispensing patch unit an ability for autonomous control of fluid delivery, i.e. the dispensing is completely controlled by the patient (e.g., the user provides entirely the actuation required to cause operation of the driving mechanism and/or the pumping mechanism).

Figure 23A:
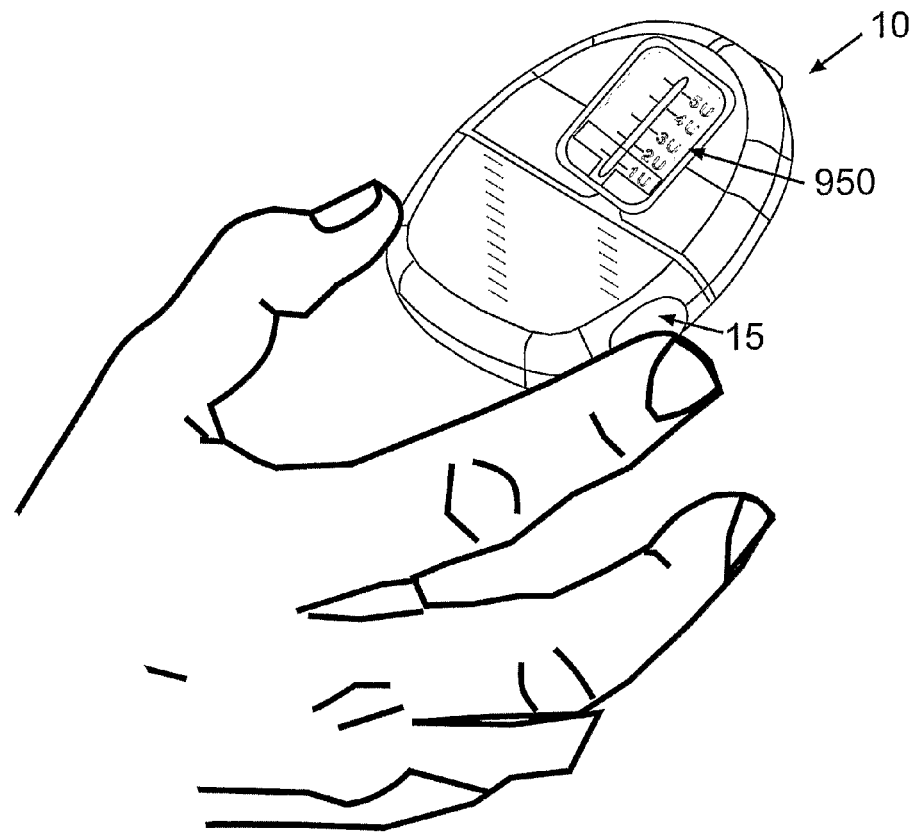
FIGS. 23a-c are perspective views illustrating operation of a pump-air fluid delivery device.
Figure 23B:
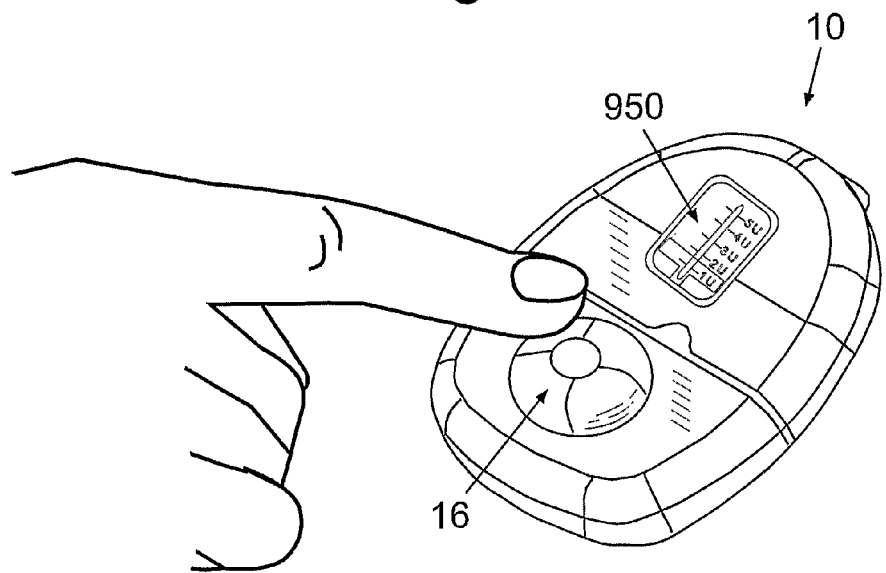
Figure 23C:
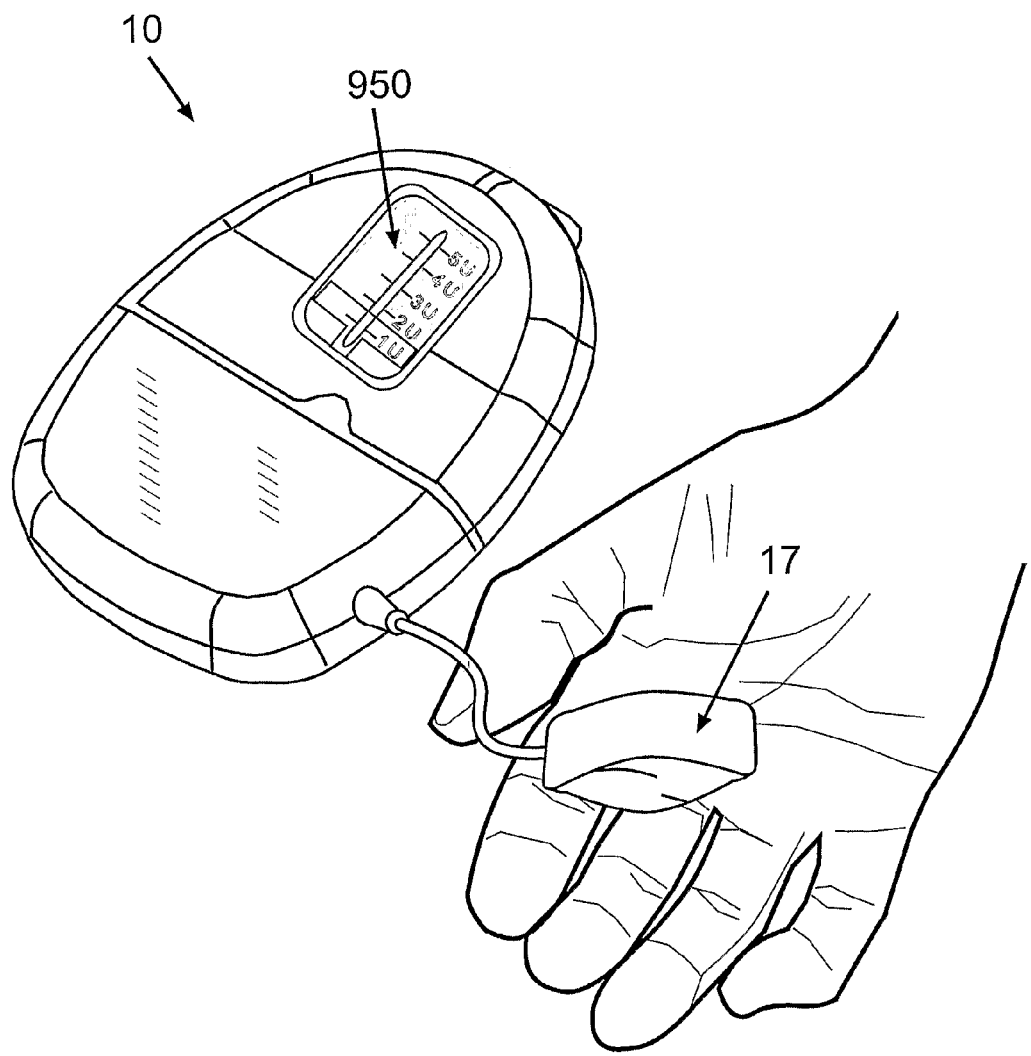

Referring to FIGS. 23a-c, perspective views of an exemplary fluid delivery device including a user-actuated "pump-air" infusion pump is shown. FIG. 23a illustrates fluid pumping by pressing buttons 15 provided on both sides of the device 10. FIG. 23b illustrates pumping by pressing a pumping button 16 situated on the top of the device 10. FIG. 23c illustrates pumping by using activation/actuation mechanism configured as a blower 17. A transparent window 950 enables monitoring of the content of reservoir 220.

Figure 24A:
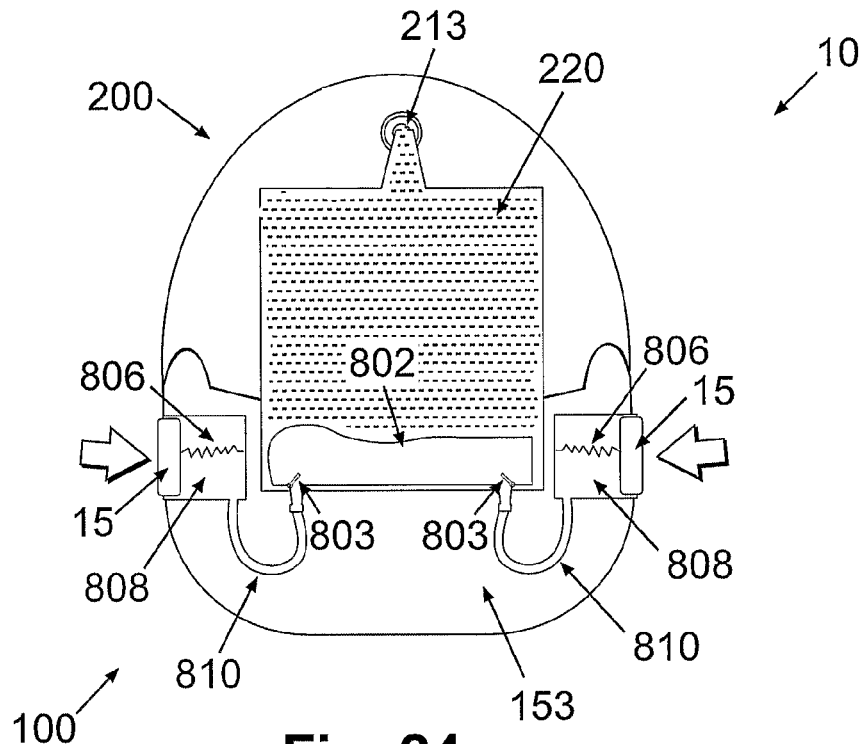
FIGS. 24a-b are schematic diagrams of a fluid delivery device using a pump-air mechanism.
Figure 24B:
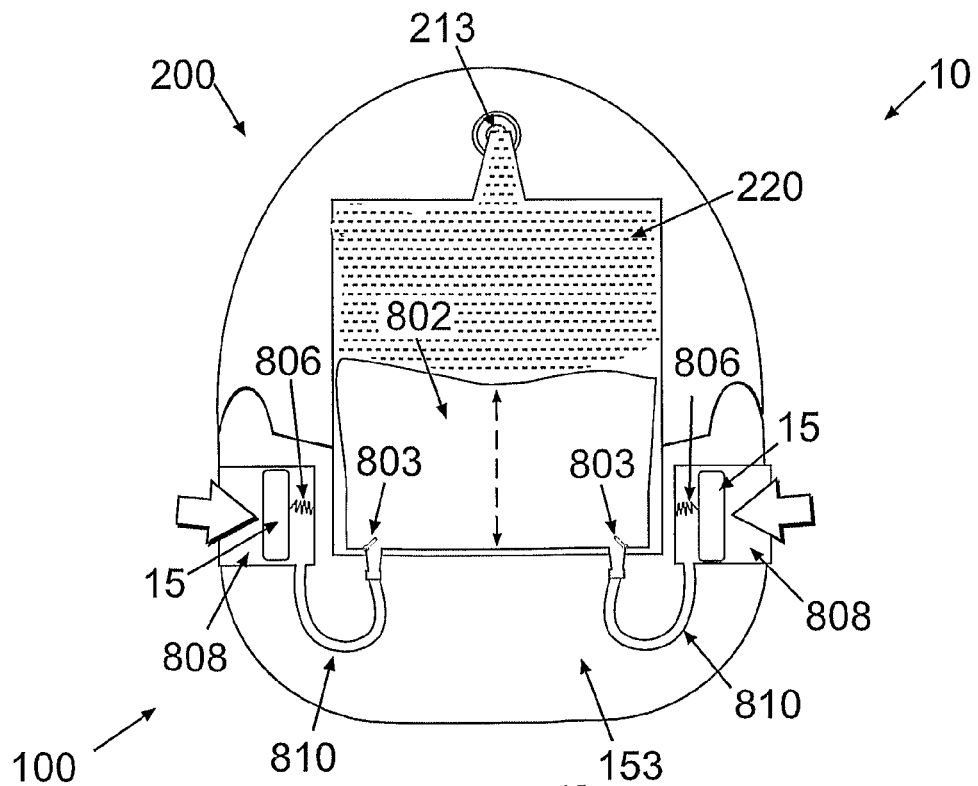

Referring to FIGS. 24a-b, schematic diagrams of an exemplary fluid delivery device 10 that includes a "pump-air"-based mechanism 153 is shown. The pump-air mechanism includes an inflatable air container 802 to actuate the reservoir 220, and at least one air-injection device to deliver air to the inflatable air container. In some embodiments, each of the at least one air injection device includes an air tube in communication with the air container and an air compression chamber in communication with the air tube. The air compression chamber includes a plunger displaceable by the user within an inner volume of the air compression chamber. In some embodiments, the plunger is implemented as a user-actuatable button 15 coupled to an outwardly biased spring. Actuation of the button to push it inwards into the air compression chamber causes air to be pumped into the air container. When the user releases the button, the outwardly biased spring causes the button to be displaced outwardly to its initial position to thus cause ingress of ambient air into the air compression chambers 808. FIG. 24a illustrates a dispensing device 10 in its initial state prior to operation, at which point the buttons 15 are not pressed and the displaceable plungers (e.g., the buttons coupled to the springs 806) are in their released positions. As shown, the inflatable air container 802 is connected via air tubes 810 and unidirectional valves 803 to the air compression chambers 808. In the schematic of FIG. 24a, the air container is substantially empty. FIG. 24b illustrates the device 10 in operation. By pressing the buttons 15, air is pushed from the chambers 808 via the air tubes 810 and the unidirectional valves 803 into the air container 802. The air container 802 inflates and causes actuation of the reservoir 220 to thus cause dispensation of the fluid from the reservoir 220. The air container 802 remains inflated as the air movement out is limited by the unidirectional valves 803. In some embodiments, air movement into the air compression chambers is directed by unidirectional valves enabling entrance of ambient air into the chamber and preventing its release from the air compression chambers.

Figure 25A:
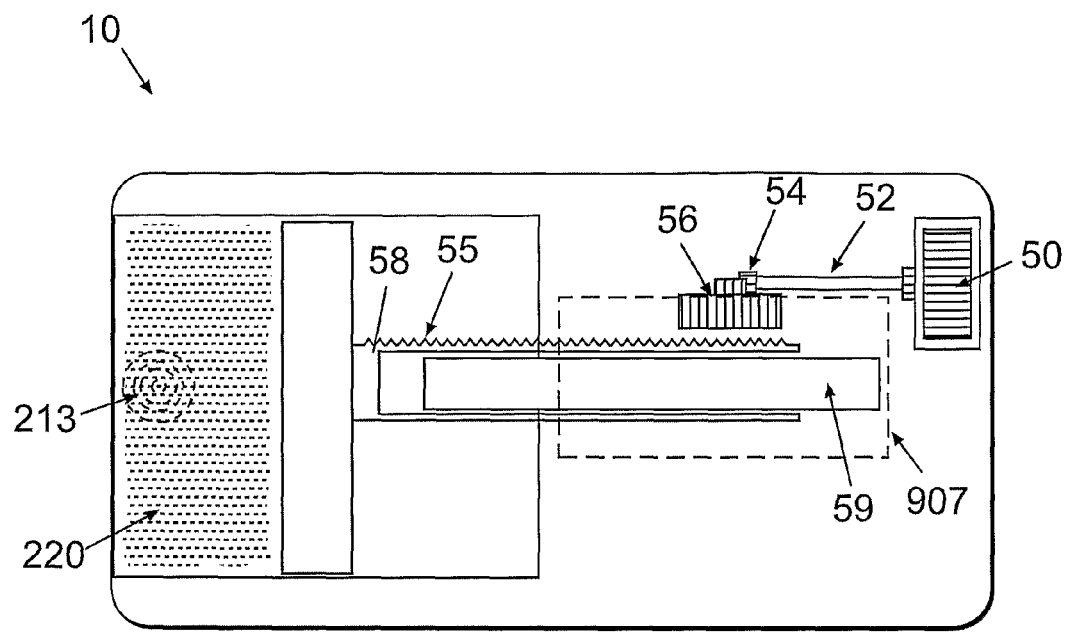
FIGS. 25a-c are schematic diagrams of another exemplary configuration for a fluid delivery device with a piston-based mechanism.
Figure 25B:
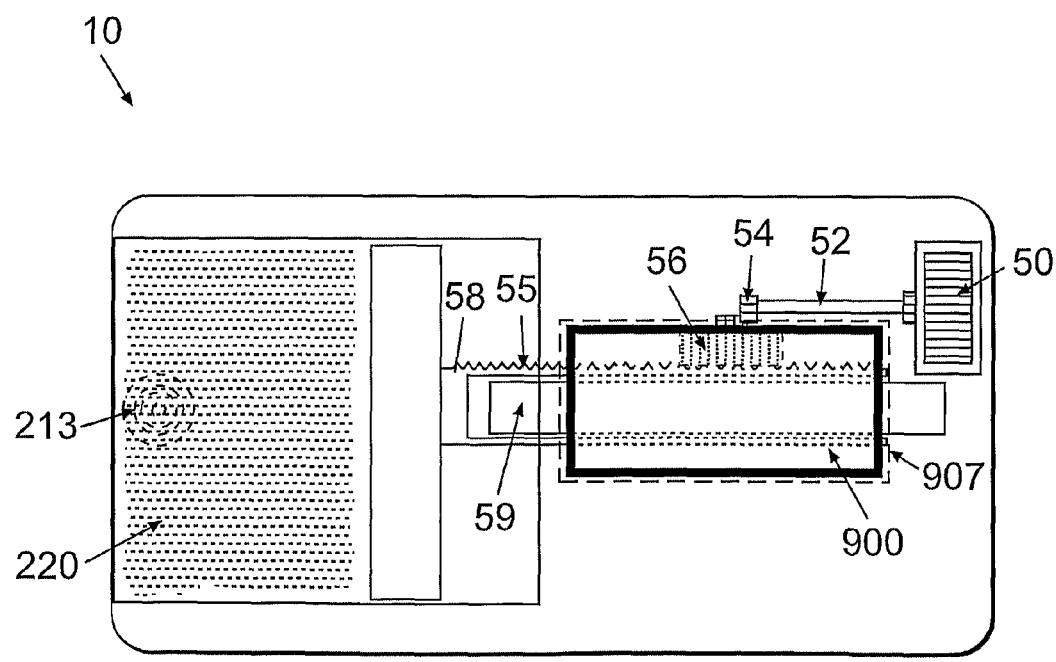
Figure 25C:
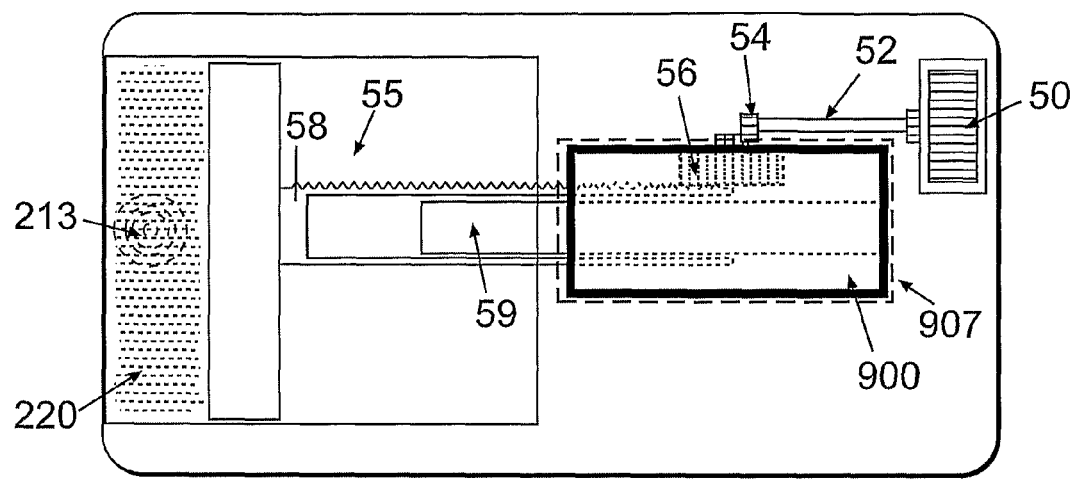

Referring to FIG. 25a, a schematic diagram of an exemplary device 10 prior to its connection to an indicator (counter) 900 is shown. As shown in FIG. 25a, racks of the rod 58 and racks of the gear 56 are not engaged at that point. Thus, rotating the gear 56 will not move the plunger 55. FIG. 25b illustrates an exemplary device 10 after connection of the counter 900. The connection of the counter 900 to its housing 907 engages the gear 56 and the threaded rod 58. FIG. 25c illustrates the device 10 in operation. By turning the rotation wheel 50, a set of gears (cog wheels) are actuated. The teeth of the gear 56 and the thread of the threaded rod 58 are configured to engage and cause the plunger 55 to move in a forward direction, which causes infusion to occur.

Figure 26A:
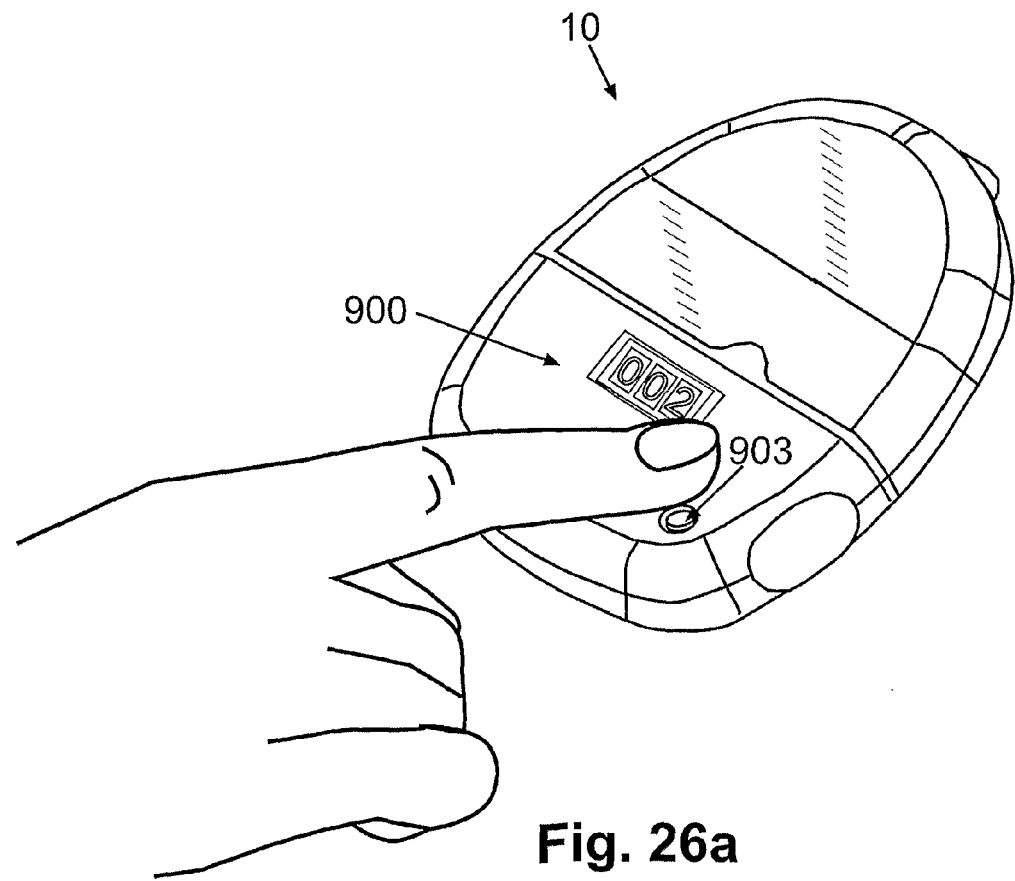
FIGS. 26a-b are perspective views of an exemplary fluid delivery device with a detachable counter.
Figure 26B:
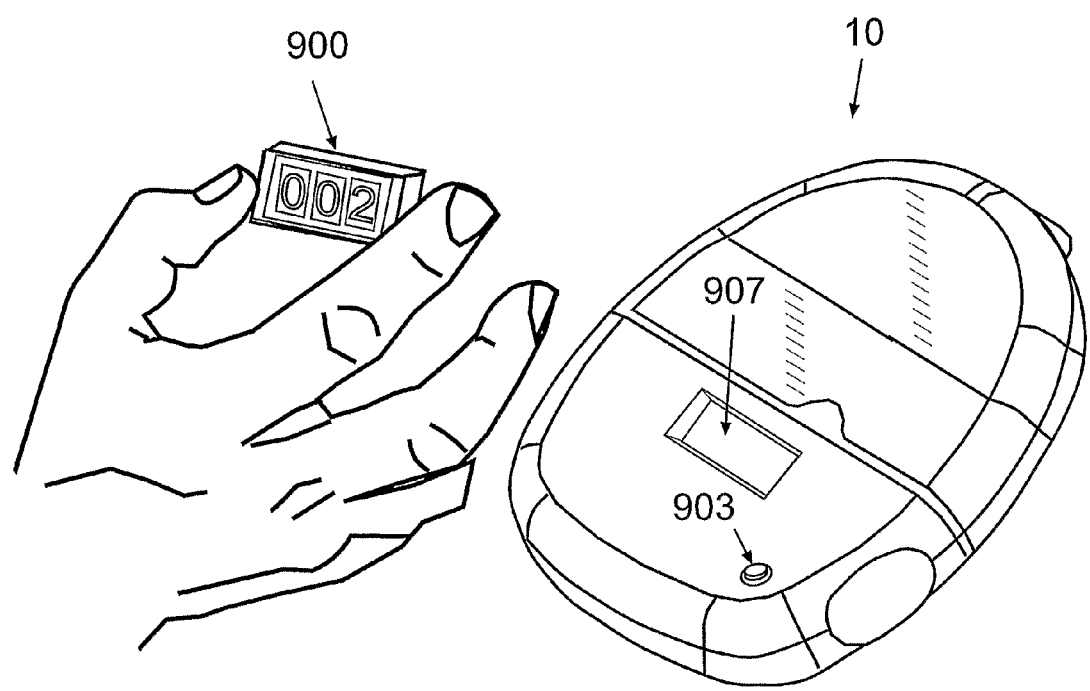

Referring to FIGS. 26a-b, perspective views of an exemplary detachable digital counter 900 to facilitate reservoir content monitoring and control is shown. Detaching the counter 900 enables the patient to estimate the status of the dispensing device 10 without suspending its operation. FIG. 26a illustrates the digital counter 900 being detached from its housing 907. The counter 900 can be detached by, for example, pressing a release button 903. FIG. 26b illustrates the counter clock 900 being grasped by the patient (e.g., held in the patient's hand). The patient can connect and/or disconnect the digital counter 900 while the pump 10 remains attached to the body and in continued operation. The counter 900 may be a mechanical, electrical, optical or electrochemical counter. In some embodiments, the counter and the dispensing device may communicate wirelessly, enabling status update of the dispensing device when the counter is detached from the device.

Referring to FIGS. 27a-28b, schematic diagrams of exemplary durable optical counter 900 are shown.

Figure 27A:
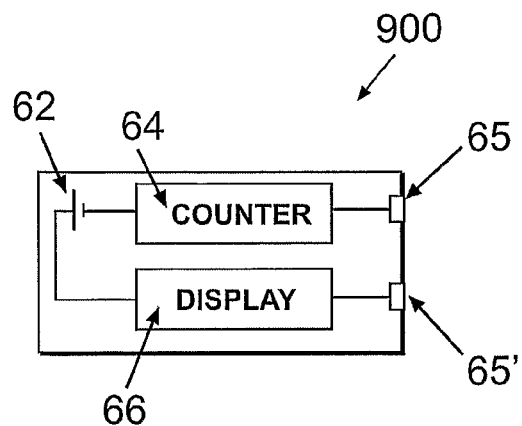
FIGS. 27a-c are schematic diagrams illustrating connection of an exemplary counter to a fluid delivery device.
Figure 27B:
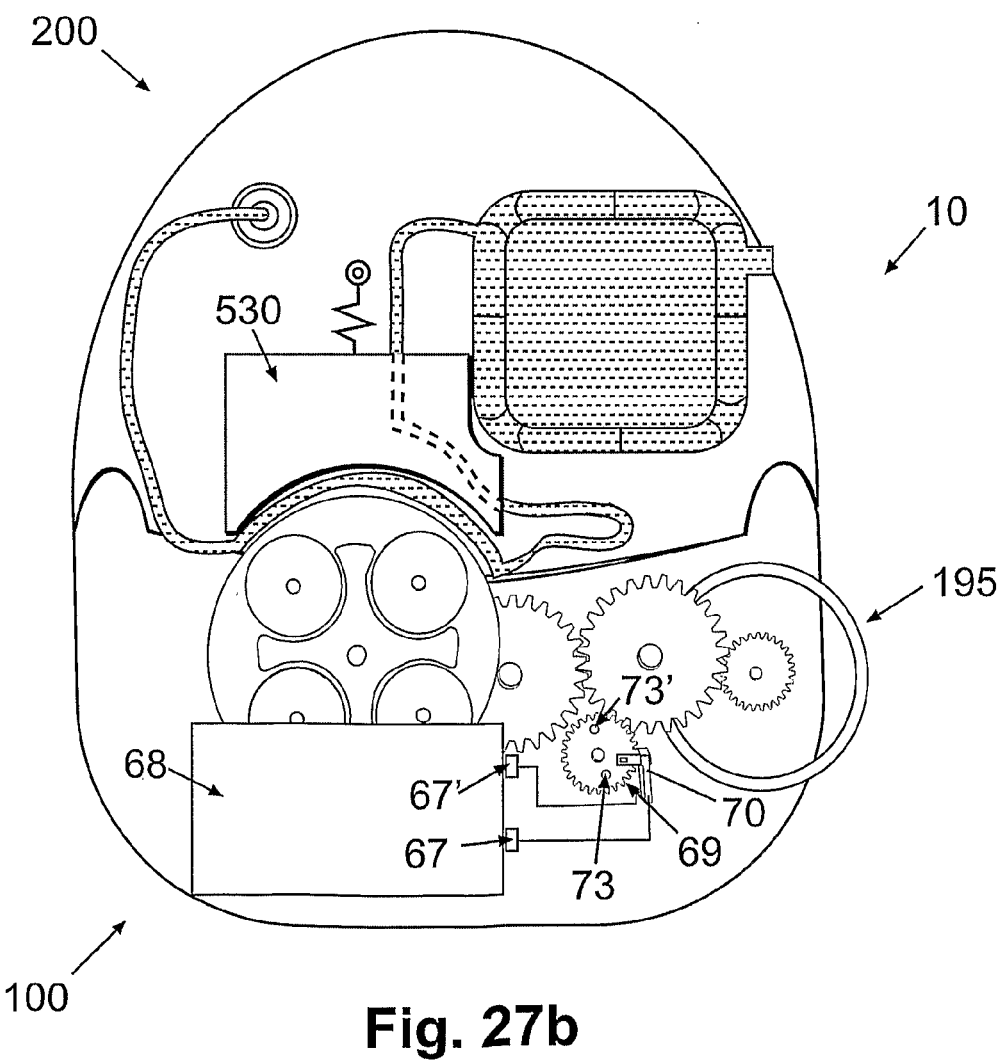
Figure 27C:
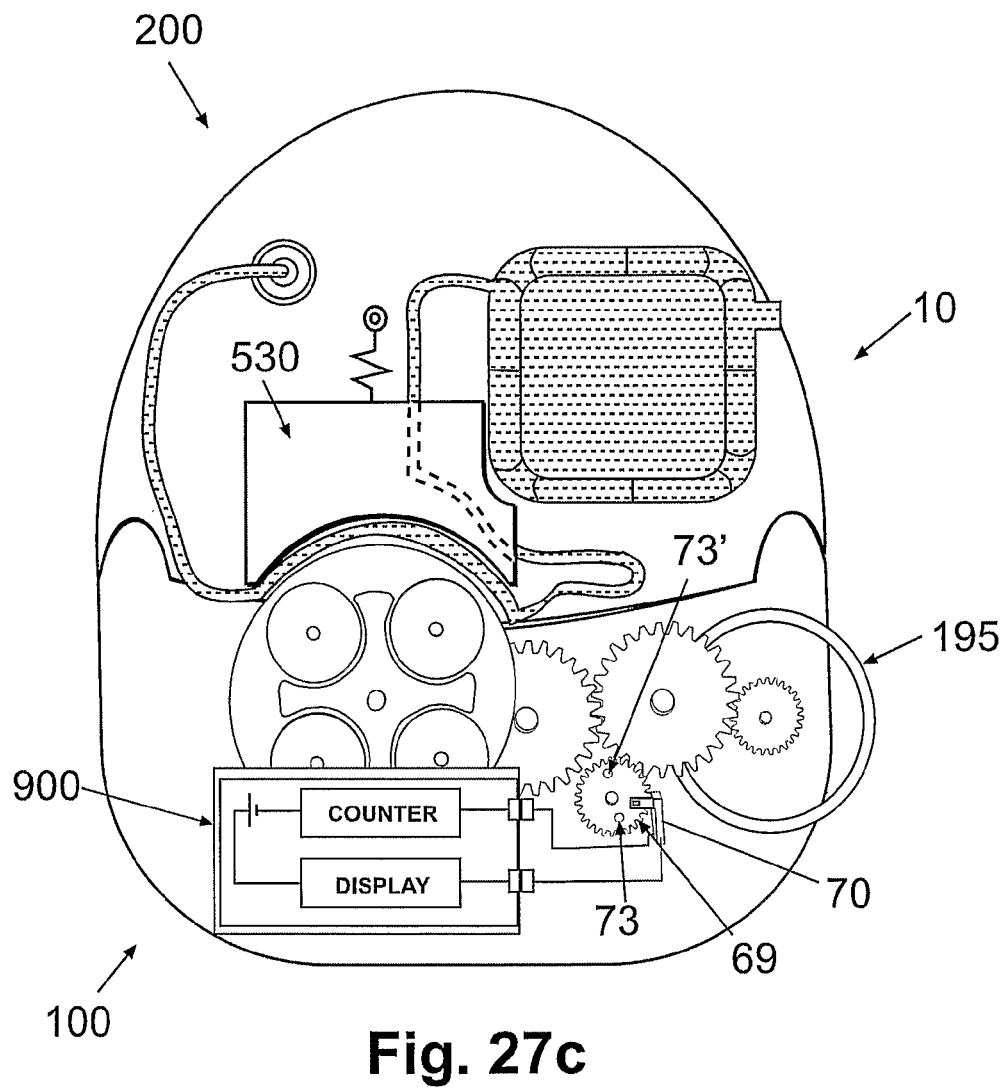

FIG. 27a is a schematic diagram of an exemplary embodiment of a counter 900. The counter 900 includes of a power source (e.g., a battery 62), and two connectors 65 and 65', a counting controller 64 to perform the counting operations and a display 66. FIG. 27b is a schematic diagram of an exemplary fluid delivery device 10 (e.g., a device implemented using a peristaltic-based pumping mechanism) without the counter 900 being connected to the device. The reusable part 100 of the device 10 includes a measurement unit to determine the extent of fluid delivery. Such a measurement unit may include an optical sensing unit 70 and two connectors 67 and 67'. The optical sensing unit 70 is configured to detect one or more markings disposed on the power-transfer mechanism (the driving mechanism). Detection of the one or more marking is indicative that a pre-determined amount of therapeutic fluid was delivered. The optical sensing unit includes a source of light and a detector. The source of light and the detector can be configured to be located on each side of one of the gears constituting the driving mechanism (e.g., the cog wheel 69). In some embodiments, the markings on the cog wheel 69 may be holes 73 and 73'. FIG. 27c depicts the counter 900 being connected to the device 10. By connecting the counter 900 to the device 10, the device's electrical circuit is closed and thereby enables measurement of data by the optical sensor 70, wherein such data is forwarded to the counter 900 and displayed. Specifically, the light source of the optical unit 70 is configured to illuminate a light beam towards one surface of the cog wheel 69. As the cog wheel rotates, the position of at least one of the holes will cross the path of the illuminated light beam, and as a result the light beam will pass through the hole and be detected by the sensor. Detection of the light beam will thus indicate that a particular amount of fluid (corresponding to the amount of fluid resulting from rotation of the cog wheel 69 by a certain amount) has been delivered.

Figure 28A:
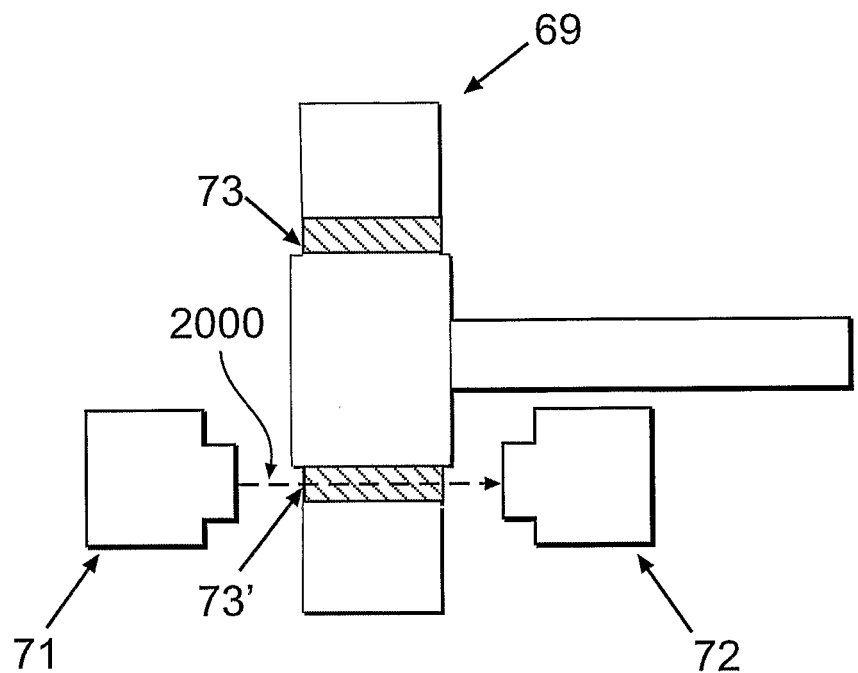
FIGS. 28a-b are schematic diagrams of an exemplary counter implemented with an optical sensing mechanism.
Figure 28B:
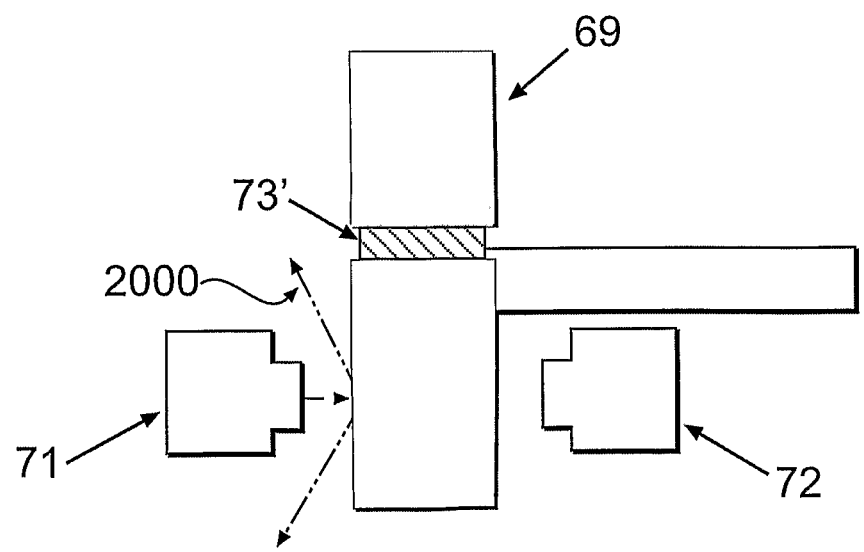

FIG. 28a illustrates light 2000 passing through one of the holes 73 in the cog-wheel 69 from the light source 71 to the optical detector 72. FIG. 28b illustrates light 2000 being blocked when it cannot pass through the cog wheel 69 (thus indicating that the pre-determined amount of fluid has not yet been fully delivered).

Figure 29A:
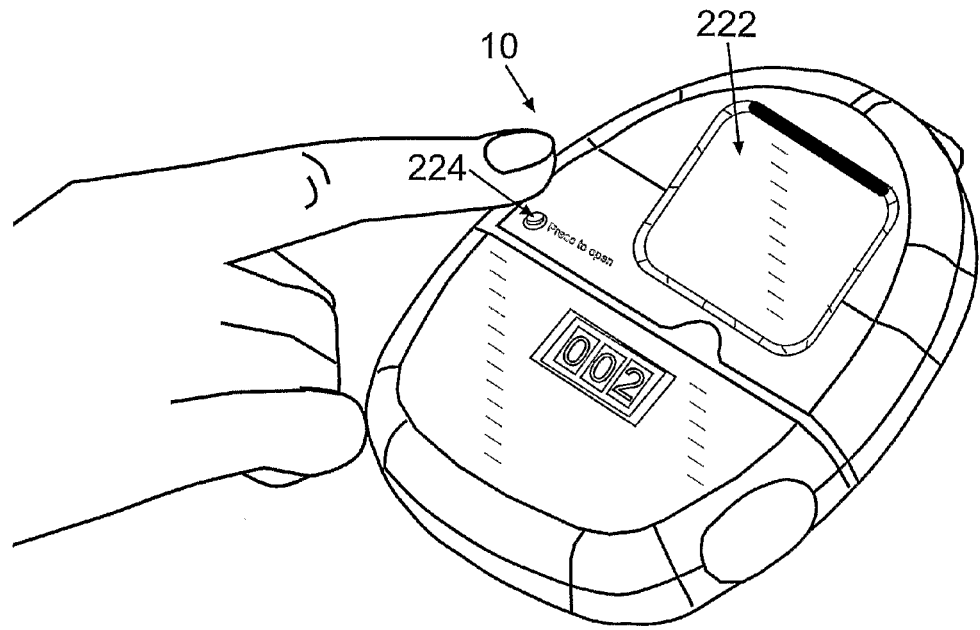
FIGS. 29a-c are perspective views of an exemplary fluid delivery device with a detachable reservoir.
Figure 29B:
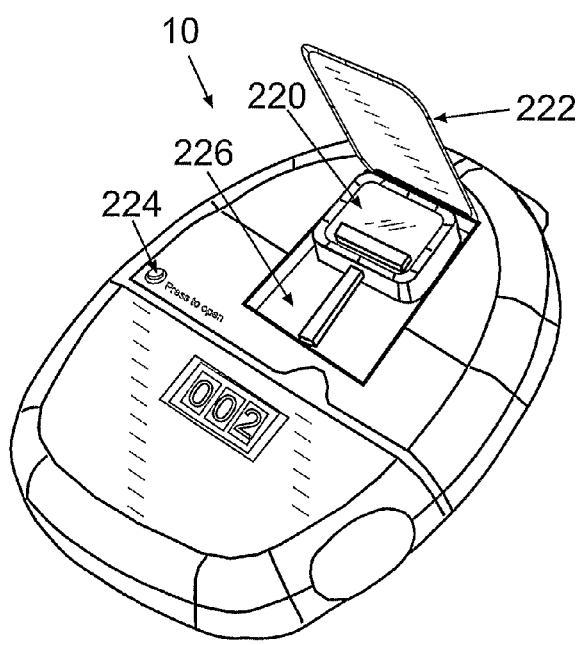
Figure 29C:
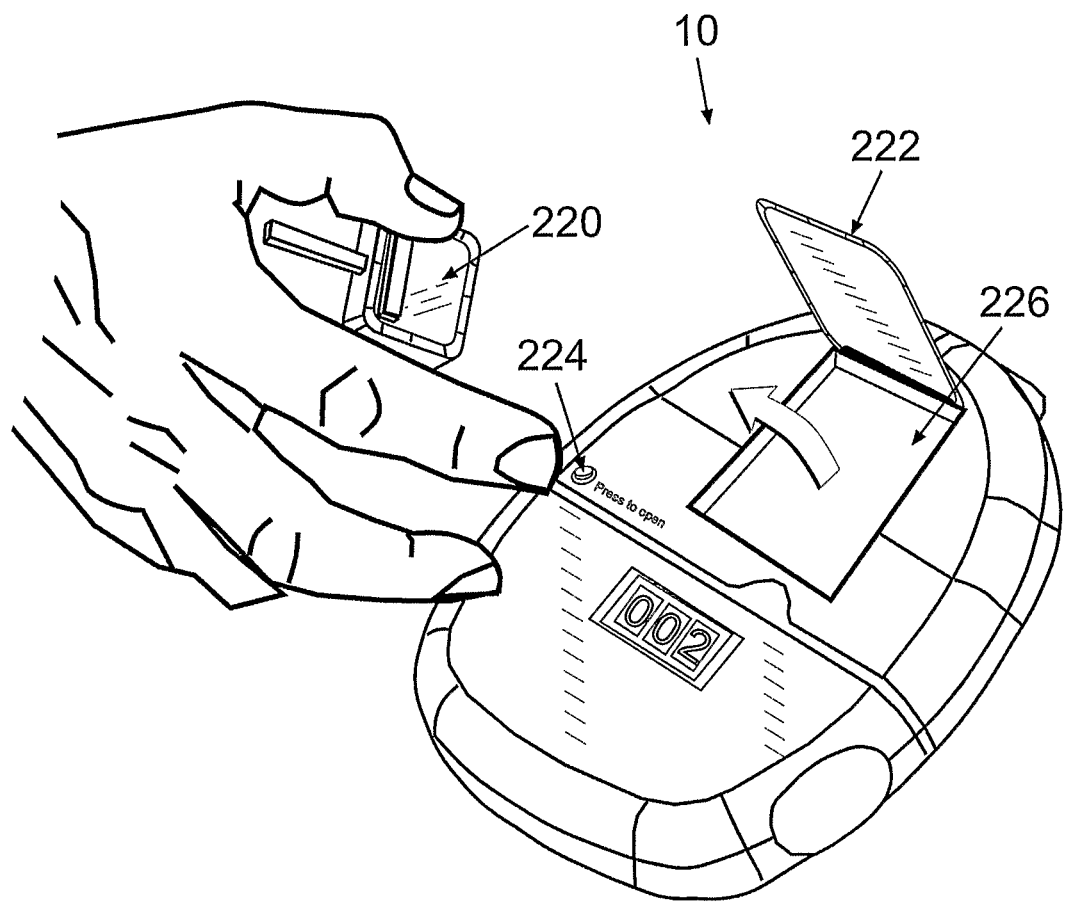

FIGS. 29a-c illustrate exemplary ejection of a replaceable reservoir. Patients of Type 2 DM pumps use reservoirs with different reservoir volumes (e.g., different amount of insulin) depending on various medical and body conditions/needs. Replacing only the reservoir within the dispensing device 10 enables the patient to use the same dispensing patch unit 10 and change the amount of fluid to be delivered without replacing the whole patch unit 10. FIG. 29a illustrates an exemplary reservoir cover 222 opened by pressing a button 224. FIG. 29b illustrates the reservoir 220 inside its chamber 226 while the chamber cover 222 is open. FIG. 29c illustrates ejection of the reservoir 220 from the chamber 226.

Figure 30A:
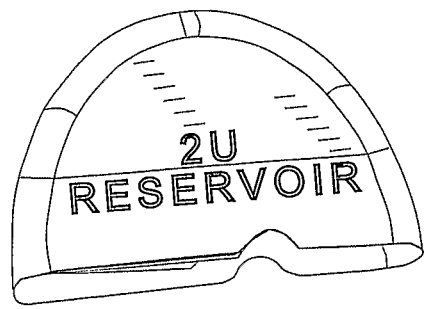
FIGS. 30a-b are views of exemplary reservoirs of different sizes.
Figure 30A:
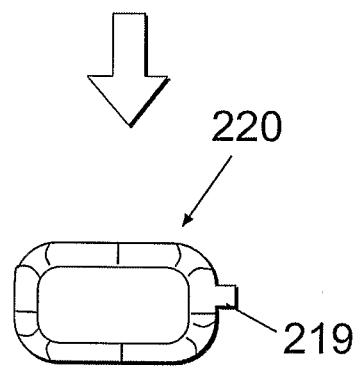
Figure 30B:
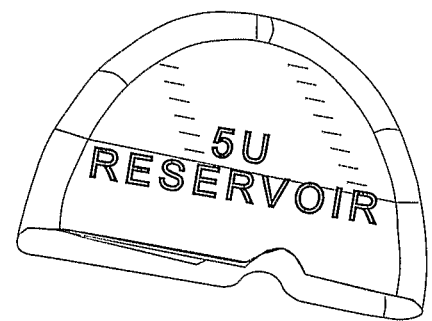
Figure 30B:
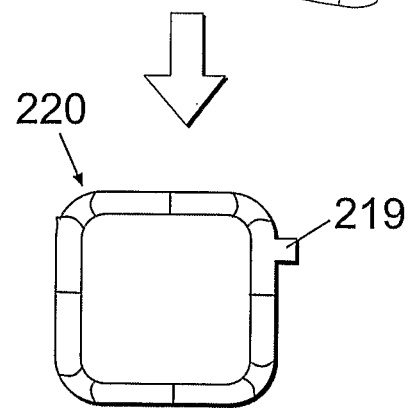

FIG. 30a-b illustrate exemplary various-size reservoirs 220 that may be employed in the dispensing device 10. Particularly, FIG. 30a shows a 2 IU size insulin reservoir 220, while FIG. 30b shows a 5 IU insulin reservoir 220.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims.

The claims presented are representative of the inventions disclosed herein. Other, unclaimed inventions are also contemplated.

The invention claimed is:

1. A portable ambulatory therapeutic fluid delivery device for delivering a therapeutic fluid in bolus doses into a body of a patient, the device comprising:
   at least one housing connectable to a cannula, and
   a cradle securable to the patient's skin, wherein the cradle is configured for releasably receiving the at least one housing enabling connection and disconnection of the at least one housing therefrom;
   the at least one housing including:
      a reservoir for storing, a therapeutic fluid;
      a mechanically powered pumping mechanism for delivering one or more bolus doses of the therapeutic fluid from the reservoir to the body of the patient through the cannula, wherein the pumping mechanism is configured to operate without using electrically-generated power; and
   a. power-transfer mechanism for transferring manual power provided by a user to mechanically actuate the pumping mechanism; and
   wherein the at least one housing includes:
      a disposable part housing including at least a part of the reservoir and an outlet port for enabling passage of the fluid to the body of the patient; and
      a reusable part housing removably attachable to the disposable part, the reusable part housing including at least a portion of the pumping mechanism and the power-transfer mechanism; wherein the device is operable upon attachment of the reusable part housing and the disposable part housing; and
   wherein the reservoir is configured to be filled with the fluid prior to attachment of the disposable part to the reusable part.

2. The device according to claim 1, wherein the therapeutic fluid includes one or more of: insulin, pramlintide acetate and exenatide.

3. The device according to claim 1, wherein the power-transfer mechanism comprises a user-actuated rotatable wheel and one or more gears for transferring power between the wheel and the pumping mechanism for causing delivery of a bolus dose in response to rotation of the user-actuated wheel.

4. The device according to claim 3, wherein the one or more gears comprise at least one cog wheel in mechanical communication with at least one worm gear and a screw-nut coupled to the worm gear and further coupled to a piston of the pump such that rotation of the worm gear causes displacement of the piston.

5. The device according to claim 1, wherein the pump comprises:
   a piston coupled to the reservoir, the piston further coupled to the actuator; wherein movement of the piston by the actuator results in displacement of the piston for delivery of a bolus dose.

6. The device according to claim 1, further comprising a limiter for limiting displacement of the pumping mechanism, wherein the limiter prevents displacement of the pumping mechanism or the power-transfer mechanism beyond a preset spatial position defined by the limiter corresponding to a bolus dose.

7. The device according to claim 6, wherein the bolus dose corresponds to a predetermined amount configurable by user adjustment of the limiter.

8. The device according to claim 6, wherein the limiter comprises a stationary block for engaging a projection extending from an end of the piston such that upon contact between the stationary block and the projection extending from the end of the piston, further displacement of the piston is prevented.

9. The device according to claim 1, wherein the pumping mechanism comprises a peristaltic pump, wherein the peristaltic pump comprises a rotor coupled to a delivery tube for delivering one or more bolus doses, the rotor further coupled to the actuator such that manual power transferred by the actuator causes rotation of the rotor resulting in displacement of therapeutic fluid contained within the delivery tube.

10. The device according to claim 1, wherein the actuator includes a spiral spring configured to operate the pumping mechanism upon activation of the spring by the patient, and wherein the actuator further comprises: at least one gear coupled to the spiral spring, wherein the spiral spring is biased in a first rotational direction; and a string coupled to the spiral spring for causing rotation of the spiral spring in a second rotational direction for increasing in the tension of the spiral spring, wherein upon release of the string, the spiral spring rotates in the first rotational direction resulting in movement of the power-transfer mechanism resulting in pumping mechanism operation.

11. The device according to claim 10, further comprising a limiter for limiting displacement of the pumping mechanism, wherein the limiter prevents the string from moving beyond a predetermined position such that upon release of the string, the spiral spring rotates a predetermined radial distance causing delivery of a bolus dose by the pumping mechanism corresponding with the predetermined amount.

12. The device according to claim 1, wherein the pumping mechanism comprises an inflatable air container configured for driving fluid from the reservoir, and wherein the power-transfer mechanism comprises at least one air injection device for delivering air to the inflatable air container.

13. The device according to claim 12, wherein the at least one air injection device comprises: an air tube in communication with the inflatable air container; and an air compression chamber in communication with the air tube, the air compression chamber including a displaceable plunger, wherein upon movement of the plunger by the patient, air is displaced from the air compression chamber into the inflatable air container through the air tube.

14. The device according to claim 1, further comprising an indicator for indicating operation of the pumping mechanism.

15. The device according to claim 14, wherein the indicator includes one or more of: an audible indicator for producing a sound and a visual indicator for producing a visual signal.

16. The device according to claim 1, further comprising a counter for displaying a value representative of an amount of therapeutic fluid delivered by operation of the device.

17. The device according to claim 16, wherein operation of the counter is based on operation of the power-transfer mechanism.

18. The device according to claim 16, wherein the counter comprises a mechanically detachable counter housing configured for attaching and detaching from the at least one housing.

19. The device according to claim 1, further comprising a measurement unit for determining an extent of fluid delivered.

20. The device according to claim 19, wherein the measurement unit comprises an optical unit for detecting one or more markings disposed on the actuator, wherein detection of the one or more markings corresponds to a pre-determined amount of fluid delivered.

21. The device according to claim 20, wherein the actuator comprises a gear having one or more openings extending from one surface of the gear to the other surface, and wherein the optical unit comprises: a light source for producing a light beam to illuminate one surface of the gear; and a light sensor for detecting light passing through the one or more openings.

22. The device according to claim 1, wherein the at least one housing is configured for receiving different size reservoirs.

23. The portable ambulatory therapeutic fluid delivery device according to claim 1, wherein the power-transfer mechanism comprises a user-actuated rotatable wheel.

24. The portable ambulatory therapeutic fluid delivery device according to claim 1, wherein the cradle comprises a well enabling passage of the cannula there through.

\* \* \* \* \*